(12) United States Patent
Parikh

(10) Patent No.: US 11,116,784 B2
(45) Date of Patent: Sep. 14, 2021

(54) NIACINAMIDE (NAM) IN ISCHEMIC TISSUE INJURY

(71) Applicant: Beth Israel Deaconess Medical Center, Inc., Boston, MA (US)

(72) Inventor: Samir M. Parikh, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 81 days.

(21) Appl. No.: 16/079,963

(22) PCT Filed: Feb. 21, 2017

(86) PCT No.: PCT/US2017/018682
§ 371 (c)(1),
(2) Date: Aug. 24, 2018

(87) PCT Pub. No.: WO2017/147058
PCT Pub. Date: Aug. 31, 2017

(65) Prior Publication Data
US 2019/0070211 A1 Mar. 7, 2019

Related U.S. Application Data

(60) Provisional application No. 62/432,458, filed on Dec. 9, 2016, provisional application No. 62/300,696, filed on Feb. 26, 2016.

(51) Int. Cl.
*A61K 31/7084* (2006.01)
*A61K 31/4409* (2006.01)
*A61K 31/44* (2006.01)
*A61P 41/00* (2006.01)
*A61K 31/403* (2006.01)
*A61K 31/455* (2006.01)
*A61K 31/706* (2006.01)
*A61K 31/711* (2006.01)
*A61P 13/12* (2006.01)
*C12N 15/113* (2010.01)
*A61P 9/10* (2006.01)
*G01N 33/50* (2006.01)

(52) U.S. Cl.
CPC ........ *A61K 31/7084* (2013.01); *A61K 31/403* (2013.01); *A61K 31/44* (2013.01); *A61K 31/4409* (2013.01); *A61K 31/455* (2013.01); *A61K 31/706* (2013.01); *A61K 31/711* (2013.01); *A61P 9/10* (2018.01); *A61P 13/12* (2018.01); *A61P 41/00* (2018.01); *C12N 15/113* (2013.01); *G01N 33/5038* (2013.01); *C12N 2310/11* (2013.01); *C12N 2310/14* (2013.01); *G01N 2800/347* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 9,072,766 B2 * | 7/2015 | Kahn ................. C12N 15/1137 |
| 2011/0070185 A1 | 3/2011 | Cai et al. |
| 2012/0015901 A1 | 1/2012 | Winderickx et al. |
| 2012/0172584 A1 | 7/2012 | Sauve et al. |
| 2013/0243790 A1 * | 9/2013 | Kahn ................. A61K 39/3955 424/158.1 |
| 2014/0024677 A1 | 1/2014 | Schnellmann et al. |
| 2015/0072950 A1 | 3/2015 | Sauve et al. |
| 2016/0060226 A1 * | 3/2016 | Pellicciari ............ C07D 409/04 514/274 |
| 2018/0303861 A1 * | 10/2018 | Marcotulli ................ A61P 9/00 |

FOREIGN PATENT DOCUMENTS

| EP | 2685259 | 1/2014 |
| WO | WO 2010/025416 | 4/2010 |
| WO | WO 2010/040112 | 4/2010 |
| WO | WO-2012068463 A2 * | 5/2012 ......... A61K 39/3955 |
| WO | WO 2015/189325 | 12/2015 |
| WO | WO-2016149277 A1 * | 9/2016 ............. A23L 33/15 |

OTHER PUBLICATIONS

Yang, et al. (2002) "The effects of nicotinamide on energy metabolism following transient focal cerebral ischemia in Wistar rats." Neuroscience Letters, vol. 333:91-4. (Year: 2002).*
Molecular Effects of VitaminB3 (Niacinmamide) in acute kidney injury, first posted on Mar. 8, 2016, obtained from U.S. National Library of Medicine, clinicaltrials.gov, NCT02701127, retrieved on-line Nov. 4, 2020, pp. 1-6. (Year: 2020).*
Bullucketal. Nature Medicine 24, 1304-1312 (Year: 2018).*
Katsyuba et al. Nature 363, 354-359 (Year: 2018).*
Mehr et al. Nature Medicine 24, 1351-1359 (Year: 2018).*
Denker et al. Eur. J. Internal Med. 22, pp. 348-354 (Year: 2011).*
National kidney foundation Acute Kidney Injury, http://www.kidney.org/atoz/acutekidneyinjury, retrieved on line Nov. 4, 2020, pp. 1-3 (Year: 2020).*
Agudelo et al., "Skeletal Muscle PGC-1α1 Modulates Kynurenine Metabolism and Mediates Resilience to Stress-Induced Depression" Cell, Sep. 2014, 159(1):33-45.
Antonica et al., "Generation of functional thyroid from embryonic stem cells," Nature, Nov. 2012, 491:66-71.
Arany et al., "HIF-independent regulation of VEGF and angiogenesis by the transcriptional coactivator PGC-1α," Nature, Feb. 2008, 451:1008-12.
Bae et al., "Hydrogen Peroxide-Responsive Nanoparticle Reduces Myocardial Ischemia/Reperfusion Injury," J. Am. Heart Assoc., Nov. 2016, 5(11):e003697.
Bai et al., "PARP-1 Inhibition Increases Mitochondrial Metabolism through SIRT1 Activation," Cell Metab., Apr. 2011, 13(4):461-8.

(Continued)

Primary Examiner — Brian Whiteman
(74) Attorney, Agent, or Firm — Fish & Richardson P.C.

(57) ABSTRACT

Methods of treating ischemic tissue injury or kidney disease, e.g., delayed graft function, that include administering a Nicotinamide adenine dinucleotide (NAD)/niacinamide (NAM) pathway agonist.

12 Claims, 45 Drawing Sheets

Specification includes a Sequence Listing.

(56) References Cited

OTHER PUBLICATIONS

Bostrom et al., "A PGC1-α-dependent myokine that drives brown-fat-like development of white fat and thermogenesis," Nature, Jan. 2012, 481:463-8.
Breyer et al., "Functional and molecular aspects of renal prostaglandin receptors," J. Am. Soc. Nephrol., Jan. 1996, 7(1):8-17.
Collins et al., "The management of nicotinamide and nicotinic acid in the mouse," J. Biol. Chem., Feb. 1972, 247(3):778-83.
Ebrahimkhani et al., "Aag-initiated base excision repair promotes ischemia reperfusion injury in liver, brain, and kidney," Proc. Natl. Acad. Sci. USA, Nov. 2014, 111(45):E4878-86.
Feingold et al., "Inflammation stimulates niacin receptor (GPR109A/HCA2) expression in adipose tissue and macrophages," J. Lipid Res., Oct. 2014; 55:2501-8.
Feldkamp et al., "Preservation of complex I function during hypoxia-reoxygenation-induced mitochondrial injury in proximal tubules," Am. J. Physiol. Renal Physiol., 2004, 286:F749-59.
Gomes et al., "Declining NAD+ induces a pseudohypoxix state disrupting nuclear-mitochondrial communication during aging," Cell, Dec. 2013, 155(7):1624-38.
Hanson et al., "Nicotinic acid- and monomethyl fumarate-induced flushing involves GPR109A expressed by keratinocytes and COX-2-dependent prostanoid formation in mice," J. Clin. Invest., Aug. 2010, 120(8):2910-9.
International Preliminary Report on Patentability in International Application No. PCT/US2017/018682, dated Sep. 7, 2018, 12 pages.
International Search Report & Written Opinion Application No. PCT/US2017/018682, dated Apr. 14, 2017, 14 pages.
Jesinkey et al., "Formoterol restores mitochondrial and renal function after ischemia-reperfusion injury," J. Am. Soc. Nephrol., Jun. 2014, 25(6):1157-62.
Kang et al., "Muscle immobilization and remobilization downregulates PGC-1α signaling and the mitochondrial biogenesis pathway," J. Appl. Physiol., Dec. 2013, 115(11):1618-25.
Kim et al., "Composite Three-Marker Assay for Early Detection of Kidney Cancer," Cancer Epidemiol. Biomarkers Prev., Mar. 2013, 22(3):390-8.
Kraus et al., "Nicotinamide N-methyltransferase knockdown protects against diet-induced obesity," Nature, Apr. 2014, 508:258-62.
Legendre et al., "Factors influencing long-term outcome after kidney transplantation," Transpl. Int., 2014, 27(1):19-27.
Lewington et al., "Raising awareness of acute kidney injury: a global perspective of a silent killer," Kidney Int., Sep. 2013, 84(3):457-67.
Liu et al., "Nutrient sensing by the mitochondrial transcription machinery dictates oxidative phosphorylation," J. Clin. Invest., Feb. 2014, 124(2)768-84.
Mauk et al., "Effect of prostaglandin E administration in a nephrotoxic and a vasoconstrictor model of acute renal failure," Kidney Int., Aug. 1977, 12(2):122-30.
Morigi et al., "Sirtuin 3-dependent mitochondrial dynamic improvements protect against acute kidney injury," J. Clin. Invest., Feb. 2015, 125(2):715-26.
Mukhopadhyay et al., "Mitochondrial reactive oxygen species generation triggers inflammatory response and tissue injury associated with hepatic ischemia-reperfusion: therapeutic potential of mitochondrially targeted antioxidants," Free Radic. Biol. Med., Sep. 2012, 53(5):1123-38.
Naidoo et al., "Development of a scalable synthesis of P7C3-A20, a potent neuroprotective agent," Tetrahedron Letters, Aug. 2013 54(33):4429-31.
Nakahata et al., "Circadian Control of the NAD+ Salvage Pathway by CLOCK-SIRT1," Science, May 2009, 324(5927):654-7.
Ojo et al., "Delayed Graft Function: Risk Factors and Implications for Renal Allograft Survival," Transplantation, Apr. 1997; 63(7):968-74.
Pagliarini et al., "A Mitochondrial Protein Compendium Elucidates Complex I Disease Biology," Cell, Jul. 2008, 134(1):112-23.

Papanicolaou et al., "The effect of indomethacin and prostaglandin (PGE2) on renal failure due to glycerol in saline-loaded rats," Clin. Sci. Mol. Med., Nov. 1975, 49(5):507-10.
Pieper et al., "Discovery of a Proneurogenic, Neuroprotective Chemical," Cell, Jul. 2010, 142(1):39-51.
Pozzi et al., "RNA-Mediated Gene Silencing of Nicotinamide N-Methyltransferase Is Associated with Decreased Tumorigenicity in Human Oral Carcinoma Cells," PLoS One, Aug. 2013 21:8(8):e71272.
Puigserver et al., "A Cold-Inducible Coactivator of Nuclear Receptors Linked to Adaptive Thermogenesis." Cell, Mar. 1998, 92(6):829-39.
Rajakumar et al., "Deficiency or Inhibition of CD73 Protects in Mild Kidney Ischemia-Reperfusion Injury," Transplantation, Dec. 2010, 90(12):1260-4.
Rask-Andersen et al., "Trends in the exploitation of novel drug targets," Nat. Rev. Drug Discov., Aug. 2011, 10(8):579-90.
Revollo et al., "The NAD biosynthesis pathway mediated by nicotinamide phosphoribosyltransferase regulates Sir2 activity in mammalian cells," J. Biol. Chem, Dec. 2004, 279(49):50754-63.
Rhee et al., "A genome-wide association study of the human metabolome in a community-based cohort," Cell Metab., Jul. 2013; 18(1):130-43.
Ruas et al., "A PGC-1α isoform induced by resistance training regulates skeletal muscle hypertrophy," Cell, Dec. 7, 2012, 151(6), 1319-31.
Sartini et al., "Role of nicotinamide N-methyltransferase in non-small cell lung cancer: in vitro effect of shRNA-mediated gene silencing on tumourigenicity," Biol. Chem., Mar. 2015, 396(3):225-34.
Singh et al., "Mycobacterium tuberculosis-driven targeted recalibration of macrophage lipid homeostasis promotes the foamy phenotype," Cell Host Microbe, Nov. 2012, 12(5):669-81.
Sketch et al., "Prevention of contrast media-induced renal dysfunction with prostaglandin E1: a randomized, double-blind, placebo-controlled study," Am. J. Ther., May-Jun. 2001, 8(3):155-62.
Soriano et al., "Diabetic endothelial dysfunction: the role of poly (ADP-ribose) polymerase activation," Nat. Med., Jan. 2001, 7(1):108-13.
Tanaka et al., "1-Methylnicotinamide ameliorates lipotoxicity-induced oxidative stress and cell death in kidney proximal tubular cells," Free Radical Biol. Med., Oct. 2015, 89:831-41.
Thadhani et al., "Acute renal failure," N. Engl. J. Med., May 1996, 334(22):1448-60.
Tran et al., "PGC-1α promotes recovery after acute kidney injury during systemic inflammation in mice," J. Clin. Invest., Oct. 2011; 121(10):4003-14.
Traykova-Brauch et al., "An efficient and versatile system for acute and chronic modulation of renal tubular function in transgenic mice," Nat. Med., Sep. 2008, 14:979-84.
Vafai et al., "Mitochondrial disorders as windows into an ancient organelle," Nature, Nov. 2012, 491(7424):374-83.
Walter and Kaplan, "Substituted Nicotinamide Analogues of Nicotinamide Adenine Dinucleotide," J. Biol. Chem., Aug. 1963, 238(8):2823-30.
Wang et al., "P7C3 neuroprotective chemicals function by activating the rate-limiting enzyme in NAD salvage," Cell, Sep. 2014, 158(6):1324-34.
Weidemann et al., "The fuel of respiration of rat kidney cortex," Biochem. J., Apr. 1969, 112(2):149-66.
Wu et al., "BioGPS: building your own mash-up of gene annotations and expression profiles," Nucl. Acids Res., Jan. 2016, 44(D1):D313-6.
Yarlagadda et al., "Association between delayed graft function and allograft and patient survival: a systematic review and meta-analysis," Nephrol. Dial. Transplant., Mar. 2009, 24(3):1039-47.
Yoshino et al., "Nicotinamide Mononucleotide, a Key NAD+ Intermediate, Treats the Pathophysiology of Diet- and Age-Induced Diabetes in Mice," Cell Metab., Oct. 2011, 14:528-36.
Yu et al., "Effects of nicotinamide N-methyltransferase on PANC-1 cells proliferation, metastatic potential and survival under metabolic stress," Cell Physiol. Biochem., 2015, 35(2):710-21.
Zhang et al., "Nicotinamide N-methyltransferase protein expression in renal cell cancer," J Zhejiang Univ Sci B., 2010 11(2):136-43.

(56) References Cited

OTHER PUBLICATIONS

Zsengeller et al., "Cisplatin nephrotoxicity involves mitochondrial injury with impaired tubular mitochondrial enzyme activity," J. Histochem. Cytochem., Jul. 2012, 60(7):521-9.
Raines et al., "Associated with Improved Outcomes in COVID-19-Related Acute Kidney Injury: An Observational Study," Kidney360, Jan. 1, 2020, 53 pages.
Ralto et al., "NAD + homeostasis in renal health and disease," Nature Reviews Nephrology, Feb. 2020, 16(2): 99-111.

* cited by examiner

FIG. 2H
Control
FIG. 2I
iNephPGC1α
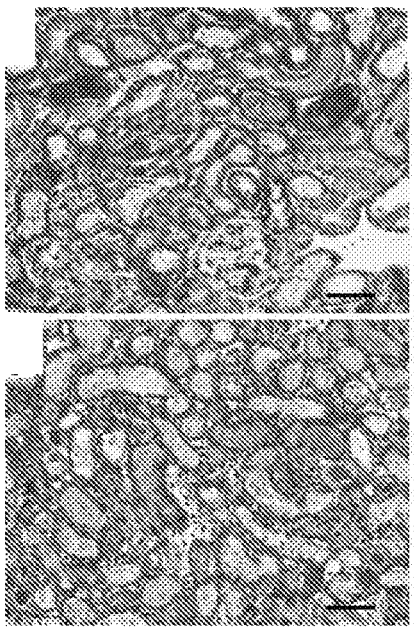
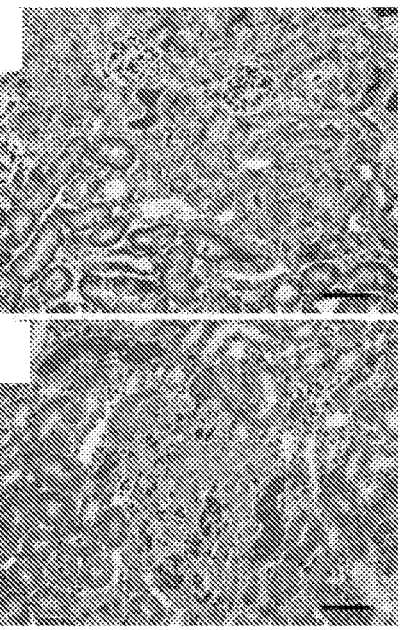
FIG. 2J
FIG. 2K
FIG. 2L
Control
FIG. 2M
iNephPGC1α
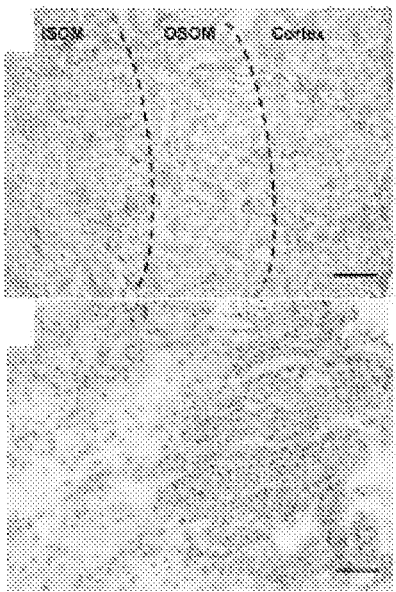
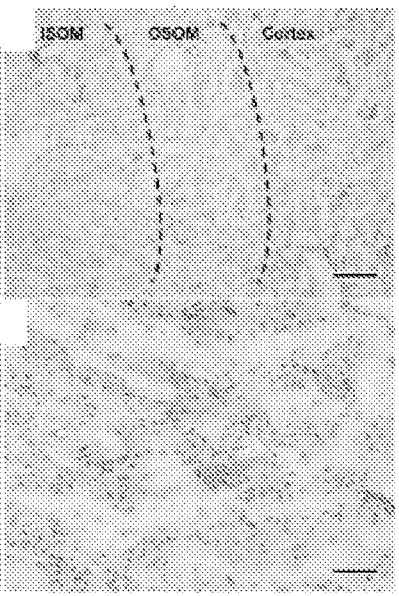
FIG. 2N
FIG. 2O

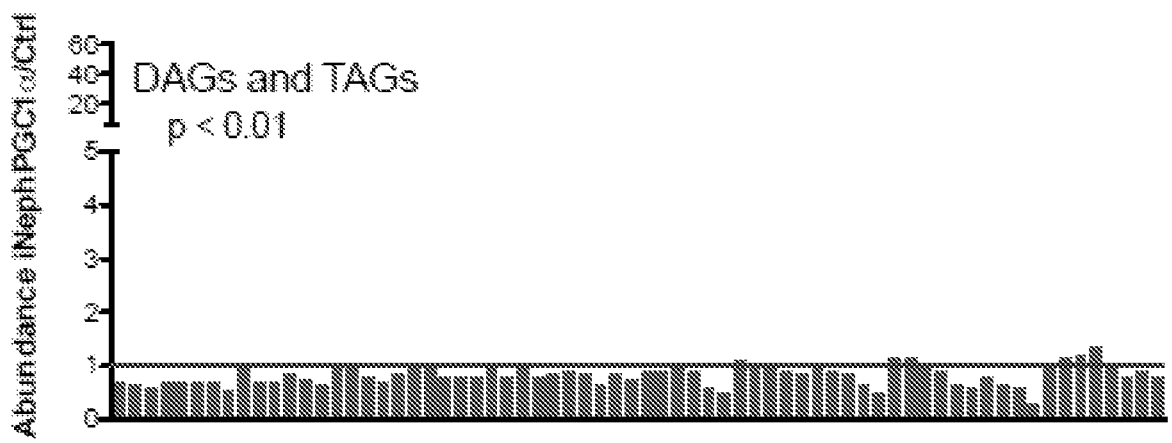
FIG. 2P
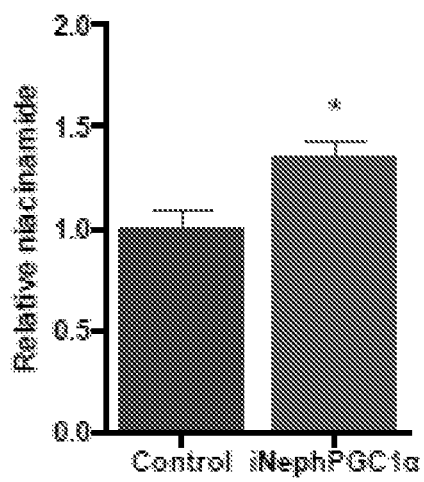
FIG. 2Q
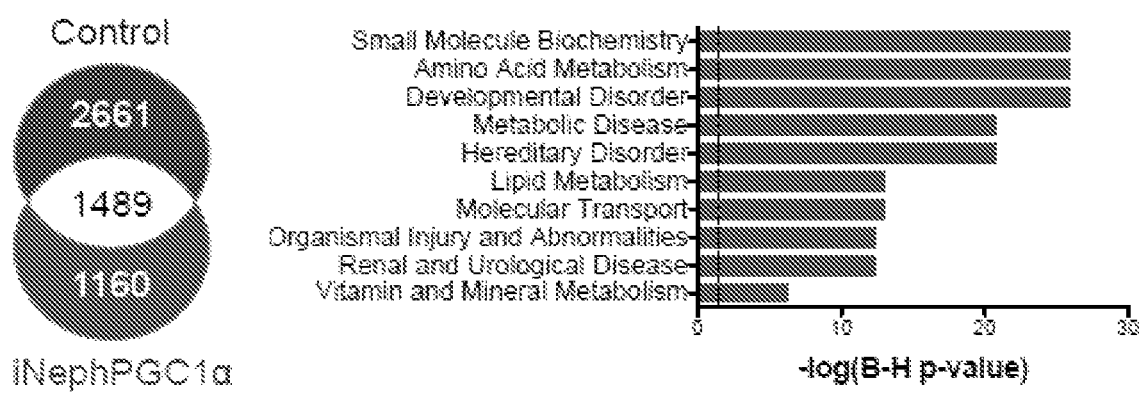
FIG. 3A
FIG. 3B

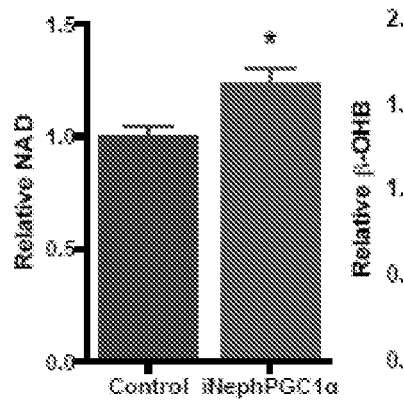
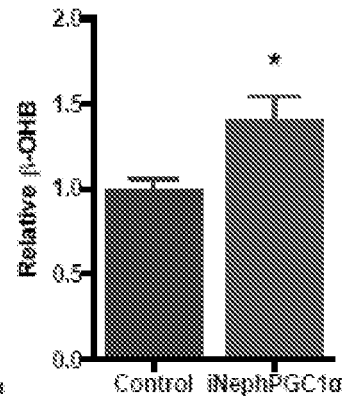
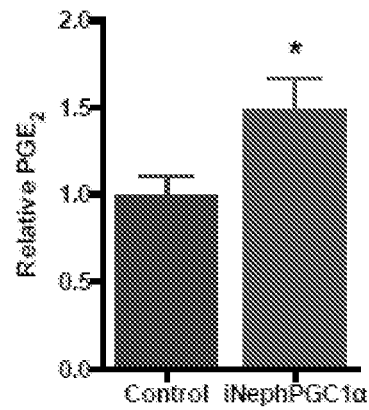
*FIG. 3M*  *FIG. 3N*  *FIG. 3O*
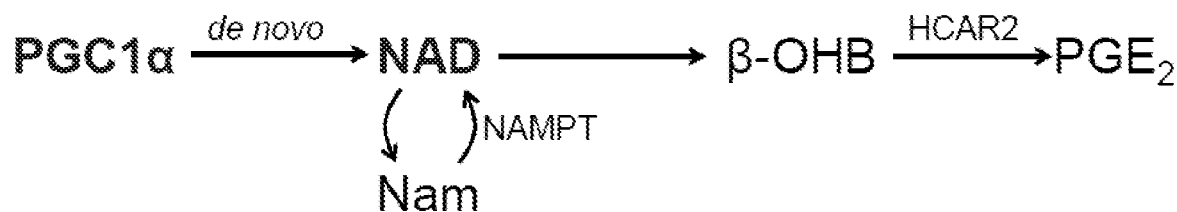
*FIG. 3P*
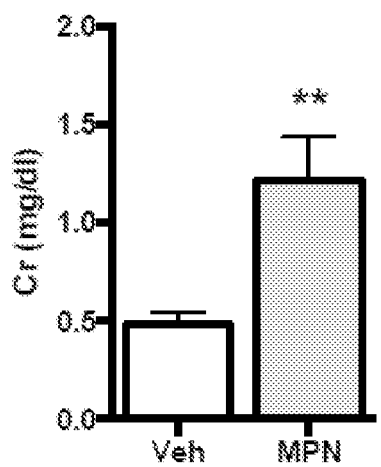
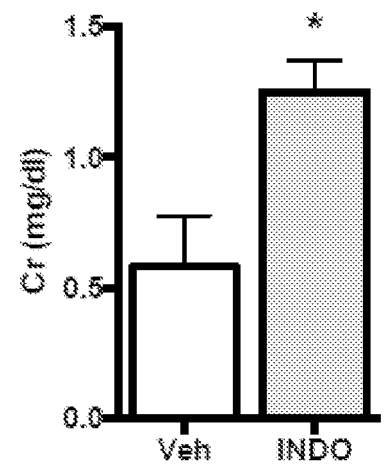
*FIG. 4A*  *FIG. 4B*

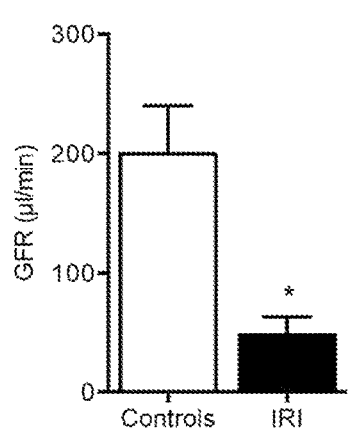
FIG. 5E
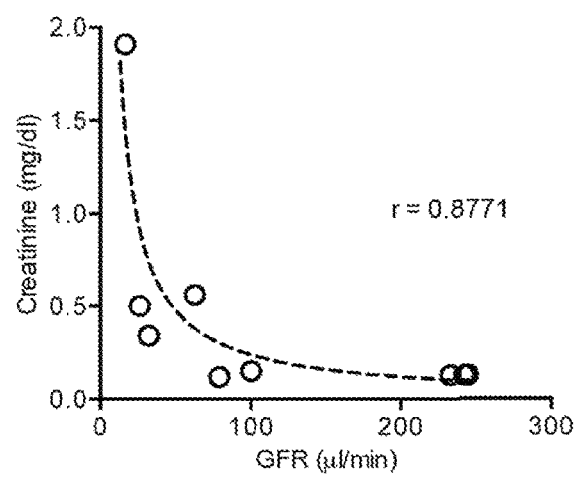
FIG. 5F
FIG. 6A
WT
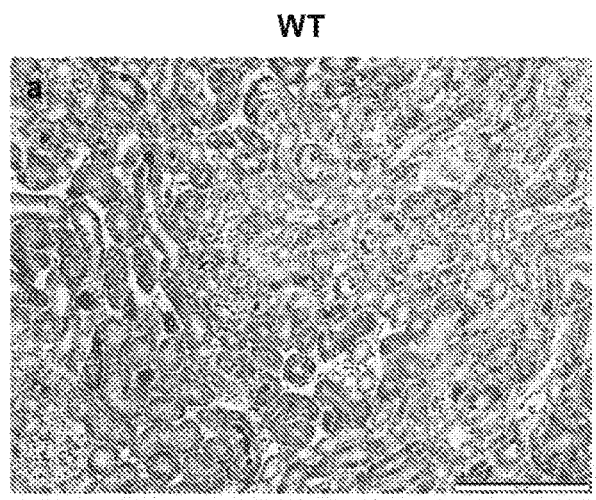
FIG. 6C
FIG. 6B
KO
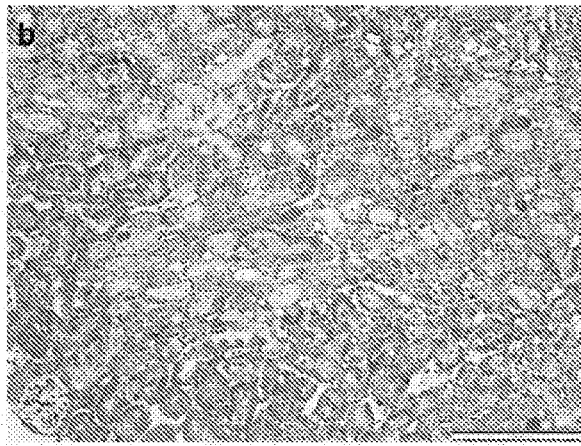
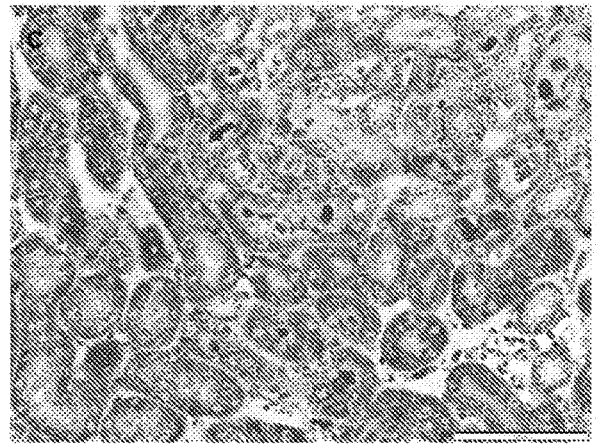
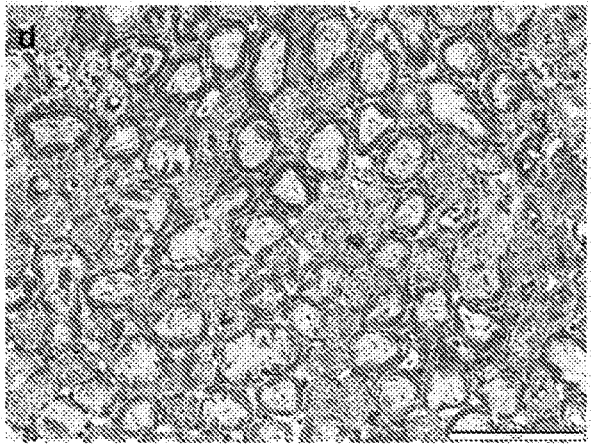
FIG. 6D

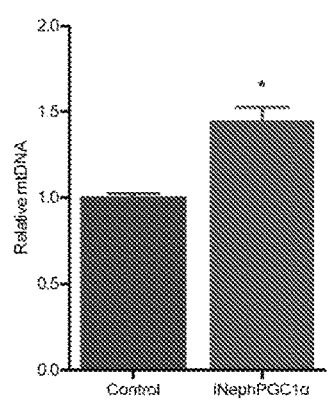
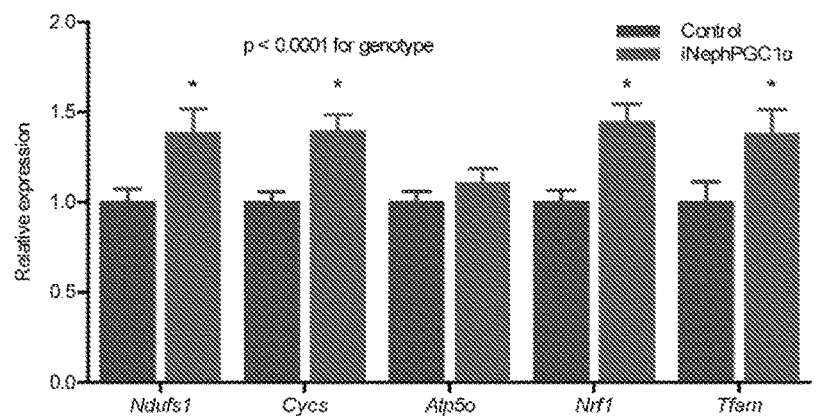
*FIG. 8E*  *FIG. 8F*
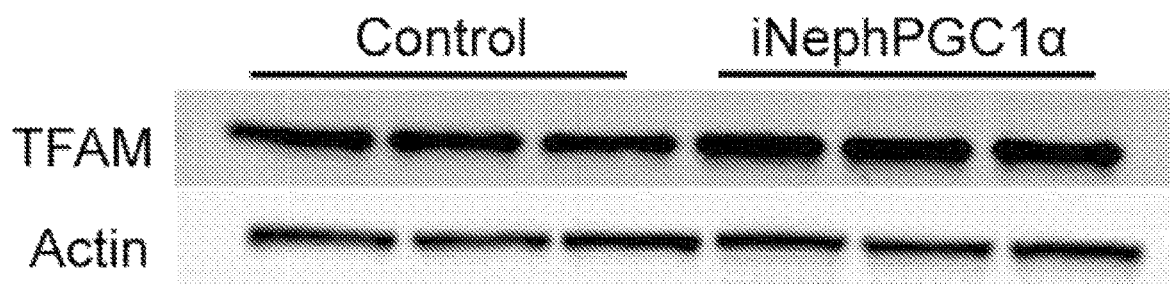
*FIG. 8G*
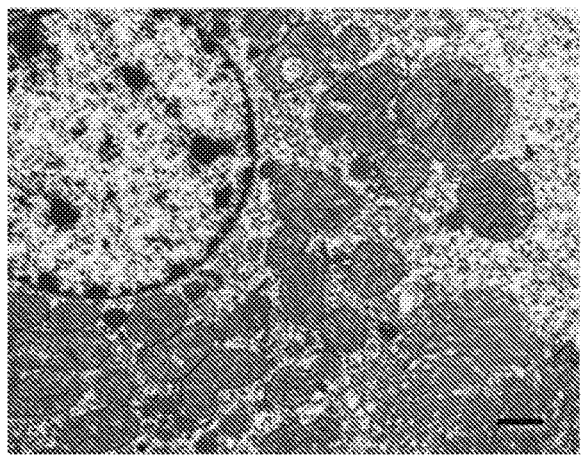 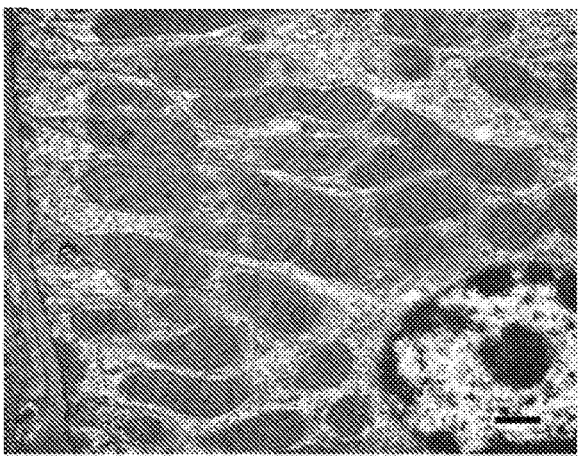
*FIG. 8H*  *FIG. 8I*

FIG. 12A
WT
FIG. 12B
KO
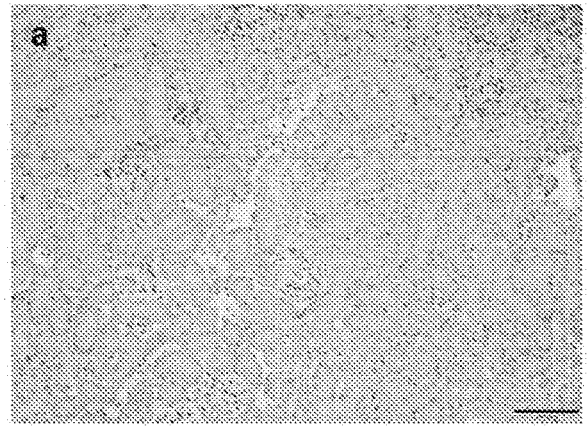
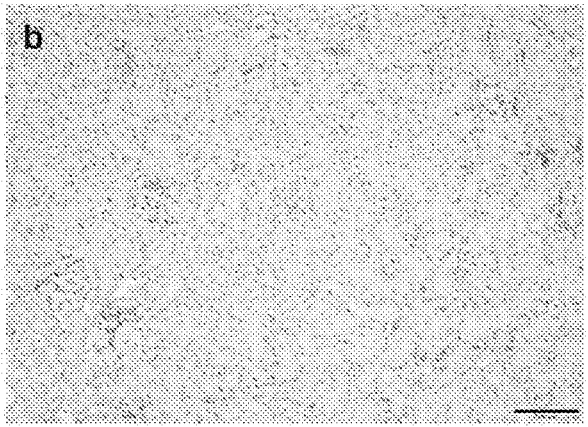
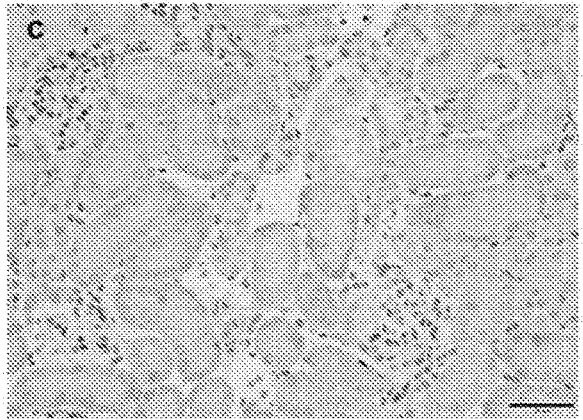
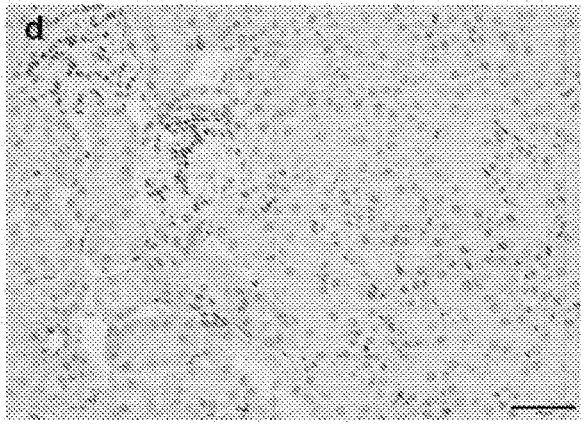
FIG. 12C
FIG. 12D
PGC1α
PGC1α and peptide
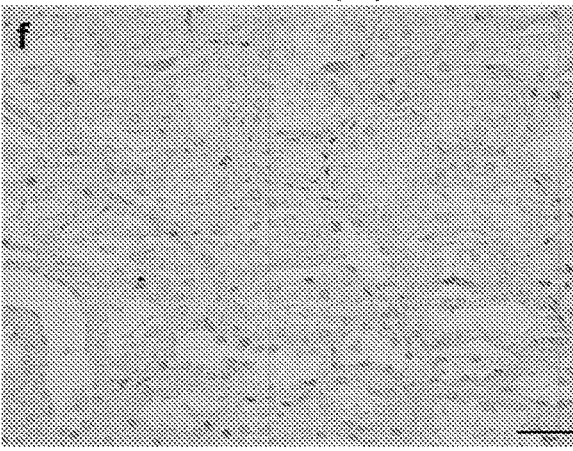
FIG. 12E
FIG. 12F

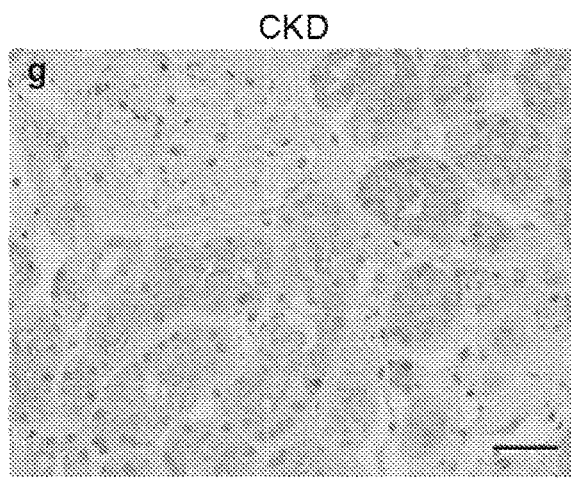
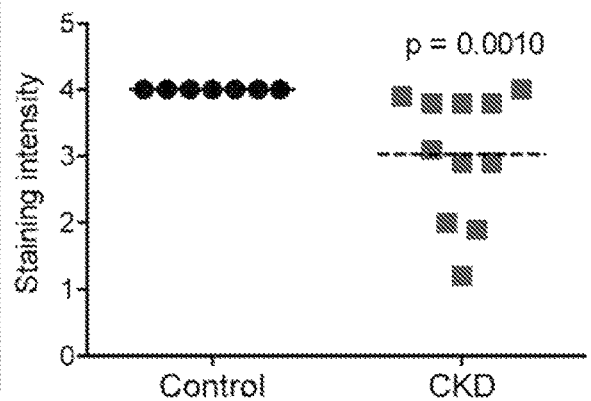
FIG. 12G　　　　　FIG. 12H
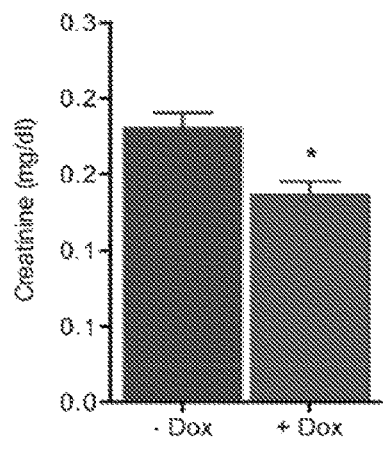
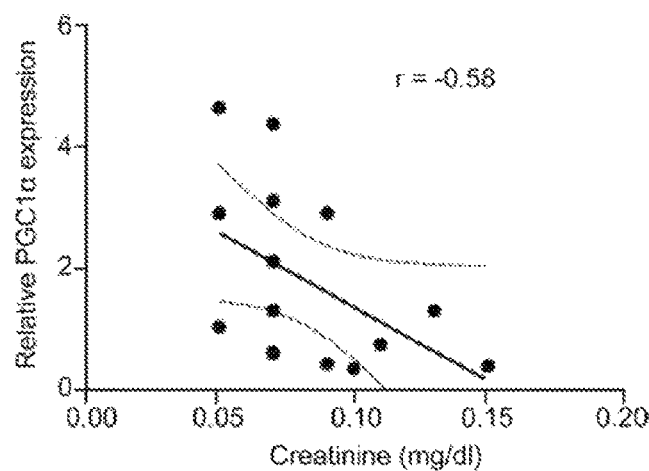
FIG. 13A　　　　　FIG. 13B
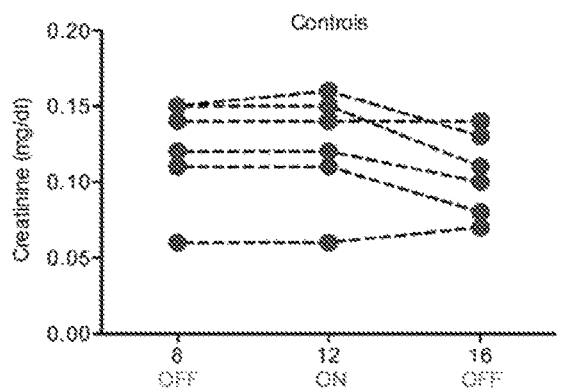
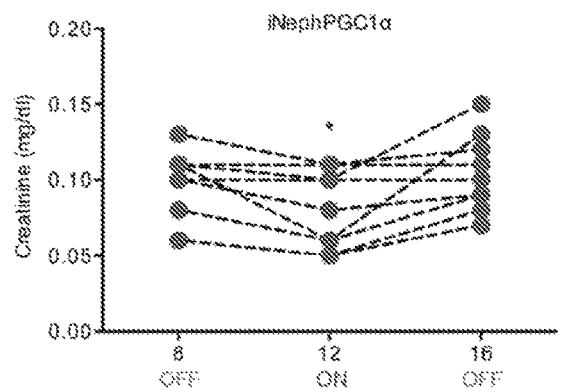
FIG. 13C　　　　　FIG. 13D PGC1α staining score = 4

PGC1α staining score = 1

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: PGC1a peptide immunogen
```

```
<400> SEQUENCE: 1

Ser Lys Tyr Asp Ser Leu Asp Phe Asp Ser Leu Leu Lys Glu Ala Gln
1               5                   10                  15

Arg Ser Leu Arg Arg
            20
```

NIACINAMIDE (NAM) IN ISCHEMIC TISSUE INJURY

CROSS-REFERENCE TO RELATED APPLICATIONS

This application is a U.S. National Phase Application under 35 U.S.C. § 371 of International Patent Application No. PCT/US2017/018682, filed on Feb. 21, 2017, which claims the benefit of U.S. Provisional Application Ser. No. 62/300,696, filed on Feb. 26, 2016, and 62/432,458, filed on Dec. 9, 2016. The entire contents of the foregoing are incorporated herein by reference.

FEDERALLY SPONSORED RESEARCH OR DEVELOPMENT

This invention was made with Government support under Grant No. DK095072 awarded by the National Institutes of Health. The Government has certain rights in the invention.

TECHNICAL FIELD

Described herein are methods of treating ischemic tissue injury or kidney disease e.g., delayed graft function that include administering a Nicotinamide adenine dinucleotide (NAD)/niacinamide (NAM) pathway agonist.

BACKGROUND

The energetic burden of continuously concentrating solutes against gradients along the tubule may render the kidney especially vulnerable to ischemia. Indeed, acute kidney injury (AKI) affects 3% of all hospitalized patients (Thadhani et al. N Engl J Med 1996; 334:1448-60; Lewington et al. Kidney Int 2013; 84:457-67).

SUMMARY

As shown herein, the mitochondrial biogenesis regulator, PGC1α (Puigserver et al. Cell 1998; 92:829-39; Ruas et al. Cell 2012; 151:1319-31), is a pivotal determinant of renal recovery from injury by regulating NAD biosynthesis. Following renal ischemia, PGC1α$^{-/-}$ mice developed local deficiency of the NAD precursor niacinamide (Nam), marked fat accumulation, and failure to re-establish normal function. Remarkably, exogenous Nam improved local NAD levels, fat accumulation, and renal function in post-ischemic PGC1α$^{-/-}$ mice. Inducible tubular transgenic mice (iNephPGC1α) recapitulated the effects of Nam supplementation, including more local NAD and less fat accumulation with better renal function after ischemia. PGC1α coordinately upregulated the enzymes that synthesize NAD de novo from amino acids whereas PGC1α deficiency or AKI attenuated the de novo pathway. Nam enhanced NAD via the enzyme NAMPT and augmented production of the fat breakdown product beta-hydroxybutyrate (β-OHB), leading to increased prostaglandin PGE$_2$, a secreted autocoid that maintains renal function (Hanson et al J Clin Invest 2010; 120:2910-9). Nam treatment reversed established ischemic AKI and also prevented AKI in an unrelated toxic model. Inhibition of β-OHB signaling or prostaglandins similarly abolished PGC1α-dependent renoprotection. Given the importance of mitochondrial health in aging and the function of metabolically active organs, the results implicate Nam and NAD as key effectors for achieving PGC1α-dependent stress resistance.

Thus provided herein are methods for treating, or reducing risk of developing, kidney disease, e.g., acute kidney injury, in a subject; the methods include administering to the subject a therapeutically effective amount of a Nicotinamide adenine dinucleotide (NAD)/niacinamide (NAM) pathway agonist. In some embodiments, the AKI is or results in delayed graft function after transplant.

Also provided herein are methods for treating, or reducing risk of developing, ischemic tissue injury in a subject, e.g., acute kidney injury; ischemic stroke; or myocardial infarction; the methods include administering to the subject a therapeutically effective amount of a Nicotinamide adenine dinucleotide (NAD)/niacinamide (NAM) pathway agonist.

Also provided herein are methods for treating, or reducing risk of developing, delayed graft function in a recipient subject and promoting organ recovery. The methods include administering a therapeutically effective amount of a Nicotinamide adenine dinucleotide (NAD)/niacinamide (NAM) pathway agonist or other NAD+ boosting strategies (1) to the donor subject or donor organs, (2) to the recipient subject and/or (3) into the preservation solutions. In some embodiments, the organ-graft is a metabolically active transplanted organ, comprising but not limited to kidney, heart, liver, and lungs.

In some embodiments, the NAD/NAM pathway agonist is Nicotinamide adenine dinucleotide (NAD); niacinamide (NAM) itself; nicotinamide mononucleotide (NMN); Nicotinamide riboside (NR); and P7C3 and analogs thereof, e.g., P7C3-A20.

In some embodiments, the NAD/NAM pathway agonist is a N'-Nicotinamide Methyltransferase (NNMT) inhibitor.

In some embodiments, the NNMT inhibitor is an inhibitory nucleic acid that specifically targets an NNMT nucleic acid, or 1-me-Nam or an analog thereof.

In some embodiments, the inhibitory nucleic acid is an antisense oligonucleotide or small interfering siRNA specifically targeting NNMT. In some embodiments, the inhibitory nucleic acid is modified, e.g., includes one or more locked nucleotides.

In some embodiments, the subject does not yet have AKI, but has been or will be hospitalized.

In some embodiments, the subject has had or is at risk of developing an ischemic injury, e.g., an ischemic brain, cardiac, or renal injury. In some embodiments the risk is imminent, e.g., will occur within months, weeks, or days, or the subject has a risk level above that of the general population, e.g., has one or more identified risk factors for an ischemic injury. In some embodiments, the subject has been or will be administered or exposed to a renal toxin, e.g., a therapeutic agent with renal toxicity, e.g., cisplatin.

In some embodiments, the subject has a chronic condition of the brain, kidney, or heart, e.g., chronic kidney disease (e.g., diabetic kidney disease, hypertensive nephropathy, FSGS, or ischemic nephropathy); forms of chronic heart disease (e.g., left ventricular hypertrophy, ischemic cardiomyopathy, or non-ischemic cardiomyopathy); and forms of chronic cerebral disease (e.g., multi-infarct dementia, Alzheimer's disease, or Parkinson's Lewy body dementia.

Also provided herein are methods for diagnosing kidney disease, or determining risk of developing risk of kidney disease, in a subject. The methods include obtaining a sample comprising urine from the subject; evaluating a level of one, two, or all three of Kyn, Kyu, and/or Quin in the sample; optionally normalizing the level of Kyn, Kyu, and/or Quin to another metabolite present in the urine sample, e.g., Trp; comparing the level of Kyn, Kyu, and/or Quin with one or more references; and determining that a subject who has a level of Kyn, Kyu, and/or Quin above the reference level has or is at risk of developing kidney disease. In some embodiments, alternatively or in addition to the metabolites mentioned above, the methods include determining one or more of a level of a NAM metabolite selected from the group consisting of Nam, methyl-Nam, Anthranilate, hydroxy-anthranilate, Xanthurenate, and Picolinate; optionally normalizing the level of the NAM metabolite to another metabolite present in the urine sample, e.g., Trp; comparing the level of the NAM metabolite with one or more references; and determining that a subject who has a level of the selected metabolite above the reference level has or is at risk of developing kidney disease.

In some embodiments, the reference is a control reference that represents a normal level of one, two, or all three of Kyn, Kyu, and/or Quin, e.g., a level in an unaffected subject who does not have and is not at risk of developing kidney disease, and/or a disease reference that represents a level of the proteins associated with kidney disease, e.g., a level in a subject having or at risk of developing kidney disease, e.g., AKI or CKD.

In some embodiments, the methods include administering to the subject a NAD/NAM pathway agonist as described herein.

In some embodiments, the subject does not yet have delayed graft function, but has had a transplant.

In some embodiments, the subject has or is at risk of developing delayed graft function.

In some embodiments, the transplanted organ is a metabolically active organ, e.g., heart, liver, or lungs.

Also provided herein are methods for diagnosing delayed graft function, or determining risk of developing risk of delayed graft function, in a subject. The methods include obtaining a sample comprising a biopsy from the transplanted organ in the subject; determining a level of PGC1α in the sample, e.g., by immunostaining the tissue biopsy, or a non-invasive surrogate thereof (e.g., the measurement of mitochondrial DNA integrity in urine, mitochondrial DNA abundance in urine, and the metabolites (e.g., quinolinate or tryptophan, as described herein); comparing the PGC1α level with a reference level; determining that a subject who has a PGC1α level below the reference level has or is at risk of developing delayed graft function; and optionally administering to a subject who has a PGC1α level below the reference level a therapeutically effective amount of a Nicotinamide adenine dinucleotide (NAD)/niacinamide (NAM) pathway agonist. In some embodiments, the reference is a control reference that represents a normal PGC1α immunostaining score e.g., a PGC1α immunostaining score in a subject who does not have and is not at risk of developing delayed graft function, and/or a disease reference that represents PGC1α immunostaining score associated with delayed graft function, e.g., a level in a subject having or at risk of developing delayed graft function.

Also provided herein are methods for predicting time to recovery or imminent recovery when a subject's organ graft does not initially function after transplant, or for predicting long-term function of an organ graft in a subject whose organ graft does not initially function after transplant. The methods include obtaining a sample comprising a biopsy from the transplanted organ in the subject; determining a level of PGC1α in the sample, e.g., by performing PGC1α immunostaining on the tissue biopsy; optionally normalizing the PGC1α level to a level of PGC1α in another tissue biopsy of the patient, e.g., a tissue biopsy taken at an earlier time point; comparing the PGC1α level with one or more reference levels; and determining that a subject who has a PGC1α score above the reference score has or is at eligible for aggression reduction of dialysis dose and more rapid hospital discharge. Alternatively, if a subject exhibits persistent delayed graft function, the methods provided herein may suffice to rule out other causes of graft non-function, such as organ rejection. For example, reduced PGC1α expression could provide reassurance to treating physicians that the cause of ongoing graft dysfunction is persistence of ischemic injury rather than new-onset of organ rejection. In some embodiments, the method is used to predict time of recovery, e.g. delayed recovery or non-delayed recovery in a subject having or at risk of developing delayed graft function. Delayed recovery is defined as a time frame of greater than or equal to 7 days post transplantation to achieve dialysis independence and a serum creatinine <2.0 mg/dl, and non-delayed recovery is defined as dialysis independence and a serum creatinine <2.0 mg/dl within a time frame less than or equal to 7 days.

In some embodiments, as an alternative to measurement of PGC1α in a biopsy sample, a non-invasive surrogate is used. the non-invasive surrogate is blood, cerebrospinal fluid, or urine, and the method comprises determining levels of metabolities that are indicative of PGC1α-NAD status, e.g., methods of non-invasive assessment: (1) the quinolinate, tryptophan and other metabolite ratios in the sample, e.g., in urine from humans with AKI; (2) urinary mitochondrial DNA abundance from people with ischemic injury, e.g., kidney injury vs. those without; and (3) mitochondrial DNA integrity reduced after ischemic injury, e.g., kidney injury, assayed in blood, cerebrospinal fluid, or urine.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 4A-H: PGC1α effectors, Nam as therapy, and PGC1α in human AKI. A, Serum creatinine in iNephPGC1α mice 24 h after IRI with vehicle vs. mepenzolate (MPN, 10 mg/kg IP) treatment (n=6/group). B, Serum creatinine in iNephPGC1α mice 24 h after IRI with vehicle vs. indomethacin (INDO, 10 mg/kg IP) treatment (n=6/group). C, Serial serum creatinine levels in mice receiving a single dose of Nam (400 mg/kg IP) 18 h after the onset of reperfusion, i.e., with established AKI. Analyzed by ANOVA (n=5/group). Kidney function as measured by serum creatinine (SCr) rapidly improved in Nam-treated animals. Analyzed by ANOVA (n=5/group); p=0.0013. D, Serial serum creatinine levels after cisplatin (25 mg/kg IP administered on day 0) with or without Nam (400 mg/kg IP on day −1 and day 0). Analyzed with Bonferroni-corrected ANOVA (n=5/group). E, Relative renal Nam from D. F,G, Representative immunostaining (brown) for PGC1α from control human kidney and a renal biopsy for AKI. Scale bars 50 µm. H, PGC1α immunostaining intensity (1=weakest, 4=strongest). Each dot represents a unique specimen. Analyzed by Mann-Whitney. Error bars SEM, *p<0.05, p<0.01, **p<0.0001.

FIGS. 5A-F: Regulation of PGC1α and other features of post-ischemic kidneys. A, Serum creatinine 24 h after sham or IRI (n=5 vs. 14 mice), *p<0.001. B, Absence of classwide changes in intrarenal phospholipids 24 h after IRI vs. sham operation (n=6/group, NS=non-significant). Each bar represents one lipid species. P-value by two-way ANOVA. C, Renal PGC1α expression 24 h after sham or IRI (n=5 animals per group), p<0.01. D, Correlation of LC-MS method for serum creatinine and serum cystatin C (measured by ELISA). E, Glomerular filtration rate in controls or 24 h after IRI was determined by two-phase exponential decay curves of fluorescently-labeled inulin as described in methods (n=5/group), *p<0.05. F, Correlation of LC-MS method for serum creatinine with clearance of FITC-inulin. Curve fit according to formula sCr=κ/GFR where κ is a constant. Error bars SEM.

FIGS. 6A-G: Exacerbation of fat accumulation and tubular injury in post-ischemic PGC1α$^{-/-}$ kidneys. A-D, Low (A,B) and high-power (C,D) photomicrographs 24 h after IRI in WT vs. PGC1α$^{-/-}$ (KO) mice. Scale bars 100 and 50 µm. E,F, Blinded scoring of tubular injury in cortex and outer stripe of outer medulla (OSOM) on 4-point injury scale as described in Methods (n=8 WT vs. 12 KO mice), *p<0.05. G, Di-/tri-acylglycerols (DAGs, TAGs) in renal homogenates of KO mice at baseline and 24 h after injury (n=6/group). Each bar represents one lipid species. P-value by two-way ANOVA. Error bars SEM.

FIGS. 8A-K: Increased mitochondrial abundance and post-ischemic protection in renal tubular epithelial transgenic mice (iNephPGC1α). A, Schematic for generating iNephPGC1α mice. B, Relative renal PGC1α expression in controls vs. iNephPGC1α mice with and without 4 weeks of doxycycline in drinking water (n=5/group, **p<0.01 vs. all other groups). C, Ratio of kidney weight to total body weight (note body weights statistically indistinguishable as well, n=4/group). D, Example gross images with 1 cm scale of control vs. iNephPGC1α kidney. E, Renal mitochondrial DNA (mtDNA) copy number as described in Methods. F, Relative renal gene expression of PGC1α targets (Ndufs1, Cycs, Atp5o), partnering transcription factors (Nrf1), and the mitochondrial transcription factor, TFAM. Results analyzed by two-way ANOVA with p-value for genotype as noted. N=8/group. *p<0.05 vs. control after Bonferroni correction. G, Western analysis of kidney lysates for Transcription Factor A, Mitochondrial (TFAM) (Kang and Ji, J Appl Physiol (1985) 115, 1618-1625 (2013)) and loading control. H,I, Transmission EM of mitochondria sectioned perpendicular and parallel to long axis demonstrating normal morphology in iNephPGC1α mice (representative of n=4/group), scale bar 500 nm. J,K, Blinded scoring of tubular injury in cortex and outer stripe of outer medulla (n=8 control; 12 iNephPGC1α). Error bars SEM, *$p<0.05$, **$p<0.01$.

FIGS. 12A-H: Renal immunostaining for PGC1α declines in human chronic kidney disease A-D, Low (A,B) and high-power (C,D) photomicrographs of PGC1α immunoreactivity (brown) in wildtype littermates (WT) and PGC1α$^{-/-}$ (KO) kidneys. Scale bars 100 and 50 μm. E,F Representative results of peptide competition attenuating PGC1α immunoreactivity against human kidney (n=4) as described in Methods. G, Representative immunostaining (brown) for PGC1α in a renal biopsy with chronic kidney disease (CKD). Scale bar 50 μm. H, Results of scoring PGC1α immunostaining intensity (1=weakest, 4=strongest) in specimens with CKD by blinded operator. Each dot represents a unique specimen. Analyzed by Mann-Whitney.

FIGS. 13A-L: Evidence for renal-tubular-epithelial-PGC1α-dependent reversible vascular relaxation. A, Serum creatinine in uninduced (−Dox) vs. induced (+Dox) iNephPGC1α mice (n=8-10 mice per group). B, Comparison of serum creatinine with degree of renal PGC1α expression, $p<0.05$. C,D Serial serum creatinines in iNephPGC1α mice vs. controls before PGC1α induction (OFF), after 4 weeks of PGC1α induction (ON), and after 4 weeks of washout (OFF), *$p<0.05$ by repeated measures ANOVA. E-G, Comparison of serum creatinine at different time points with renal artery flow in iNephPGC1α mice from D, $p<0.05$ when correlation coefficient $r=-0.65$. H-J, Comparison of resistive index with renal artery flow volume in iNephPGC1α mice from D, $p<0.05$ when correlation coefficient $r=-0.80$. K, Circulating thyroxine levels in iNephPGC1α mice with and without gene induction (n=5/group) to rule out Pax8-related thyrotoxicosis driving perfusion differences as previously described (Antonica, F., et al. Generation of functional thyroid from embryonic stem cells. Nature 491, 66-71 (2012)). L, Relative renal expression for VEGF in PGC1α$^{-/-}$ mice (KO) vs. WT littermates (n=6/group). Error bars SEM.

DETAILED DESCRIPTION

NAD has long been recognized for its central role in energy metabolism, with recent work demonstrating that NAD is rate-limiting for mitochondrial function (Bai et al. Cell Metab 2011; 13:461-8). NAD augmentation appears to restore youthful mitochondrial function and reverse age-related declines in health (Gomes et al. Cell 2013; 155:1624-38). In contrast, NAD depletion has been described as a feature of diabetes (Garcia Soriano et al. Nat Med 2001; 7:108-13). Since diabetes and aging are two of the most prevalent predispositions for AKI, the present results motivate interest in whether local NAD concentration may provide a setpoint for resistance to acute renal stressors. NAD may also be important for the gradual decline of kidney function with normal aging.

That an even larger set of known AKI risk factors—including diabetes, but also chronic kidney disease (FIGS.

12G,H), sepsis, and warm ischemia—is associated with reduction of PGC1α (Tran et al. J Clin Invest 2011; 121: 4003-14; Vafai et al. Nature 2012; 491:374-83) further attests to the potential relevance of the results to human disease. Experiments targeting mitochondrial biogenesis through a drug-screening approach offer additional promise for this avenue in AKI (Jesinkey et al. J Am Soc Nephrol 2014; 25:1157-62). Since AKI has been associated with death in critically ill patients, (Thadhani et al. N Engl J Med 1996; 334:1448-60) that excess renal PGC1α improves survival after AKI highlights the importance of the kidney to overall health. Downstream of PGC1α, Nam may not only be an effective preventative agent, but also a potential therapy for established AKI, a set of diseases for which no drug has yet been identified.

PGC1α in skeletal muscle has been shown to exert extracellular effects, whether through the myokine irisin, metabolites such as kynurenine, or the angiogenic factor VEGF (Arany et al. Nature 2008; 451:1008-12; Bostrom et al. Nature 2012; 481:463-8; Agudelo et al. Cell 2014; 159:33-45). By comparison, the present results show that renal tubular PGC1α communicates with neighboring cells at least through $PGE_2$. Therapeutic manipulation of renal β-OHB may constitute one means of increasing $PGE_2$. $PGE_2$ is a well-recognized vasodilator in the kidney, but may also be exerting cytoprotective effects in AKI (reviewed in Breyer et al. J Am Soc Nephrol 1996; 7:8-17), actions that have been demonstrated in multiple animal models and even humans (Papanicolaou et al. Clinical science and molecular medicine 1975; 49:507-10; Mauk et al. Kidney Int 1977; 12:122-30; Sketch et al. American journal of therapeutics 2001; 8:155-62).

Figure 13E:
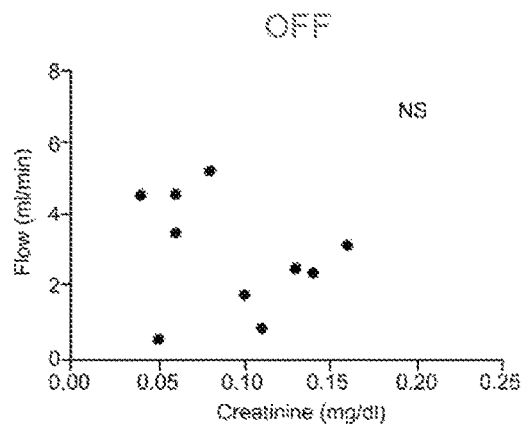
Figure 13F:
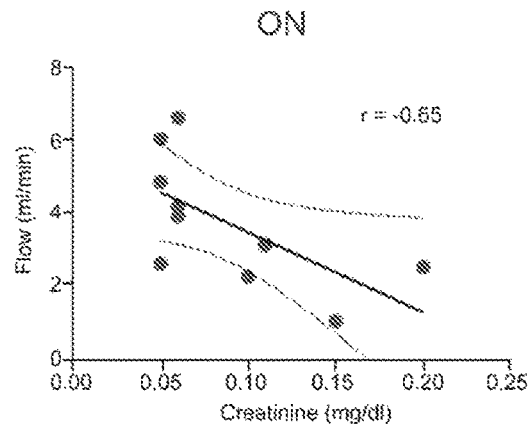
Figure 13G:
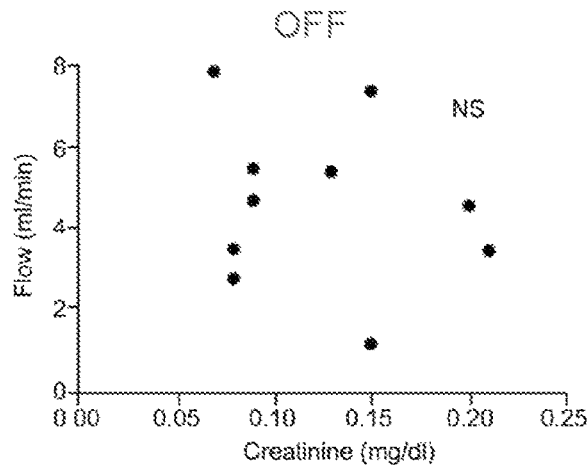
Figure 13H:
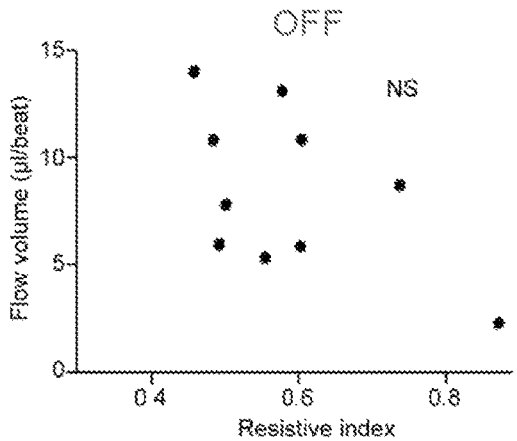
Figure 13I:
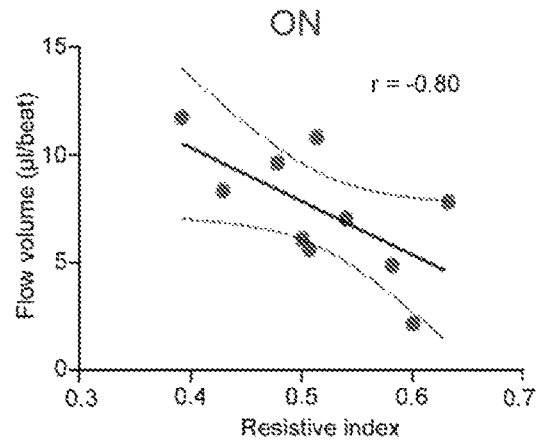
Figure 13J:
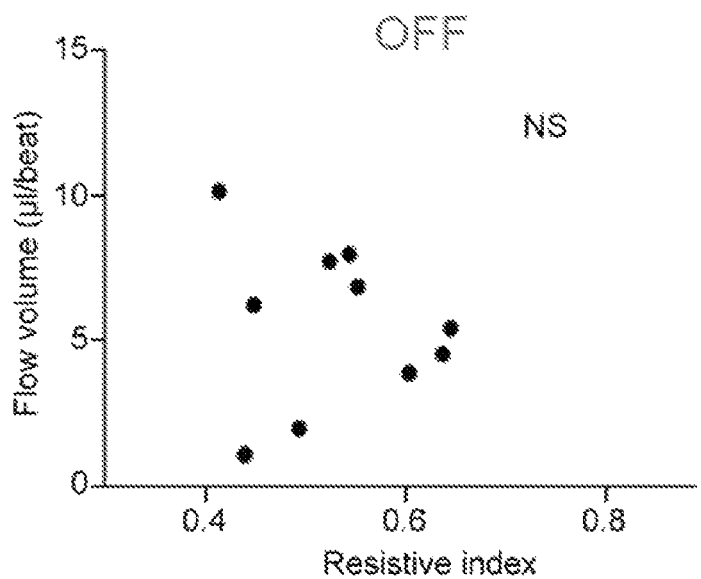
Figure 13K:
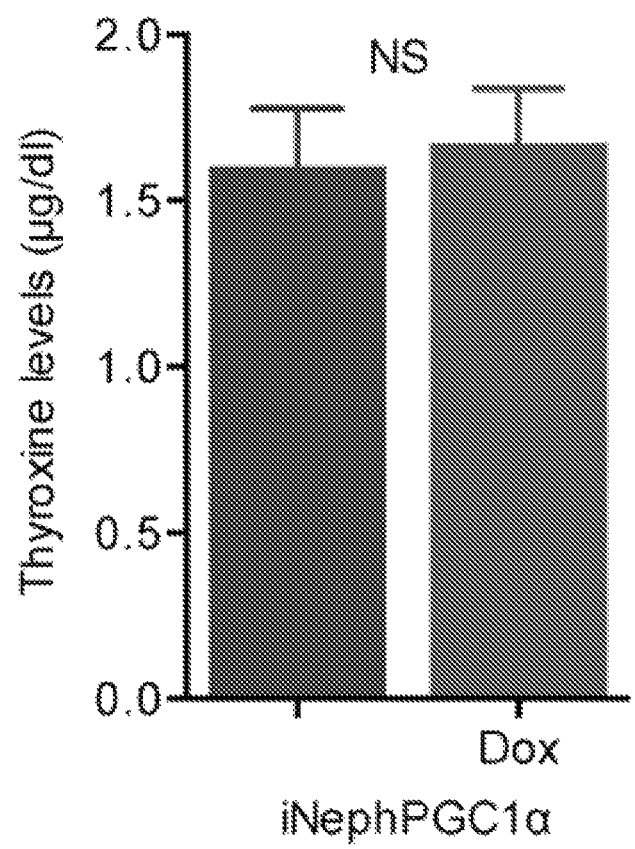
Figure 13L:
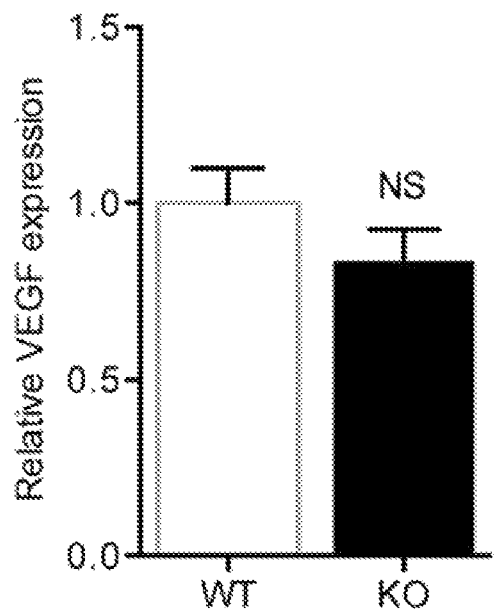

Enhanced renal function, vascular relaxation, and increased perfusion at baseline were observed as a result of excess PGC1α in the epithelial compartment of the kidney in the iNephPGC1α model (FIGS. 13A-J), physiological features that would be consistent with functional responses of the local vasculature to the excess renal $PGE_2$ present in this model. However, experiments were also performed to determine whether VEGF was regulated by renal PGC1α as such features could also arise from increased vascularization (FIGS. 13K-L). PGC1α$^{-/-}$ mice showed no decrement in renal VEGF and iNephPGC1α mice displayed only modest induction vs. their respective controls. This strongly contrasts with VEGF induction by skeletal muscle PGC1α, (Arany et al. Nature 2008; 451:1008-12) suggesting the presence of cell-specific modulators of PGC1α function such as ERRα, which is notably more abundant in skeletal muscle than kidney (biogps.org, Wu et al., Nucl. Acids Res. 44 (D1): D313-D316 (2016)).

In addition, the coordinated regulation of NAD biosynthesis by PGC1α may occur in other cells and organs, particularly under stress conditions. As shown herein, loss of PGC1α affects NAD levels in brain and cardiac tissues as well. Thus, the present methods are applicable in those organs as well as kidney.

Figure 14:
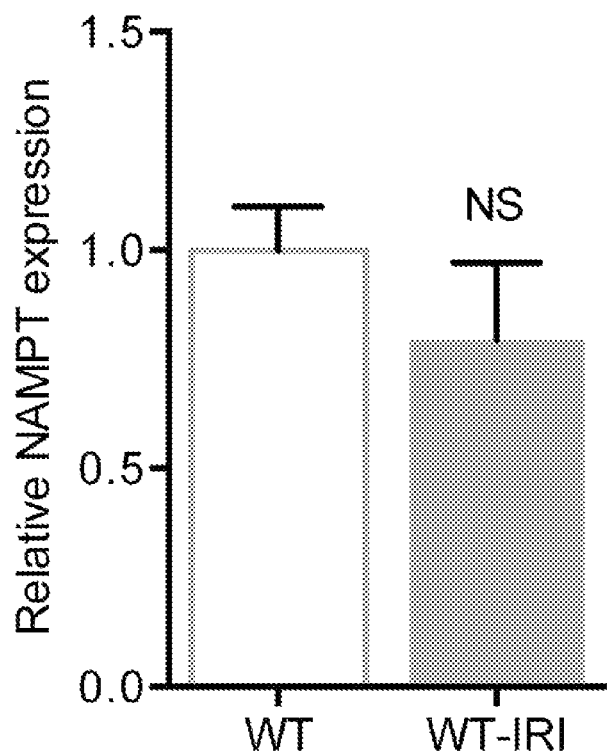
FIG. 14: Relative renal expression for NAMPT in wild-type mice before and 24 h after IRI (n=6/group). Error bars SEM.

The transcription factor(s) with which PGC1α interacts to induce the de novo pathway are of substantial interest. Since ischemia did not reduce renal NAMPT (FIG. 14), the salvage pathway may be a viable therapeutic route. Second, the rapid reduction of NAD during AKI may also relate to its already short half-life (Feldkamp et al. Am J Physiol Renal Physiol 2004; 286: F749-59) as well as the action of NAD-consuming enzymes such as PARPs, nucleotidases, and sirtuins, all of which have been implicated in this condition (Morigi et al. J Clin Invest 2015; 125:715-26; Ebrahimkhani et al. Proc Natl Acad Sci USA 2014; 111: E4878-86; Rajakumar et al. Transplantation 2010; 90:1260-4). Third, NAD's emerging role as a guardian against age-related decline in health and mitochondrial function (Gomes et al. Cell 2013; 155:1624-38) suggests that therapeutic manipulation of Nam and NAD may have implications beyond AKI. For example, NAMPT agonism protects against experimental neuronal injury (Wang et al. Cell 2014; 158:1324-34). And inhibition of urinary Nam disposal (by blocking N-methylation) prevents experimental obesity (Kraus et al. Nature 2014; 508:258-62). Finally, the link from mitochondrial metabolism to renoprotective prostaglandins unites two major avenues of mechanistic investigation in AKI, but other mediators and downstream effectors for renal PGC1α may also exist.

In summary, the present work applies complementary discovery approaches to identify a new pathway by which parenchymal PGC1α affects NAD to protect against renal injury. The results may have mechanistic, diagnostic, and therapeutic implications in the kidney and beyond.

Methods of Treatment

As shown herein, acute kidney injury (AKI) is characterized by a widespread metabolic deficit. Using a combination of RNA-sequencing approaches and metabolomics, the present inventors identified a critical deficiency within the kidney of the energy carrier NAD (niacinamide adenine dinucleotide). In addition, NAD deficiency exacerbates renal and cardiac injury after ischemia.

NAD is responsible for accepting hydride ions as various energy fuels, e.g., fats, amino acids, and carbohydrates, are oxidized in the cell. In turn, the reduced form of NAD, called NADH, "carries" the energy of fuel oxidation to the electron transport chain of the mitochondria, where it is harnessed to generate ATP.

A shortage of NAD in an injured organ, e.g., heart or kidney results in poor energy utilization, mitochondrial dysfunction, and ultimately, cell death. As shown herein, administration of niacinamide (Nam), a form of vitamin B3, can replenish the levels of NAD within the injured organ (e.g., kidney or heart), facilitate fat oxidation, and ultimately, protect renal function. Critically, Nam administration: (1) prevents experimental ischemic renal or cardiac injury; (2) treats established experimental ischemic renal injury when given after the onset of injury; (3) treats an unrelated form of kidney injury, induced by the chemotherapy drug cisplatin; and (4) bolsters the local production of a renoprotective prostaglandin called PGE2. The present results strongly suggest both broad applicability in kidney disease and novel mechanism of improving kidney health.

Described herein are methods that include measuring and/or manipulating the NAD pathway for diagnosis, monitoring, and therapeutic benefit.

The methods described herein include methods for the treatment or prophylaxis (reduction of risk of developing) of tissue ischemic injury and/or kidney disease, e.g., chronic kidney disease (CKD) or acute kidney injury (AKI). As used herein, kidney disease refers to non-cancerous disease, i.e., does not include kidney cancer, e.g., does not include renal carcinoma. In some embodiments, the subject is hospitalized; AKI is a very common hospital diagnosis and can occur at the onset of hospitalization or at any time during the hospitalized period. In some embodiments, the subject has AKI or an AKI diagnosis, e.g., acute ischemic injury, post-transplant delayed graft function attributable to ischemia-reperfusion injury, acute nephrotoxic injury (from medications, heme pigments, or toxic ingestions), pre-renal states such as volume depletion or sepsis, septic tubular injury, hepatorenal syndrome, cardiorenal syndrome, or acute interstitial nephritis. In some embodiments, the subject has CKD or a CKD diagnosis, e.g., primary or secondary focal segmental glomerulosclerosis (the latter category includes diabetic kidney disease, hypertensive kidney disease, obesity-related kidney disease), chronic allograft nephropathy, chronic lupus nephritis, chronic interstitial nephritis, or chronic IgA nephropathy. In some embodiments, the methods include identifying a subject as at risk of developing CKD or AKI based on a method described herein (e.g., based on levels of a biomarker described herein). Alternatively, a subject can be diagnosed with kidney disease, e.g., AKI, using methods known in the art, e.g., based on the presence of a blood urea nitrogen (BUN) level of greater than 20; the presence of Glomerular Filtration Rate (GFR) of below 90, or below 60; or a serum creatinine (SCr) level greater than 1.2 for women and greater than 1.4 for men. In some embodiments, the subject can be one who has had an ischemic tissue injury, e.g., to the brain, heart, or kidney, or who has been or will be administered or exposed to a toxin, e.g., a renal toxin, such as cisplatin, carboplatin, nitrosureas such as carmustine (BiCNU, BCNU), mitomycin, and methotrexate (especially if high doses are used), or any other renal toxin, e.g., antimicrobials such as aminoglycoside drugs (gentamicin, tobramycin, etc.); antifungals such as amphotericin; anti-pneumocytis agents such as pentamidine; iodinated radiocontrast (intravenous or intraarterial) is probably the most widely used renal toxin; other chemotherapies such as carboplatin; anti-inflammatory medications such as acetaminophen (Tyelnol, etc.), NSAIDS (Advil, etc.), and COX-inhibitors (Vioxx, etc.); toxic non-medication ingestions that can harm the kidneys such as cocaine or antifreeze; or endogenous toxins such as heme pigments coming from crush injuries to skeletal muscle (so-called rhabdomyolysis).

In some embodiments the subject has had, or is about to have, an organ transplant, e.g., a kidney, heart, liver, lungs, or limb (skeletal muscle) transplant. Delayed graft function (DGF) affects ~30% of all kidneys implanted to recipients that have been harvested from deceased donors. Since deceased donors are the chief source of transplantable organs, this is a major problem. As shown herein, kidney expression of the mitochondrial biogenesis regulator PGC1α predicts the timing the recovery among those with DGF. Given the preclinical data that less PGC1α in the kidney sensitizes the host to noxious stimuli whereas more PGC1α in the kidney protects the host from developing injury in response to the same noxious stimuli, the human findings suggest a biologically plausible therapeutic path to achieving better acute transplant outcomes. Strategies that boost PGC1α levels or levels of its downstream effector, the energy carrier NAD+, may be applicable in the donor, the preservation solution, and/or the recipient. Since DGF is associated with poor long-term outcomes, therapeutic strategies could also impact the lifespan of the transplanted kidney. The same metabolic protection pathway through PGC1α and NAD+ may be applicable in other metabolically active transplanted organs such as the kidney, heart, liver, lungs, and limbs (skeletal muscle).

In some embodiments, wherein the method is for treating an AKI, to "treat" means to ameliorate at least one symptom of the AKI. Often, AKI results in a reduction in Glomerular filtration rate (GFR); thus, a treatment can result in an increase in GFR and a return or approach to normal kidney function. Administration of a therapeutically effective amount of a compound described herein for the treatment of AKI can result in improved kidney function, e.g., improved renal blood flow, decreased sCr, decreased BUN, or increased GFR.

Alternatively, where the treatment is administered to a subject who has had an ischemic tissue injury, e.g., to the brain, heart, or kidney, the treatment can reduce the long-term effects of the ischemic event, e.g., by reducing infarct size or reducing recovery time.

In embodiment, wherein the subject has been or will be administered or exposed to a toxic agent, e.g., a renal toxin as known in the art as described herein, the methods can reduce the toxicity of the agent, e.g., prevent or reducing the toxic effects of the agent (see, e.g., Mukhopadhyay et al., Free Radic Biol Med. 53(5): 1123-38 (2012); Zsengeller et al., J Histochem Cytochem. 60(7):521-9. (2012). In the case of a therapeutic agent that exhibits renal toxicity, the methods described herein can include co-administration (e.g., substantially concurrent (at the same time) or subsequent (one after the other) administration) of the therapeutic agent and a NAD/NAM pathway agonist as described herein.

In some embodiments, treatment is administered for the duration of AKI itself, which typically lasts 2 days-2 weeks. In some embodiments, when used as a preventative agent, the treatment is administered for the entire period of risk—for example, when a patient (such as a heart failure patient) is admitted (e.g., to remove fluid from the body with diuretics), the entire period of that admission places the patient at risk for AKI because removing fluid can induce or contribute to AKI.

In some embodiments, the methods are used to treat or reduce the risk of chronic conditions of the brain, kidney, or heart. The connection from PGC1alpha to NAD as described herein indicates that the methods can be used to reverse, prevent, delay, or reduce the risk of transition from acute to chronic conditions, and to treat the chronic conditions themselves. Thus, the methods can be used to treat forms of chronic kidney disease (e.g., diabetic kidney disease, hypertensive nephropathy, FSGS, ischemic nephropathy); forms of chronic heart disease (left ventricular hypertrophy, ischemic cardiomyopathy, non-ischemic cardiomyopathy); and forms of chronic cerebral disease (e.g., multi-infarct dementia, alzheimers, Parkinson's Lewy body dementia.

Generally, the methods include administering a therapeutically effective amount of a NAD pathway agonist as described herein, to a subject who is in need of, or who has been determined to be in need of, such treatment.

Methods of Diagnosing Kidney Disease

Included herein are methods for diagnosing kidney disease, and for identifying subjects who are at risk of developing kidney disease, e.g., AKI or CKD. In some embodiments, the methods rely on detection of a biological marker or a plurality of biological makers of NAD deficiency. In normal healthy subjects, the biosynthetic pathway for NAD is tryptophan (Trp)→kynurenine (Kyn)→kynurenic acid (Kyu)→quinolinate (Quin)→NAD (See also FIGS. 3C and 15B). Therefore, a failure to convert Trp to NAD in AKI results in a build-up of intermediates (Kyn, Kyu, Quin) that spills over into urine. The methods include obtaining a sample comprising urine from a subject, and evaluating the presence and/or level of one, two, or all three of Kyn, Kyu, and/or Quin in the sample (optionally normalized to another metabolite present in the urine sample, e.g., Trp), and comparing the presence and/or level with one or more references, e.g., a control reference that represents a normal level of one, two, or all three of Kyn, Kyu, and/or Quin, e.g., a level in an unaffected subject who does not have and is not at risk of developing kidney disease, and/or a disease reference that represents a level of the proteins associated with kidney disease, e.g., a level in a subject having or at risk of developing kidney disease, e.g., AKI or CKD. In some embodiments, alternatively or in addition to the metabolites mentioned above, the methods include determining one or more of a level of a NAM metabolite selected from the group consisting of Nam, methyl-Nam, Anthranilate, hydroxy-anthranilate, Xanthurenate, and Picolinate; optionally normalizing the level of the NAM metabolite to another metabolite present in the urine sample, e.g., Trp; comparing the level of the NAM metabolite with one or more references; and determining that a subject who has a level of the selected metabolite above the reference level has or is at risk of developing kidney disease. Suitable reference values can include those shown in FIG. 15A.

As used herein the term "sample", when referring to the material to be tested for the presence of a biomarker (e.g., one, two, or all three of Kyn, Kyu, and/or Quin, one or more Nam metabolite, and/or optionally Trp) using a method described herein, can include inter alia whole blood, plasma, serum, urine, cerebrospinal fluid; typically, for diagnosing kidney disease a urine sample will be used. Various methods are well known within the art for the identification and/or isolation and/or purification of the biomarker(s) from a sample. An "isolated" or "purified" biological marker is substantially free of cellular material or other contaminants from the cell or tissue source from which the biological marker is derived i.e. partially or completely altered or removed from the natural state through human intervention.

The level of the biomarker(s) (e.g., one, two, or all three of Kyn, Kyu, and/or Quin, one or more Nam metabolite, and/or optionally Trp) can be determined by any method known in the art, e.g., enzymatic assays, spectrophotometry, colorimetry, fluorometry, bacterial assays, liquid chromatography, gas chromatography, Mass spectrometry, matrix-assisted laser desorption/ionization mass spectrometry (MALDI-MS) and surface-enhanced laser desorption/ionization mass spectrometry (SELDI-MS), gas chromatography-mass spectrometry (GC-MS), liquid chromatography-mass spectrometry (LC-MS), LC-MS/MS, tandem MS, high pressure liquid chromatography (HPLC), reverse-phase HPLC, HPLC-MS, Liquid chromatography-electrospray ionization-tandem mass spectrometry (LC-ESI-MS) and nuclear magnetic resonance spectroscopy, or other known techniques for determining the presence and/or quantity of the biomarker(s); in some embodiments, the level of the biomarker(s) is determined using one of HPLC, LC-MS, HPLC-MS, LC-ESI-MS or GC-MS. See, e.g., Tarr, Biochemical Medicine, 26(3):330-338 (1981); Ravin et al., Blood 116(10): 1755-1760; Pedersen, European Heart Journal 34 (34): 2689-2696 (2013). Conventional methods include sending a clinical sample(s) to a clinical laboratory, e.g., on site or a third party contractor, e.g., a commercial laboratory, for measurement.

In some embodiments, the presence and/or level of the biomarkers (one, two, or all three of Kyn, Kyu, and/or Quin, one or more Nam metabolite, optionally normalized to Trp levels) is comparable to the presence and/or level of the biomarker(s) in the disease reference, and the subject has one or more clinical signs or symptoms associated with kidney disease, e.g., oliguria; increased SCr (e.g., at least 1.0 m/dl, or for AKI, an increased SCr of at least 2.0 mg/dl), a BUN level of greater than 20; and/or GFR of below 90, or below 60), then the subject has or can be diagnosed with kidney disease. In some embodiments, the subject has no clinical signs or symptoms of kidney disease, but the presence and/or level of one or more of the biomarkers evaluated is comparable to the presence and/or level of the protein(s) in the disease reference, and the subject is or has been hospitalized, then the subject has an increased risk of developing kidney disease, e.g., AKI. In some embodiments, once it has been determined that a person has kidney disease, e.g., AKI, or has an increased risk of developing kidney disease, e.g., AKI, then a treatment, e.g., as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of one, two, or all three of Kyn, Kyu, and/or Quin, one or more Nam metabolite, and/or optionally normalized to Trp levels, e.g., a control reference level that represents a normal level of one, two, or all three of Kyn, Kyu, and/or Quin, one or more Nam metabolite, and/or optionally normalized to Trp levels, e.g., a level in an unaffected subject or a subject who is not at risk of developing a disease described herein, and/or a disease reference that represents a level of Kyn, Kyu, and/or Quin, one or more Nam metabolite, and/or optionally normalized to Trp levels associated with conditions associated with kidney disease, e.g., a level in a subject having AKI.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have, and is not at risk of developing kidney disease (e.g. AKI). In some cases it may be desirable that the control subject is healthy, and in other cases it may be desirable that a control subject has been or is hospitalized, but does not have and does not subsequently develop kidney disease (e.g., AKI) during their hospital stay.

A disease reference subject is one who has (or has an increased risk of developing) kidney disease, e.g., AKI. An increased risk is defined as a risk above the risk of subjects in the general population.

Thus, in some cases the level of one, two, or all three of Kyn, Kyu, and/or Quin, one or more Nam metabolite, and/or optionally normalized to Trp levels, in a subject being greater than or equal to a reference level of the biomarker(s) is indicative of a clinical status (e.g., indicative of a disorder as described herein, e.g., kidney disease, e.g. AKI). In other cases, the level of the biomarker in a subject being less than the reference level is indicative of the absence of disease or normal risk of the disease. In some embodiments, the amount by which the level in the subject is the less than the reference level is sufficient to distinguish a subject from a control subject, and optionally is a statistically significantly less than the level in a control subject. As used herein, "being equal" refers to being approximately equal (e.g., not statistically different).

The predetermined value can depend upon the particular population of subjects (e.g., human subjects) selected. For example, an apparently healthy population will have a different 'normal' range of levels of Kyn, Kyu, and/or Quin, and/or one or more Nam metabolite, than will a population of subjects which have, are likely to have, or are at greater risk to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

Methods of Predicting Delayed Graft Function and Recovery Time after Kidney Transplant Typical recovery time for a newly implanted kidney is 2-4 days. Delayed graft function is often defined in clinical research as either (A) any need for dialysis after transplantation and/or (B) the persistent need for dialysis one week after transplantation (dialysis bridges the body's need for toxin removal if the new kidney does not immediately start working). When PGC1α levels are low at the time of biopsy for DGF, renal recovery appears to be delayed by ~2 weeks as shown in FIG. 20 (time needed for 50% study population to achieve renal recovery defined as dialysis independence and a serum creatinine <2.0 mg/dl). Included herein are methods for predicting delayed graft function and recovery after kidney transplant, and for identifying subjects who are at risk of developing delayed graft function. The methods rely on detection of PGC1α, a mitochondrial biogenesis regulator and important for stress resistance. As shown herein, loss of PGC1α affects NAD levels. NAMPT stimulation with P7C3 or excess NAMPT substrate Niacinamide (Nam) can boost NAD levels and may be organ-protective. In subjects who do not have and are not at risk of developing delayed graft function, PGC1α levels are elevated in tissue biopsy samples. Therefore, subjects who have delayed graft function and therefore an extended time to desist dialysis support-indicating adequate functional recovery, e.g. delayed recovery, or are at risk of developing delayed graft function and experiencing delayed recovery have lower PGC1α levels in tissue biopsy samples (See also FIGS. 19. A-B). Time to renal recovery was defined as the absence of hemodialysis and the achievement of a serum creatinine <2.0 mg/dl. As used herein any subject having or at risk of developing delayed graft function also has a delayed recovery or is at risk of developing a delayed recovery, e.g. extended time to desist dialysis support-indicating adequate functional recovery as defined herein.

The methods include obtaining a sample comprising a tissue biopsy, or a non-invasive surrogate thereof, from a subject, determining a level of PGC1α in the sample, e.g., using immunostaining; comparing the PGC1α level in the sample with one or more reference levels, e.g., a control reference that represents a normal level of PGC1α, e.g., a level in an unaffected subject who does not have and is not at risk of developing delayed graft rejection and who does not have and is not at risk of experiencing delayed recovery, and/or a disease reference that represents PGC1α level associated with delayed graft function and delayed recovery, e.g., a level in a subject having or at risk of developing delayed graft function and delayed recovery; and determining that a subject who has a PGC1α level below the reference level is at risk of developing delayed graft function delayed recovery. Suitable reference values can include those shown in FIGS. 19A-B.

As used herein the term "sample", when referring to the material to be tested for the presence of PGC1α using a method described herein, can include inter alia tissue biopsy or a non-invasive surrogate thereof, typically, for diagnosing delayed graft function a tissue biopsy sample will be used. Various methods are well known within the art for the identification of PGC1α from a sample, e.g., immunostaining. Conventional methods include sending a clinical sample (s) to a clinical laboratory, e.g., on site or a third party contractor, e.g., a commercial laboratory.

In some embodiments, the presence and/or level of PGC1α is comparable to the presence and/or level of PGC1α in the disease reference, and the subject has one or more clinical signs or symptoms associated with delayed graft function, e.g., an increased SCr of at least 2.0 mg/dl), then the subject has or can be diagnosed with delayed graft function. In some embodiments, the subject has no clinical signs or symptoms of delayed graft function, but the presence and/or level of PGC1α evaluated is comparable to the presence and/or level PGC1α in the disease reference, and the subject is or had a kidney transplant, then the subject has an increased risk of developing delayed graft function. In some embodiments, once it has been determined that a person has delayed graft function, or has an increased risk of developing delayed graft function then a treatment, e.g., as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of PGC1α, e.g., a control reference PGC1α level that represents a normal level of PGC1α, e.g., a level in an unaffected subject or a subject who is not at risk of developing delayed graft function, and/or a disease reference that represents a level of PGC1α associated with conditions associated with delayed graft function.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have, and is not at risk of developing delayed graft function. In some cases it may be desirable that the control subject is healthy, and in other cases it may be desirable that a control subject has had a kidney transplant, but does not have and does not subsequently develop delayed graft function during their hospital stay.

A disease reference subject is one who has (or has an increased risk of developing delayed graft function. An increased risk is defined as a risk above the risk of subjects in the general population.

Thus, in some cases the level of PGC1α, in a subject being less than a reference level of PGC1α is indicative of a clinical status (e.g., indicative of a disorder as described herein, e.g., delayed graft function). In other cases, the level of PGC1α in a subject being greater or equal to than the reference level is indicative of the absence of disease or normal risk of the disease. In some embodiments, the amount by which the level in the subject is the less than the reference level is sufficient to distinguish a subject from a control subject, and optionally is a statistically significantly less than the level in a control subject. As used herein, "being equal" refers to being approximately equal (e.g., not statistically different).

The predetermined value can depend upon the particular population of subjects (e.g., human subjects) selected. For example, an apparently healthy population will have a different 'normal' range of levels PGC1α than will a population of subjects which have, are likely to have, or are at greater risk to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

As an alternative to or in addition to measuring PGC1α, one of skill in the art would be able to use other methods of non-invasive assessment, e.g., based on metabolites (e.g., urinary metabolites) that are indicative of PGC1α-NAD status: (1) the quinolinate, tryptophan and other metabolite ratios in samples (e.g., urine) from humans with AKI; and (2) urinary mitochondrial DNA abundance from people with kidney injury vs. those without. Mitochondrial DNA integrity is also reduced after kidney injury, and could be easily assayed in a biofluid. These same markers could also be applied in the blood as well for heart and brain injury.

NAD Pathway Agonists

The methods described herein include administration of a therapeutically effective amount of a NAD/NAM pathway agonist. The agonists that are useful in the present methods include those that act directly on the NAD pathway, such as Nicotinamide adenine dinucleotide (NAD); niacinamide (NAM) itself; nicotinamide mononucleotide (NMN) (see, e.g., Yoshino et al., Cell Metabolism 14:528-536 (2011); P7C3 class of aminopropyl carbazole chemicals and analogs thereof including P7C3-A20 that comprise the P7C3 scaffold and bind nicotinamide phosphoribosyltransferase (NAMPT), the rate-limiting enzyme involved in the conversion of nicotinamide into nicotinamide adenine dinucleotide (NAD) (see, e.g., Pieper et al., Cell, 142(1):39-51 (2010); Wang et al., Cell. 158(6): 1324-1334 (2014); Naidoo et al., Tetrahedron Letters 54(33):4429-4431 (2013)); Nicotinamide riboside (NR) and other nicotinoyl ribosides and nicotinamide riboside derivatives that promote the increase of intracellular levels of nicotinamide adenine dinucleotide (NAD+) in cells and tissues (e.g., as described in Walter and Kaplan, J. Biol. Chem. 238(8):2823-2830 (1963); US20150072950; or 20120172584, which are incorporated herein in its entirety).

Alternatively, a NAD/NAM pathway agonist useful in the methods described herein can include an agent that increases the half-life of NAM, e.g., by reducing degradation of NAM. The pathway by which niacinimide is disposed of by the body is induced in AKI; N'-Nicotinamide Methyltransferase (NNMT) is the rate-limiting enzyme in that pathway. As shown herein, levels of NNMT go up in AKI. Inhibitors of NNMT (e.g., a interfering nucleic acid such as siRNA, small molecule inhibitors such as S-Adenosylethionine and S-adenosylhomocysteine or analogs thereof, or a reaction product to cause feedback inhibition such as 1-methyl NAM or N-methyl NAM), can be used to increase NAM levels to boost this kidney-protecting pathway. Methods for identifying other inhibitors of NNMT are known in the art; for example, commercially available assays for identifying additional NNMT inhibitors are available from Biovision. In this kit, the relevant activity is NNMT methylation of nicotinamide generating S-adenosylhomocysteine (SAH) and 1-methylnicotinamide. The SAH is hydrolyzed by SAH hydrolase to form homocysteine, and the free thiol group of the homocysteine is detected using a thiol-detecting reagent that generates a fluorescence signal. In the presence of an NNMT inhibitor, the enzymatic activity is inhibited resulting in decreased fluorescence.

PGC1α Nucleic Acids

The present methods can also include administration of nucleic acids encoding PGC1α, e.g., nucleic acids comprising a sequence encoding PGC1α. Exemplary sequences for human PGC1α, also known as PPARG coactivator 1 alpha (PPARGC1A), are provided below:

| GenBank RefSeq mRNA | GenBank RefSeq Protein | Sequence name |
|---|---|---|
| NM_001330751.1 | NP_001317680.1 | peroxisome proliferator-activated receptor gamma coactivator 1-alpha isoform 1 |
| NM_001330752.1 | NP_001317681.1 | peroxisome proliferator-activated receptor gamma coactivator 1-alpha isoform 3 |
| NM_001330753.1 | NP_001317682.1 | peroxisome proliferator-activated receptor gamma coactivator 1-alpha isoform 4 |
| NM_013261.4 | NP_037393.1 | peroxisome proliferator-activated receptor gamma coactivator 1-alpha isoform 2 |

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the NNMT target nucleic acid and modulate its function. Exemplary human NNMT sequences are in GenBank at Accession No. NM_006169.2 (mRNA) and NP_006160.1 (protein); sequences for other species are also commercially available.

In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112; Kraus et al., Nature. 2014 Apr. 10; 508(7495):258-62 (describing NNMT antisense oligos); Pozzi et al., PLoS One. 2013 Aug. 21; 8 (8): e71272 (describing NNMT RNAi); Yu et al., Cell Physiol Biochem. 2015; 35(2):710-21 (describing NNMT RNAi); Sartini et al., Biol Chem. 2015 March; 396(3):225-34 (describing NNMT shRNA).

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the Ablim3 sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within an Ablim3 sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity (i.e., they do not bind to other transcripts sufficiently to produce any significant undesirable off-target effects), to give the desired effect.

siRNA/shRNA

In some embodiments, the nucleic acid sequence that is complementary to an Ablim3 RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages. (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O— P—O—CH); amide backbones (see De Mesmaeker et al. Acc. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$ OCH$_3$, OCH$_3$ O(CH$_2$)n CH$_3$, O(CH2)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-0-CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G, et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. Nos. 3,687,808, 4,845,205; 5,130,302; 5,134,066; 5,175, 273; 5, 367,066; 5,432,272; 5,457,187; 5,459,255; 5,484, 908; 5,502,177; 5,525,711; 5,552,540; 5,587,469; 5,596, 091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34: e60 (2006); McTigue et al., Biochemistry 43:5388-405 (2004); and Levin et al., Nuc. Acids. Res. 34: e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-0 atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and*

*Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory nucleic acid sequences designed to target an RNA.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy*, 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST¾ 45, ALT¾ 35) for all doses with the exception of the 75 mg/kg dose of miR-122 ASO, which showed a very mild increase in ALT and AST levels. They concluded that 50 mg/kg was an effective, non-toxic dose. Another study by Krutzfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

Delivery of siRNA In Vivo

The overall efficacy of RNAi-based therapies depends on the efficiency of the delivery system to selectively target infected or diseased tissue versus normal non-malignant tissue, and on the stability of the agent within the cell. However, since 1998 when the first human RNAi-based clinical trials occurred, the number of clinical trials involving RNAi therapies targeting the liver has rapidly increased (Sehgal, A et al (2013) J. Hepatology 59: 1354-1359). To avoid rapid degradation of unmodified siRNAs in the blood and serum in vivo, chemical modification or conjugate formation (simple or poly-) may be used by those skilled in the art. Examples of modifications may include lipid carriers, such as liposomal vehicles (Kanasty, R et al (2013) Nature Mater. 12, 967-977); Watanabe et al (2007) J. Hepatol 47:744-50; Aleku et al (2008) Cancer Res 68:9788-98; Moreira et al (2008) J. Nanosci Nanotechnol 8:2187-204; cationic carriers, such as cyclodextrin-based cationic polymers (Heidel et al (2007) Clin Cancer Res 13:2207-15) and biodegradable components (Dimitrova et al (2008). In some embodiments, liposome particles (Morrissey, D V et al (2005) Biotechnol 23:1002-1007), PEGylated nanoparticles (Carmona, S et al (2009) Mol Pharm 6:706-717), or Dynamic PolyConjugate (DPC) (Rozema et al (2007) PNAS 104: 12982-12987) may be used to deliver siRNAs to the liver. In some embodiments, this delivery system may feature reversibly masked polymers that are only revealed under specific conditions, such as the acidic environment of the endosome (Rozema et al (2007) PNAS 104: 12982-12987). In some embodiments, the delivery system may dependent on the attachment to a liver-specific receptor on the cell surface of hepatocytes, such asialoglycoprotein (Wu, J et al (2002) Front Biosci 7: d717-d725). In some embodiments, the target siRNA may directly be conjugated to cholesterol (Wooddell, C et al (2013) Mol Therapy 21:973-985). In some embodiments hydrodynamic intravenous injections and electrical pulsing may be used to directly deliver RNAi therapeutics (Morrissey et al (2005) Hepatology 41:1349-56; Golzio et al (2005) Gen Ther 12:246-51). RNAi therapeutics may also be delivered via electroporation of purified exosomes (Alvarez-Erviti et al (2011) Nat Biotechnol 29:341-345). For more information on in vivo delivery of RNAi, please see U.S. Ser. No. 12/479,747; U.S. Pat. Nos. 8,501,930, 8,017,804; 8,357,722; 8,314,227; and 7,371,404.

EXAMPLES

The invention is further described in the following examples, which do not limit the scope of the invention described in the claims.

Methods

The following materials and methods were used in the Examples set forth below.

Mouse Studies:

All studies with mice were reviewed and approved by the Institutional Animal Use and Care Committee of Beth Israel Deaconess Medical Center (BIDMC). PGC1α$^{-/-}$ (stock #008597), Pax8-rtTA (#007176) and TRE-PGC1α (#012387) mice were all obtained from Jackson Laboratories and bred at BIDMC. The parental strains were generated on a mixed C57 background with further backcrossing into C57BL/6J as described by the manufacturer, except for the TRE-PGC1α mouse, which was generated on and is maintained on FVB. Primers for genotyping have been described elsewhere (Tran et al. J Clin Invest 2011; 121, 4003-4014; Traykova-Brauch et al. Nat Med 2008; 14, 979-984). All experiments were performed with littermate controls.

Renal ischemia-reperfusion injury (IRI) was performed on 8-12 week-old males through two small paramedial dorsal incisions by applying a microvascular clamp to each renal pedicle for 20 minutes. Mice were anesthetized with isoflurane for the duration of surgery and warmed to 37° C. using a servo-controlled heating pad. Incisions were closed in two layers and mice were revived with 1 ml warm saline injected intraperitoneally.

For cardiac IRI surgery, mice were anesthetized, intubated, and placed on a rodent ventilator. After thoracotomy, the left anterior descending artery was identified and ligated with a 7-0 silk suture tied around a specialized 30 gauge catheter. The animal remained under anesthesia and ventilation for 45 minutes of ischemia. Reperfusio was achieved by cutting the suture and re-establishing arterial perfusion. The thoracotomy was then sutured closed and animals recovered with warmed saline injected intraperitoneally.

Pressure volume loops were performed to assess cardiac parameters. Cardiac function was measured in mice using the left ventricle (LV) pressure-volume and echocardiography 2 weeks after cardiac IRI or sham control procedure. After 2% isolfurane inhalant anesthesia, the pressure-volume parameters were measured using a 1.4 French microtip pressure-volume catheter. The catheter was first inserted into the right common carotid artery and then gently advanced into the LV to obtain LV hemodynamic measurements. Data were recorded using a Powerlab system. Beat-by-beat pressure-volume parameters including heart rate, stroke volume, stroke work, and cardiac output were measured and analyzed using Cardiosoft Pro software. Tranthoracic echocardiography was performed using a Vevo2100 echocardiogram with a MS400 (18-38 MHz) transducer at baseline and 2 weeks after cardiac IRI. Two-dimensional guided M-mode images were recorded. See Bae et al., J Am Heart Assoc. 2016 Nov. 14; 5 (11).

All chemicals were purchased from Sigma-Aldrich unless otherwise noted. Niacinamide was given by intraperitoneal injection of 400 mg/kg/day×4 days in saline, with the final dose an hour prior to IRI surgery. In rescue experiments, the same dose was administered once 18 hours after reperfusion. Indomethacin was given by intraperitoneal injection of 10 mg/kg in 0.1 M sodium carbonate/saline an hour prior to IRI. The HCAR2 inhibitor, mepenzolate bromide, was given by intraperitoneal injection of 10 mg/kg in saline an hour prior to IRI (Rask-Andersen et al. Drug discovery 2011; 10, 579-590; Singh et al. Cell host & microbe 2012; 12, 669-681; Feingold et al. J Lipid Res 2014; 55, 2501-2508) LPS (*E. coli* serotype O111:B4) was given by intraperitoneal injection of 25 mg/kg in saline. Cisplatin was given by intraperitoneal injection of 25 mg/kg as previously described (Zsengeller et al. J Histochem Cytochem 2012; 60, 521-529). Unless otherwise stated, blood and kidneys were collected 24 h after the AKI model.

Mass Spectrometry Measurements:

All measurements were performed in a blinded fashion by an independent facility. Creatinine was analyzed by LC/MS-MS at the University of Alabama Birmingham O'Brien Core Center for Acute Kidney Injury Research (NIH P30-DK079337). This method adds the accuracy of MS to the LC method of creatinine measurement endorsed by a renal investigative consortium (diacomp.org). The coefficient of variation was 6% indicating high assay precision.

For metabolomics measurements, snap frozen kidneys were cut to equal weights (20 mg/specimen) and mechanically homogenized into 4 volumes of ice-cold water. Metabolites were assayed as previously described (Rhee et al. Cell Metab 2013; 18, 130-143). In brief, amino acids, amines, acylcarnitines, nucleotides, and other cationic polar metabolites were measured in 10 µl of kidney homogenate using hydrophilic interaction liquid chromatography coupled with nontargeted, positive ion mode MS analysis on an Exactive Plus Orbitrap MS (Thermo Scientific). Polar and non-polar lipids were measured in 10 µl of kidney homogenate using C8 chromatography and nontargeted, positive ion mode MS analysis on a Q Exactive MS (Thermo Scientific). Identification of known metabolites was achieved by matching retention times and mass-to-charge ratio (m/z) to synthetic mixtures of reference compounds and characterized pooled plasma reference samples. Results were analyzed in MetaboAnalyst (Xia et al., Nucleic Acids Res. 40 (Web Server issue): W127-33 (2012)).

LC-MS assays were developed for multiplex quantification of Nam, NAD, and $\beta$-hydroxybutyrate ($\beta$-OHB) from cellular experiments. NAD measurements reflect total $NAD^+$ plus NADH. Briefly, conditioned medium was extracted with methanol (80% methanol final concentration) spiked with isotopic standards for Nam and $\beta$-OHB (CDN Isotopes, Inc.). Precipitated proteins were removed by centrifugation, and supernatants were analyzed directly. For analysis of cell lysates, cells were washed with ice-cold PBS, scraped and lysed on dry ice into methanol containing isotopic standards. After extraction, cell and media supernatants were analyzed by LC-MS/MS using reverse-phase chromatography (NAM and NAD/NADH) or hydrophilic interaction chromatography ($\beta$-OHB) coupled to tandem mass spectrometry using an API 5000 triple quadruple mass spectrometer. Analytes were quantified by multiple reaction monitoring using the following m/z transitions: $\beta$-OHB 103.1>59, $\beta$-OHB IS 105.1>60, NAM 123.3>80.2, NAM IS 127.3>84.2, NAD/NADH 664.2>542.0. Eluting peaks were quantified by area under the curve (AUC).

Raw AUC values were divided by the mean value of the control group for each experiment, thus the results are presented as relative concentrations to the control group. All assays were performed in triplicate and replicate measurements demonstrated a CV<5%.

RNASEQ Sequencing and Identification of Differentially Expressed Transcripts:

PolyA-enriched RNA was isolated from whole kidneys and checked for quality by denaturing agarose gel as well as Aglient Bioanalyzer. Sequencing libraries were generated from the double-stranded cDNA using the Illumina TruSeq kit according to the manufacturer's protocol. Library quality control was checked using the Agilent DNA High Sensitivity Chip and qRT-PCR. High quality libraries were sequenced on an Illumina HiSeq 2000. To achieve comprehensive coverage for each sample, we generated ~25-30 million single end reads. Raw results were passed through quality controls steps and aligned to the mouse genome. Gene expression measurement was performed from aligned reads by counting the unique reads. The read count based gene expression data was normalized on the basis of library complexity and gene variation. The normalized count data was compared among groups using a negative binomial model to identify differentially expressed genes. The differentially expressed genes were identified on the basis of raw P value and fold change. Genes were considered significantly differentially expressed if the multiple test corrected p-value was <0.05 and absolute fold change >2.

Functional Enrichment Analysis:

INGENUITY Pathway Analysis (IPA 8.0, Qiagen) was used to identify the functions that are significantly affected by significantly differentially expressed genes from different comparisons. The knowledge base of this software consists of functions, pathways, and network models derived by systematically exploring the peer reviewed scientific literature. A detailed description of IPA analysis is available at the Ingenuity Systems' web site (ingenuity.com). A p-value is calculated for each function according to the fit of the users' data to the IPA database using one-tailed Fisher exact test. The functions with multiple test corrected p-values <0.01 were considered significantly affected.

Western Analysis:

Kidney lysate preparation, gel electrophoresis, transfer, immunoblotting, detection, and image acquisition were performed as previously described (Tran et al. J Clin Invest 2011; 121, 4003-4014). Antibodies against PGC1c (Cayman Chemical), cytochrome c oxidase subunit IV (Cell Signaling Technology), and Transcription Factor A Mitochondrial, TFAM (Abcam) were used as previously described (Tran et al. J Clin Invest 2011; 121, 4003-4014; Kang et al. J Appl Physiol (1985) 115, 1618-1625 (2013)).

Quantitative PCR:

Total RNA extraction and cDNA synthesis were performed as previously described (Tran et al. J Clin Invest 2011; 121, 4003-4014). PCR reactions were performed in duplicate using the ABI 7500 Fast Real-Time PCR and TaqMan gene expression assays (Applied Biosystems). The following TaqMan gene probes were used: Ppargc1a, Ndufs1, Cycs, Atp5o, Nrf1, Tfam, Vegfa, Nos1, Nos3, Hcar2. Of the four known Ppargc1a transcripts (1-4), Ppargc1a1 (Taqman Mm00447183_m1) was studied in all gene expression analyses (Ruas et al. Cell 2012; 151, 1319-1331). Mouse Ido2, Afmid, Kynu, Kmo, Haao, Qprt, Naprt, and Nmnat1 for SYBR Green PCR have been described elsewhere (Nakahata et al. Science 2009; 324, 654-657; Agudelo et al. Cell 2014; 159, 33-45). Mouse Nampt SYBR primers were designed using PrimerQuest Tool (Integrated DNA Technologies). Relative expression levels were determined using the comparative threshold method.

Mitochondrial DNA Copy Number Analysis:

Total DNA was extracted from mouse kidneys using the DNeasy Blood and Tissue Kit (Qiagen) with on-column RNase digestion per manufacturer's instructions. *Gene* expression of mitochondrial-encoded NADH dehydrogenase 1 (mt-Nd1) relative to nuclear 18S rRNA was used to determine mitochondrial DNA copy number as previously described (Liu et al. J Clin Invest 2014; 124, 768-784).

Histopathology:

Formalin-fixed, paraffin-embedded blocks were sectioned and stained with H & E, PAS, and Masson trichrome. Ten random high-power fields in the cortex and ten random high-power fields in the outer stripe of the outer medulla were viewed and graded for tubular necrosis-defined as the loss of the proximal tubular brush border, blebbing of apical membranes, tubular necrosis/apoptosis and epithelial cell detachment from the basement membrane or intraluminal aggregation of necrotic debris. Each high-power field was separately scored on a scale (0=no necrosis, 1=rare single necrotic cells, 2=frequent single necrotic cells, 3=groups of necrotic cells, and 4=confluent tubular necrosis) and the average score was compiled for each specimen and then used for between-group comparisons. All scoring was performed by a single operator blinded to genotype and experimental model (IES).

In Situ COX Enzyme Chemistry—

Enzyme histochemistry to detect cytochrome c oxidase (COX) activity was performed on 6 μm snap-frozen sagittal sections as previously described (Tran et al. J Clin Invest 2011; 121, 4003-4014). Functional electron microscopy used in the cisplatin kidney injury model was described earlier (Zsengeller et al. Cell Metab 2013; 18, 130-143).

Electron Microscopy:

The complete method is previously described (Tran et al. J Clin Invest 2011; 121, 4003-4014). Briefly, kidneys were fixed with 1.25% glutaraldehyde in 0.1 M cacodylate buffer (pH 7.4) and cut in 1 μm section in both sagittal and transverse planes for image analysis. After drying the sections, slides were stained at 65° C. for 20 minutes in 0.1% Toluidine blue in 1% sodium borate, cooled to room temperature, washed in distilled water, cleaned in xylene, and mounted in Permount sections for light microscopy. Subsequent ultrathin sections (0.5 μm) were examined by transmission electron microscopy (JEOL 1011, JEOL Corp.) with Orca-HR Digital Camera (Hamamatsu Corp.), and Advanced Microscopy Technique Corporation image capture system.

Oil-Red-O Staining:

Oil-Red-O solution was prepared by dissolving 0.5 g Oil-Red-O (Poly Scientific) in 100 ml isopropanol. Frozen sections were cut to 5 m and natively stained in Oil-Red-O solution for 20 minutes at room temperature, then rinsed in running tap water for 2 min. Hematoxylin counter-staining was performed without differentiation in HCl-ethanol and sections were rinsed with water, then mounted with Vecta-Mount AQ Aqueous Mounting medium (Vector Labs).

Human Biopsy Series:

All studies were approved by the Institutional Review Board at BIDMC. Control specimens came from normal tissue sections of nephrectomies. CKD diagnoses included focal segmental glomerulosclerosis, chronic allograft nephropathy, chronic interstitial nephritis, and chronic IgA nephropathy. AKI diagnoses included acute ischemic injury, post-transplant delayed graft function attributable to ischemia-reperfusion injury, and acute interstitial nephritis. PGC1α antibody (Abcam ab54481) was used at a dilution of 1:100 and developed with horseradish peroxidase (ImmPRESS polymer staining kit, Vector Labs). The peptide immunogen SKYDSLDFDSLLKEAQRSLRR (SEQ ID NO:1, synthesized by the Biopolymers Lab, Koch Institute at MIT) was pre-incubated in 100-fold excess of the PGC1α antibody to confirm antibody specificity in human IHC studies. Ten randomly selected high-powered fields were viewed per specimen, with each field scored on a 4-point scale (1=weakest, 4=strongest) based on the intensity of staining, specifically in non-necrotic areas and unscarred areas and avoiding obvious collecting ducts. The average score of each specimen was then used for between-group comparisons. All scoring was performed by a single operator blinded to the underlying diagnosis (IES).

Microultrasound:

The full method is previously described (Tran et al. J Clin Invest 2011; 121, 4003-4014). Briefly, mice were lightly anesthetized, secured to a heat-controlled stage, and continuously monitored for respiration, ECG, and core temperature. A high frequency, high resolution digital imaging platform with linear array technology and equipped with a high-frequency linear array probe MS550D (22-55 MHz) was used throughout the study (Vevo 2100 Visual Sonics). The flow volume was modeled as a circular cylinder of length equal to the average velocity time integral and diameter measured empirically (n=3 cardiac cycles), then multiplied by the heart rate (bpm), then converted from mm$^3$/min to ml/min. All measurements and analyses were performed by a single blinded operator (EVK).

Cellular Studies:

Mouse intermedullary collecting duct (IMCD3) cells were obtained from ATCC. Please refer to their website for validation and *mycoplasma* testing. Cells were transfected with siRNA targeting mouse PGC1, HCAR2 or a negative control siRNA (Qiagen) for 24 h. Niacin, mepenzolate bromide, β-hydroxybutyrate, the NAMPT inhibitor FK866 (Hasmann et al. Cancer research 2003; 63, 7436-7442), and niacinamide were diluted to the indicated concentrations in serum-free cell culture medium. Prostaglandin E$_2$ (PGE$_2$) was measured in the conditioned media 24-72 hours after treatment.

Cystatin C:

Cystatin C in mouse serum (1:200 dilution) was measured by ELISA (R&D Systems).

FITC-Inulin Clearance:

The full method is described elsewhere (Qi et al. Am J Physiol Renal Physiol 2004; 286, F590-596). Briefly, male C57BL/6J mice (Jackson Laboratories) were given a single bolus injection of 5%-FITC-inulin (3.74 µl/g body weight). Clearance kinetics of FITC-inulin post-injection was measured by serial blood collection at specified time points from 3 through 70 minutes post-injection. Blood samples were centrifuged and resulting plasma was buffered to pH 7.4 with 500 mM HEPES. Fluorescence in the buffered plasma samples was determined with 485 nm excitation, 538 nm emission. Glomerular filtration rate (GFR) was calculated from the two phase exponential decay model outlined previously.

Tissue PGE$_2$ β-OHB, and NAD Measurements:

PGE$_2$ was measured in mouse kidney tissue by ELISA (Cayman Chemical). β-OHB (Cayman Chemical) and total NAD (BioVision) was measured in mouse kidney tissue by colorimetric assays. These assays were performed on kidneys used for metabolomics and lipidomics in order to compare coordinated changes in metabolism and downstream signaling. NAD measurements reflect total NAD$^+$ plus NADH.

Statistical Analysis:

Comparisons between continuous characteristics of subject groups were analyzed with Mann-Whitney U tests or Student's t test. Survival was analyzed by log-rank test. For comparisons among more than two groups, ANOVA with Bonferroni correction was used where indicated. Associations between microultrasound measurements and other functional parameters were analyzed with Spearman's rank correlation coefficients. Sample size determination was guided by power calculations and prior experience. The following sample calculation was used to guide creatinine studies in mice: serum creatinine of 1.6 (±0.3 SD) mg/dl vs. 1.0 (±0.2 SD) requires n=5 mice per condition to achieve an α-error <5% and power 96%. Mice were randomized to experimental intervention vs. control. Two-tailed p-values <0.05 were considered significant. Results are presented as mean±SEM and were prepared in GraphPad Prism.

Retrospective Cohort Study:

Retrospective cohort study of patients who underwent renal transplant at BIDMC from 01/01/08-06/30/14 and received a renal allograft biopsy for delayed graft function (DGF) within 30 days of transplant. Delayed graft function (DGF) was defined as the need for dialysis within 7 days of transplant. In 2008, DGF occurred in 21.3% of all transplants. DGF negatively impacts allograft survival: increased incidence of acute rejection and risk factor for chronic allograft nephropathy and graft loss. (Legendre et al. Transpl Int 2014; 27:19-27; Yarlagadda et al. Nephrol Dial Transplant 2009; 24: 1039-47; Ojo et al. Transplantation 1997; 63:968-74). DGF cohort was identified using DGF diagnosis code in the BIDMC OTTR electronic medical record. Exclusion criteria: Patients were excluded if they did not undergo a renal allograft biopsy, if the biopsy was done greater than 30 days after transplant, or if the biopsy showed findings other than DGF. Immunostaining was conducted in a blind fashion as described in Tran, M. T. et al. Nature 2016; 531:528-32. All scoring of immunostaining intensity was performed by a single operator blinded to the underlying diagnosis as previously described herein.

Of a total of 74 subjects identified in the initial medical record review, 53 were excluded for one or more of the exclusion criteria described above, leaving a total of 21 subjects' biopsies and clinical records that were enrolled into the study. Features of the donor and transplant feature are described in the table below.

TABLE 1

Characteristics of patients in retrospective cohort study

| | Characteristic | Included (n = 21) | Excluded (n = 53) | P value |
|---|---|---|---|---|
| Donor Source | DCD, n (%) | 8 (38.1) | 16 (30.2) | 0.5857 |
| | ECD, n (%) | 3 (14.3) | 10 (18.9) | 0.7466 |
| | SCD, n (%) | 9 (42.9) | 22 (41.5) | 1.000 |
| | Living/related, n (%) | 0 (0) | 2 (3.8) | 1.000 |
| | Living/unrelated n (%) | 1 (4.8) | 3 (5.7) | 1.000 |
| Transplant | Mean HLA mismatches, n (SD) | 4.3 (1.8) | 4.2 (1.9) | 0.7982 |
| | Mean cold ischemia time, h (SD) | 17.7 (3.2) | 14.4 (7.7) | 0.0658 |
| | Induction therapy | | | |
| | ATG, n (%) | 18 (85.7) | 45 (92.5) | 0.3972 |
| | Basiliximab, n (%) | 2 (9.5) | 3 (5.7) | 0.6183 |
| Recipient | Mean age, y (SD) | 54.62 (12.2) | 56.15 (8.6) | 0.5425 |
| | Male gender, n (%) | 11 (52.4) | 39 (73.6) | 0.1013 |
| | AA race, n (%) | 6 (28.6) | 13 (24.5) | 0.7716 |
| | BMI > 30 kg/m2, n (%) | 8 (38.1) | 18 (34.0) | 0.7905 |
| | Cause of ESRD | | | |
| | Diabetes, n (%) | 6 (28.6) | 21 (39.6) | 0.4318 |
| | Hypertension, n (%) | 3 (14.3) | 11 (20.8) | 0.7441 |

TABLE 1-continued

Characteristics of patients in retrospective cohort study

| Characteristic | Included (n = 21) | Excluded (n = 53) | P value |
|---|---|---|---|
| Glomerular, n (%) | 2 (9.5) | 3 (5.7) | 0.6183 |
| Tubulointerstitial, n (%) | 4 (19.0) | 3 (5.7) | 0.0952 |
| Graft failure, n (%) | 3 (14.3) | 7 (13.2) | 1.000 |
| Polycystic kidneys, n (%) | 2 (9.5) | 4 (7.5) | 1.000 |
| Other, n (%) | 1 (4.8) | 4 (7.5) | 1.000 |
| Pretransplant dialysis, n (%) | 21 (100) | 52 (98.1) | 1.000 |

Table Legend 1:

DCD=donor cardiac death; ECD=extended criteria donor; SCD=standard criteria donor. Mean HLA mismatches refers to the number of alleles at the HLA locus that were mismatched between donor and recipient (out of a total of 6 alleles that are routinely tested). Mean cold ischemia time is given in hours and refers to period during which kidney is out of the donor in an ice-cold solution, but not yet implanted into the recipient. Induction therapy refers to types of immunosuppressive agents administered right after implantation into the recipient. ATG=anti-thymocyte globulin. AA race=African American; BMI=body-mass index; ESRD=end-stage renal disease. Pre-transplant dialysis refers to the number of subjects in each group who underwent dialysis for a period of time prior to transplant. Living donor transplants can often take place before the patient reaches a severity of kidney disease that necessitates chronic dialysis.

Example 1.1. PGC1α-Dependent NAD Biosynthesis Links Oxidative Metabolism to Renal Protection The mature renal tubule returns ~140 L/day of filtered plasma water back to the circulation by establishing energy-intensive electrochemical gradients between the filtrate and vasculature. The kidney is only second to the heart in mitochondrial abundance (Pagliarini et al. Cell 2008; 134:112-23). We hypothesized that PGC1α (peroxisome proliferator activated receptor gamma co-activator-1-alpha), enriched in renal tubules and important for stress resistance in the brain, heart and other metabolically active organs (Ruas et al. Cell 2012; 151:1319-31; Weidemann et al. Biochem J 1969; 112:149-66; Collins et al. J Biol Chem 1972; 247:778-83; Traykova-Brauch et al. Nat Med 2008; 14:979-84), regulates oxidative metabolism in the epithelium to affect overall kidney health.

Figures 1A, 1B:
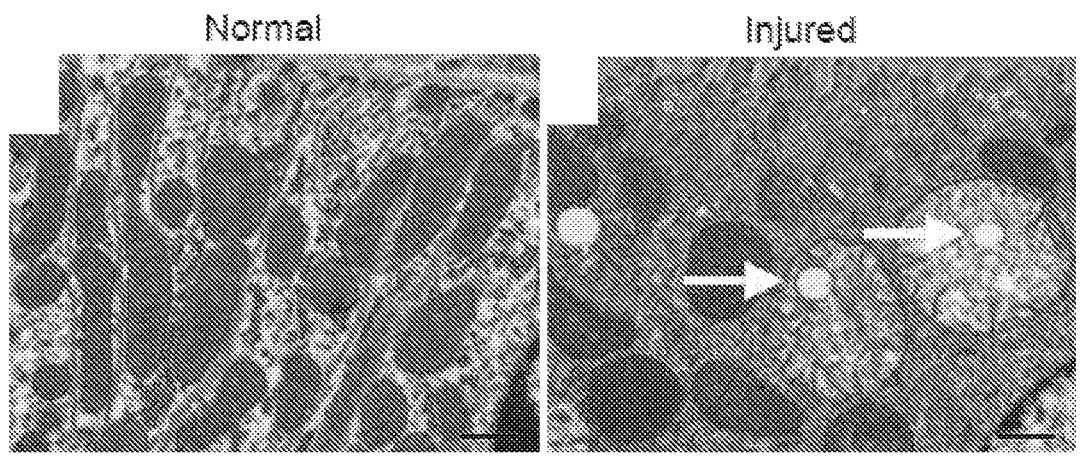
FIGS. 1A-I: Niacinamide (Nam) supplementation restores normal post-ischemic response in PGC1α$^{-/-}$ mice. A, Pre-ischemic normal morphology and B, swollen mitochondria inside tubular cell 24 h after ischemia-reperfusion injury (IRI). Scale bar 200 nm. C, Renal di-/tri-acylglycerols (DAGs, TAGs) 24 h following sham or IRI (n=6/group). P-value by ANOVA. D,E, Oil Red O (pink) for fat in normal and post-ischemic kidneys, scale bar 20 μm. F, serum creatinine wildtype (WT) vs PGC1α$^{-/-}$ (KO) mice (basal, n=7/group; post-ischemia, n=18/group). G,H, Volcano plots of kidney metabolites from KO vs. WT or IRI vs. sham (univariate p<0.05 for colored dots, n=6/group). I, Serum creatinine in post-ischemic WT vs. KO mice treated with vehicle (Veh, n=5) vs. Nam (n=9). Error bars SEM, *p<0.05, **p<0.01.
Figure 1C:
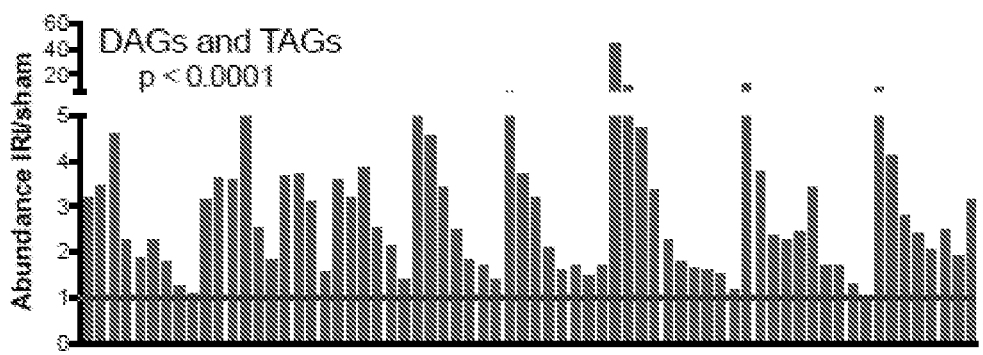
Figures 1D, 1E:
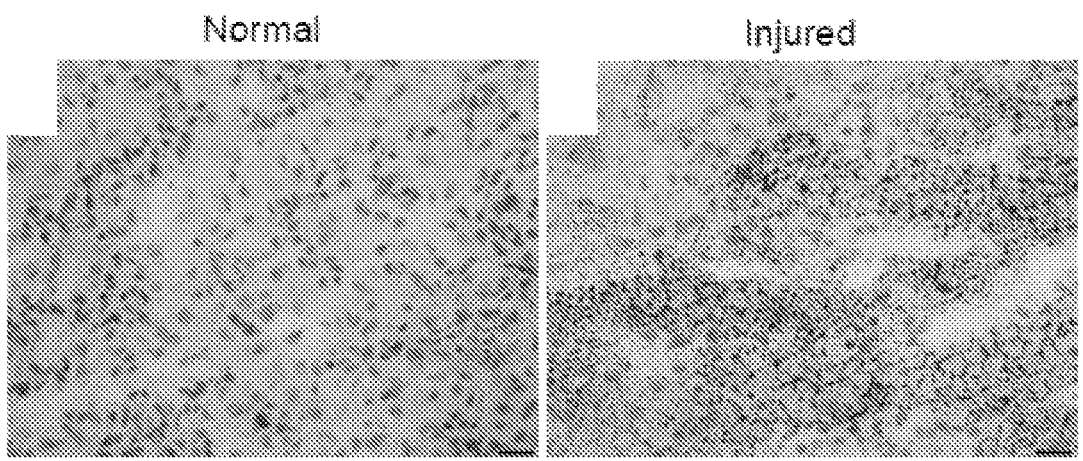
Figure 1F:
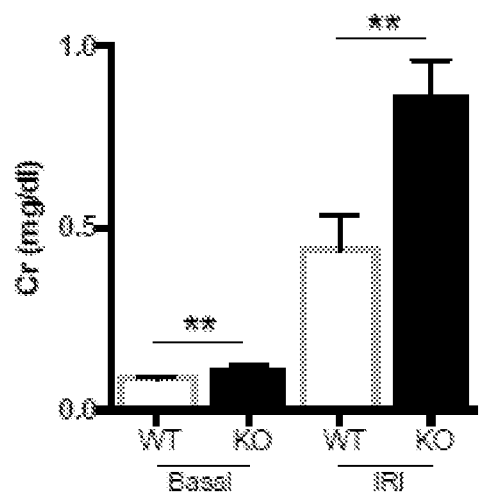
Figure 1G:
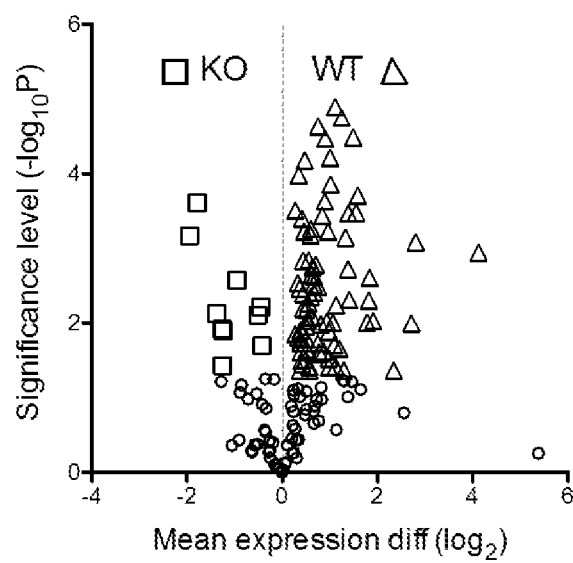
Figure 1H:
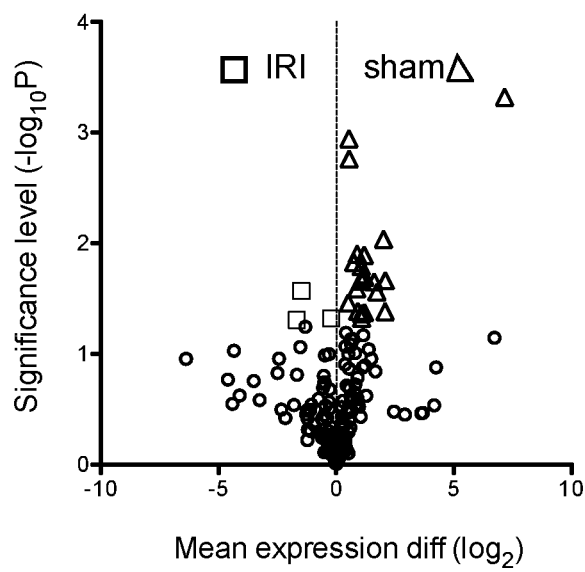
Figure 1I:
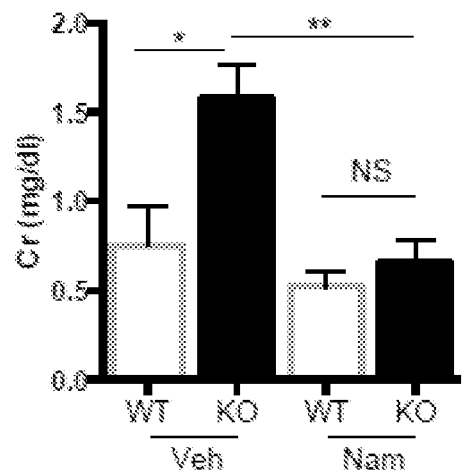
Figures 2A, 2B:
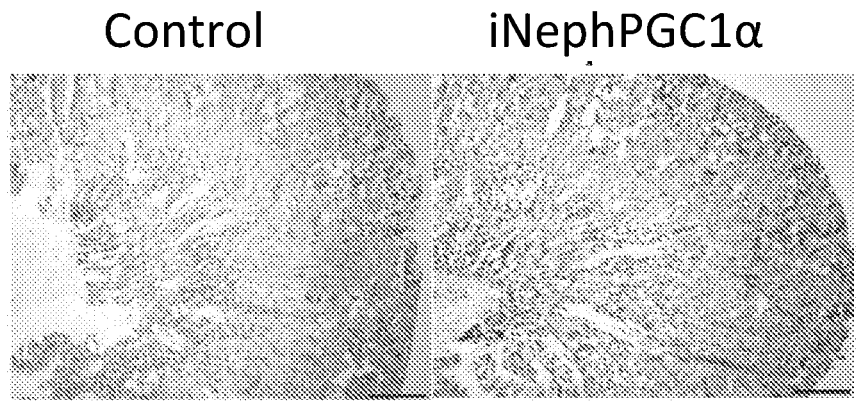
FIGS. 2A-Q: Metabolic protection in post-ischemic iNephPGC1α mice. A,B, Renal cytochrome c oxidase activity (brown), scale bar 500 μm. C, Renal PGC1α and cytochrome c oxidase subunit IV. D, Survival curve following IRI (n=14 control; 24 iNephPGC1α). Dashed line for sham-operated mice (n=10). E, Serial serum creatinines from mice in D analyzed by ANOVA. F,G, Renal artery pulse wave and color Doppler 24 h after IRI representative of 6/group. H-K, Tubular injury in cortex and outer stripe of outer medulla (OSOM) 24 h after IRI representative of 8/group. Scale bar 100 µm. L-O, Oil red O (pink) for fat in iNephPGC1α mice and controls 24 h after IRI representative of 8/group. Scale bars 200 µm (upper) and 50 µm (lower). P, Renal Di-/tri-acylglycerols (DAGs, TAGs) in post-ischemic iNephPGC1α mice vs. controls (n=6/group). Q, Relative renal Nam 24 h after IRI (n=6/group). Error bars SEM, *p<0.05.
Figure 2C:
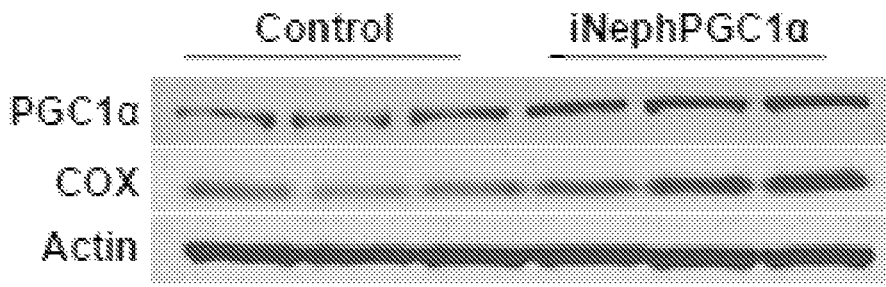
Figure 2D:
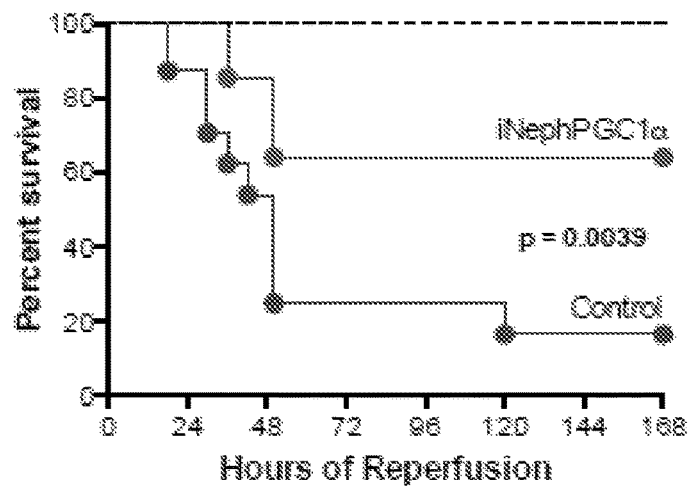
Figure 2E:
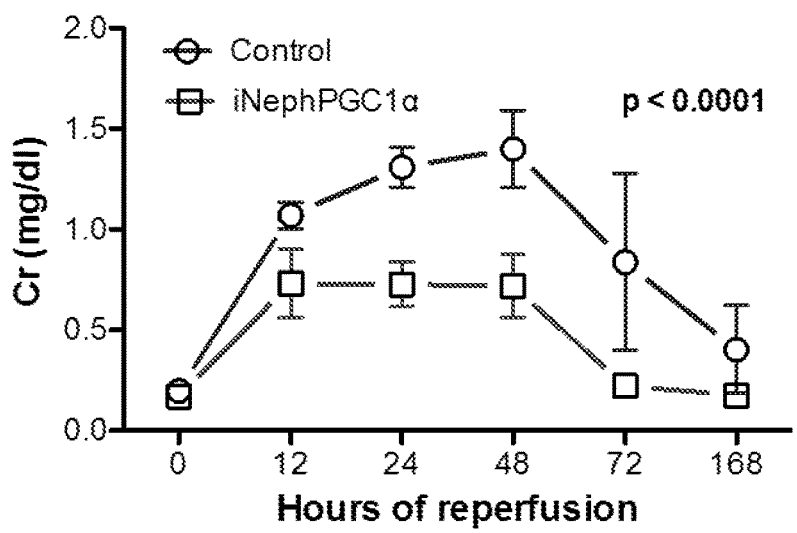
Figures 2F, 2G:
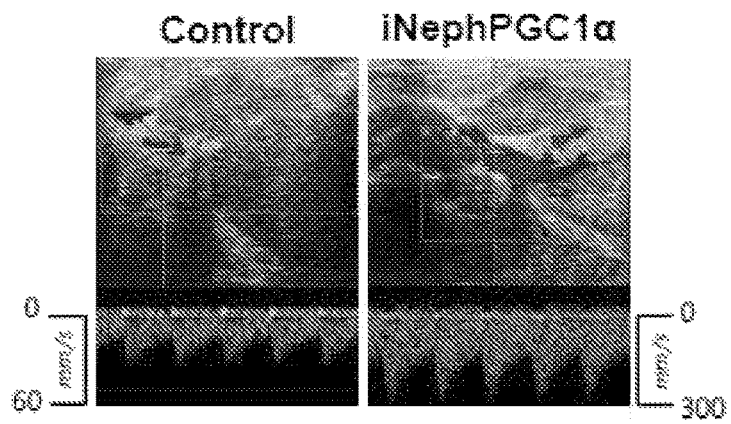
Figure 5A:
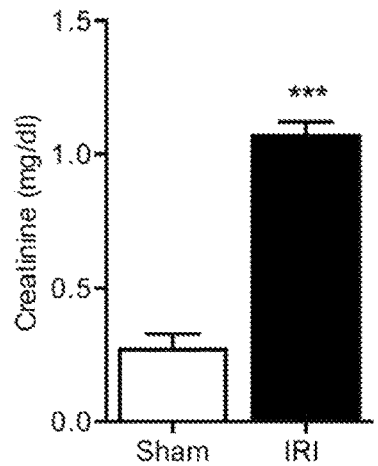
Figure 5B:
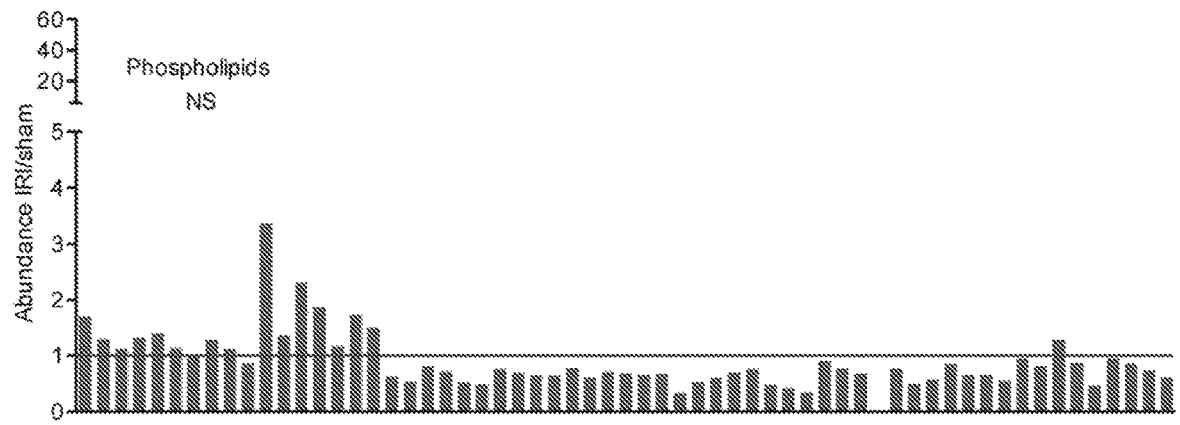
Figure 5C:
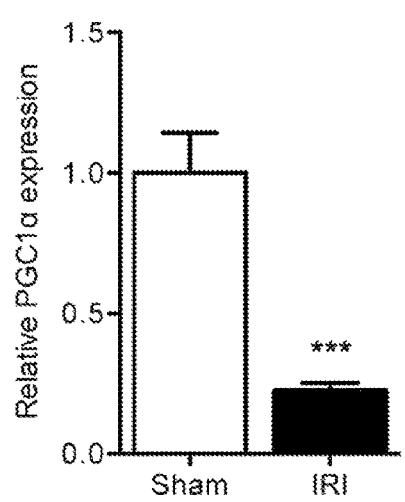
Figure 5D:
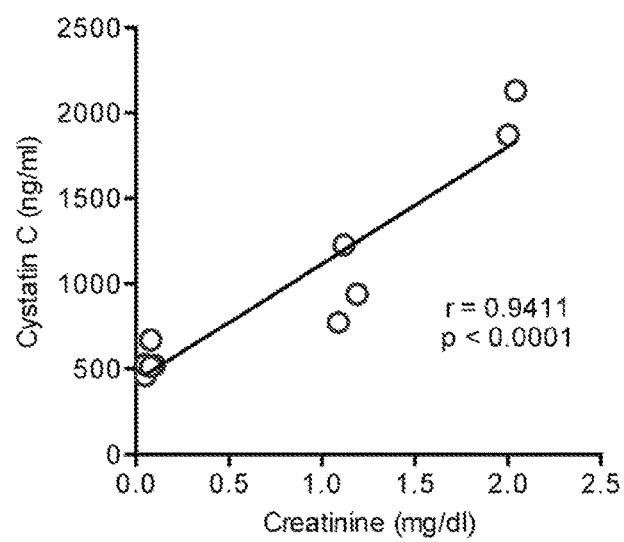
Figure 6E:
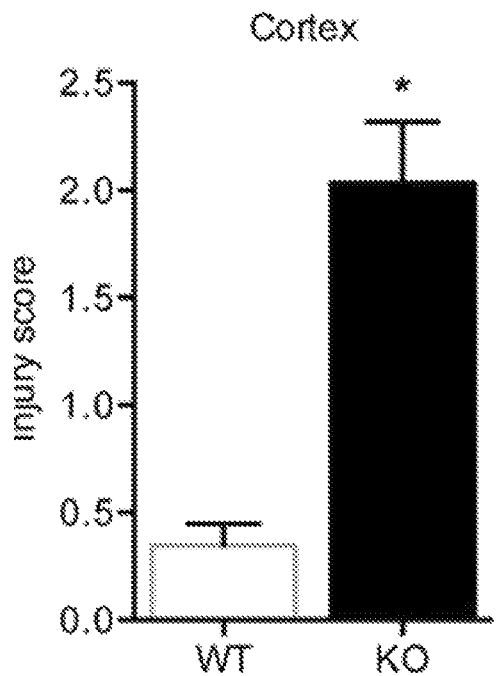
Figure 6F:
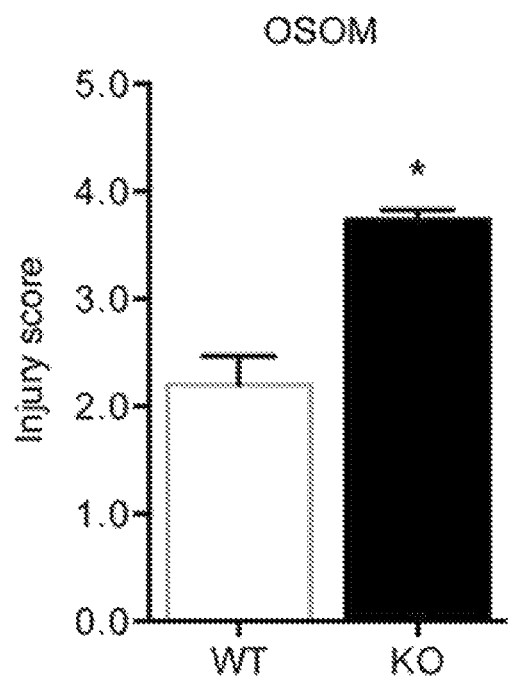
Figure 6G:
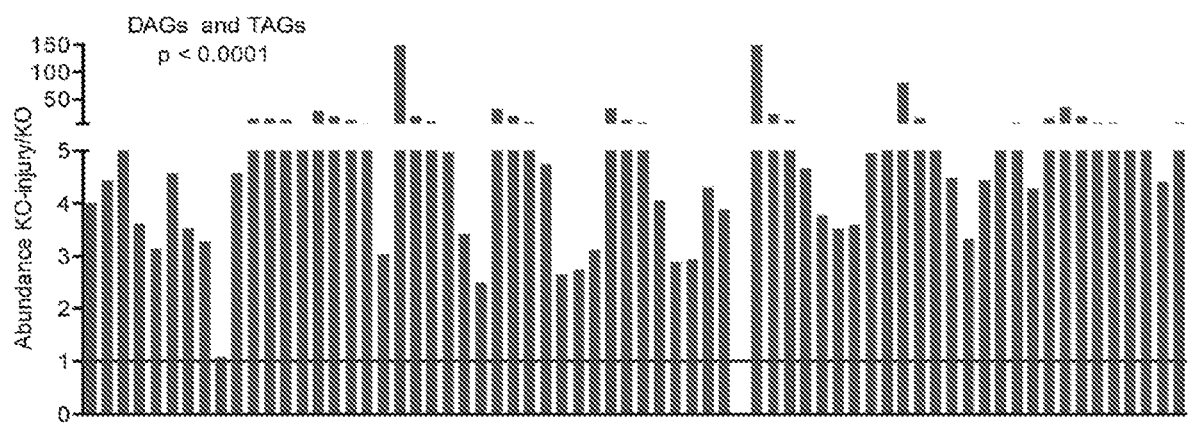
Figure 7A:
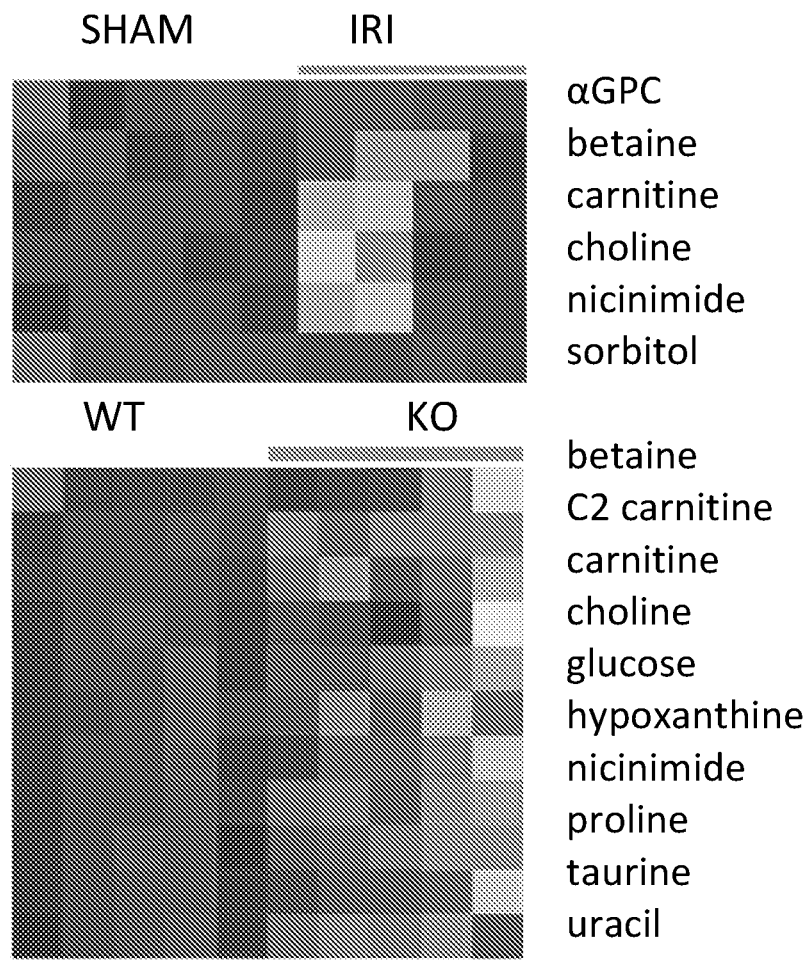
FIGS. 7A-H: Niacinamide (Nam) reduction from IRI and PGC1α deficiency. A, Heatmaps (red=higher, green=lower) of Bonferroni-corrected significantly different metabolites in sham vs. IRI kidneys and WT vs. KO kidneys. Metabolites listed in purple are shared between settings. B, Total ion chromatogram of polar, positive ion mode method for representative WT-IRI sample, with niacinamide (Nam) peak at retention time=3.88 minutes. Inset shows representative niacinamide peaks for kidney extracts from WT control (Ctrl) and WT-IRI (IRI) mice. C-E, Relative renal Nam abundance in kidneys of KO mice vs. WT littermates; WT littermates at baseline and 24 h after IRI; and KO mice at baseline and 24 h after IRI (n=6/group). F, Relative renal Nam concentrations in kidneys of mice following vehicle (Veh) vs. Nam treatment (400 mg/kg IP×4 d) with and without IRI 24 h prior to tissue collection (n=6/group). P-values by two-way ANOVA. G,H, Oil Red O stain (pink) for fat accumulation 24 h after IRI with or without Nam pretreatment (400 mg/kg IP×4 d), scale bar 20 µm. Error bars SEM, *p<0.05, p<0.01, *p<0.001.
Figure 7B:
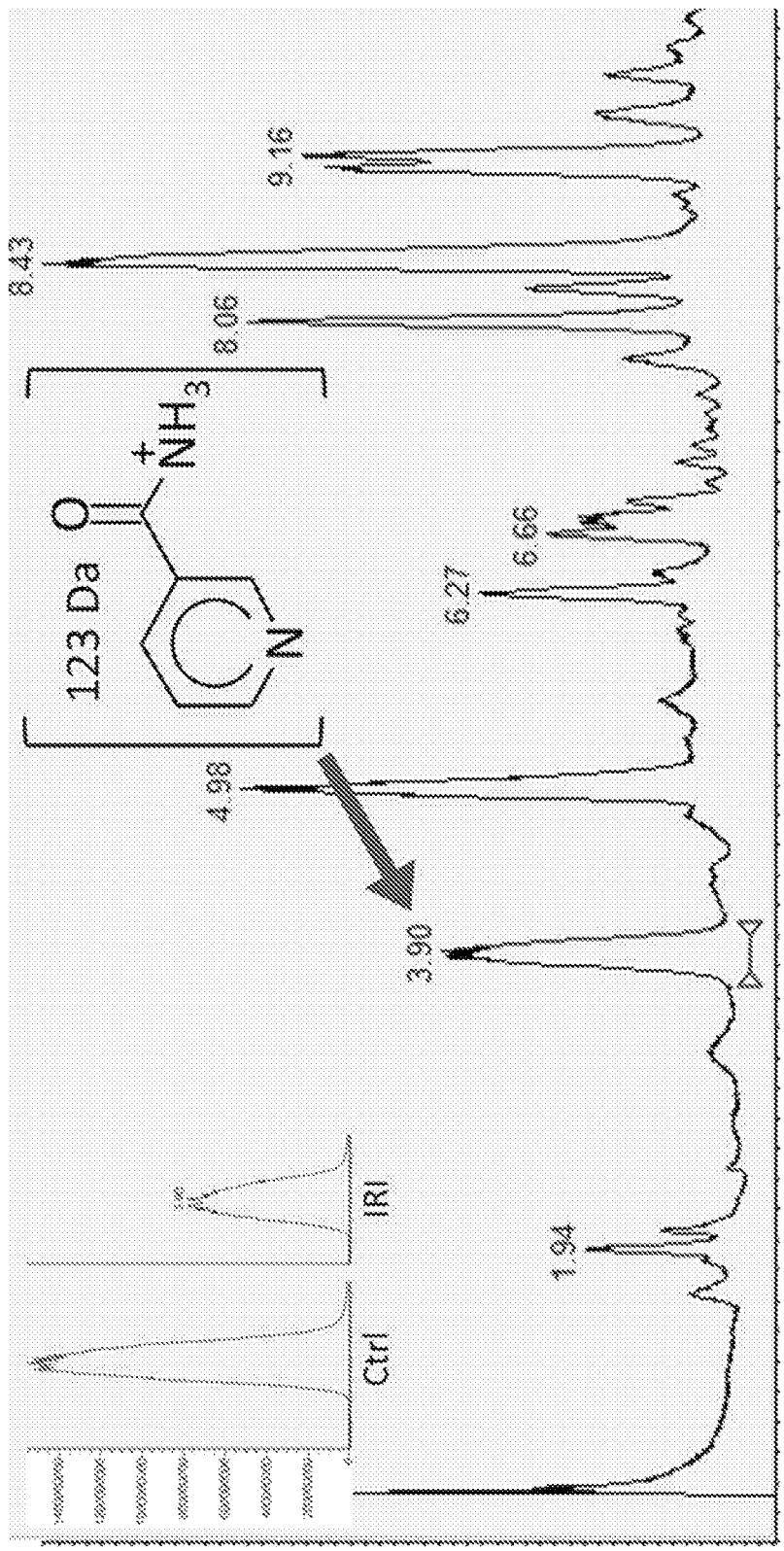

Hans Krebs identified acylglycerols as a major renal fuel (Weidemann et al. Biochem J 1969; 112:149-66). Following transient local ischemia, renal function worsened, PGC1α expression declined, tubular mitochondria swelled, and a pronounced accumulation of acylglycerols developed in tubules (p<0.0001, FIG. 1A-E, FIGS. 5a-C). The fidelity of serum creatinine was confirmed by comparison to cystatin C and inulin clearance (FIGS. 5D-F). PGC1α$^{-/-}$ mice experienced worse renal function, greater fat accumulation, and more tubular injury following ischemia (FIG. 1F, FIGS. 6A-G). To define pathways specific to PGC1α altered by ischemia, we examined metabolite profiles. Comparing sham vs. post-ischemic kidneys yielded six differentially abundant metabolites; comparing uninjured PGC1α$^{-/-}$ vs. wildtype littermate kidneys yielded 11. Four were shared between settings, with all four lower in PGC1α$^{-/-}$ and post-ischemic kidneys (FIG. 1G,H, FIGS. 7A,B).

Figure 7C:
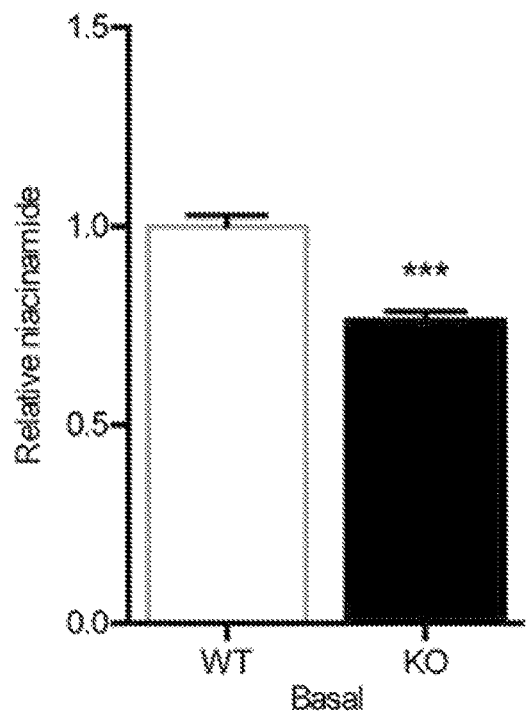
Figure 7D:
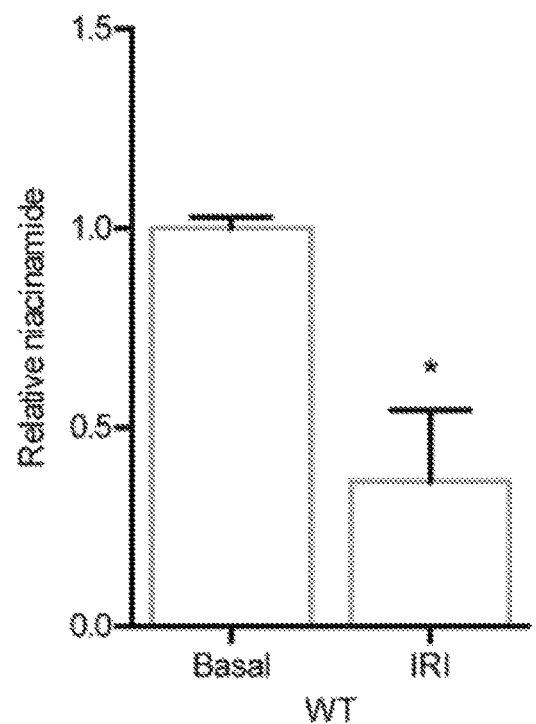
Figure 7E:
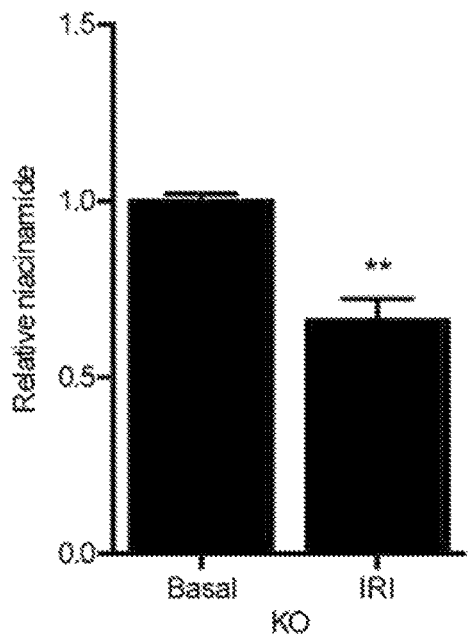
Figure 7F:
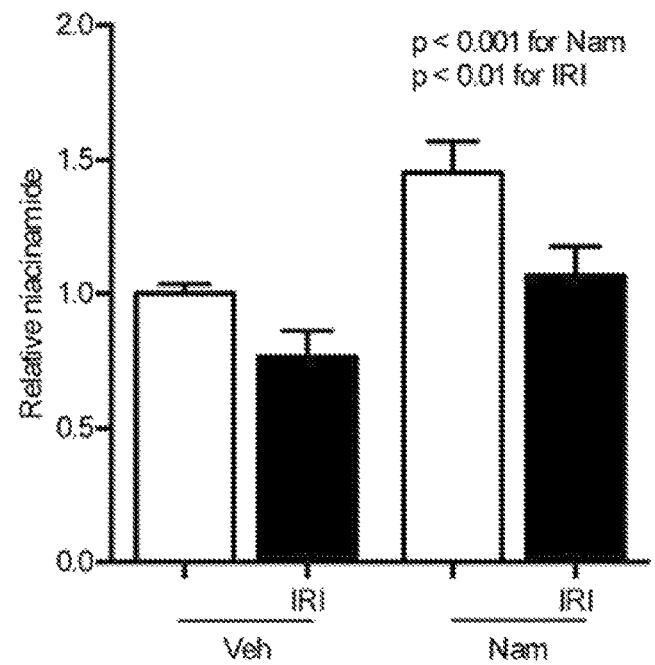
Figures 7G, 7H:
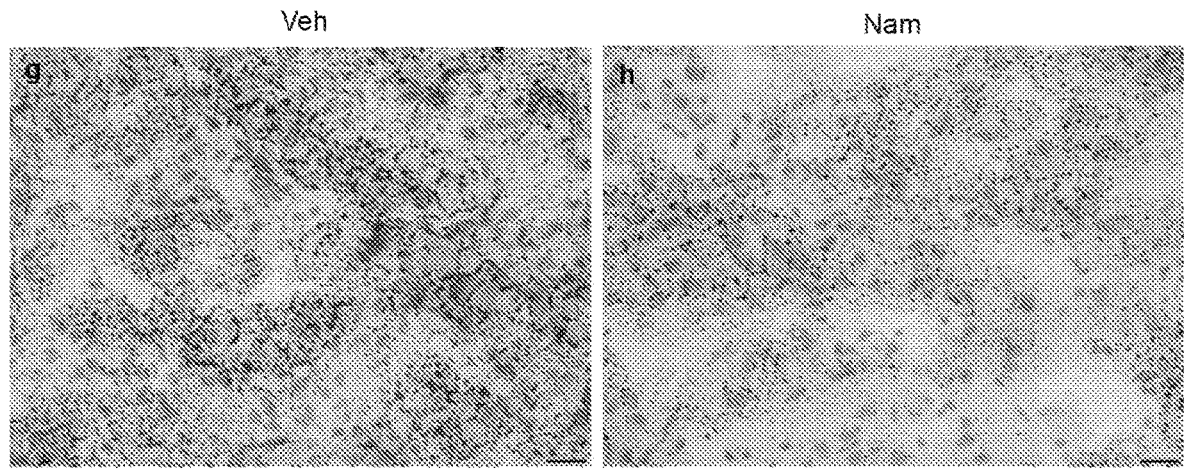
Figure 8A:
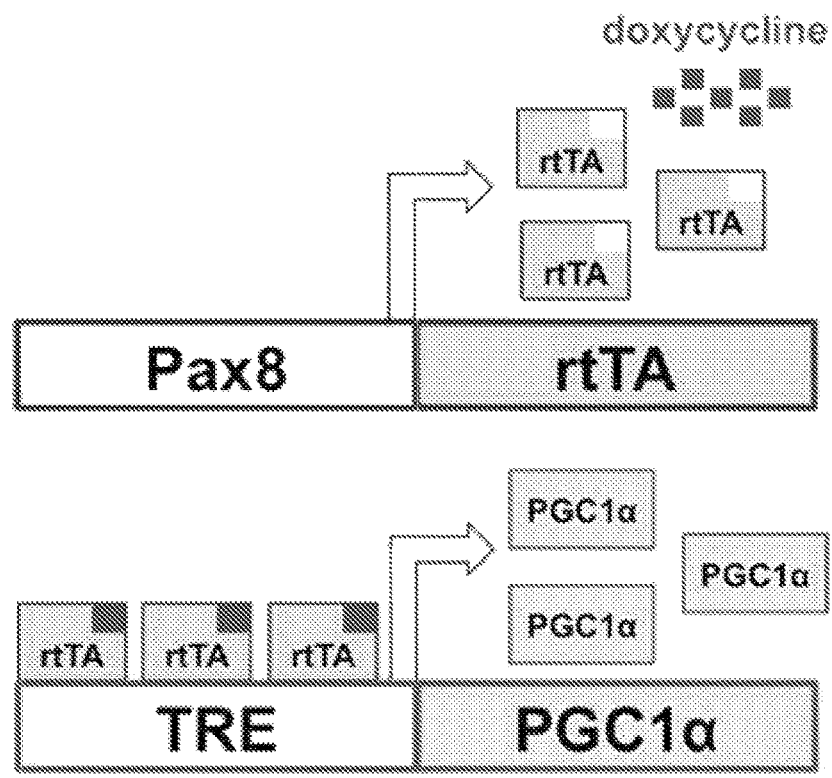
Figure 8B:
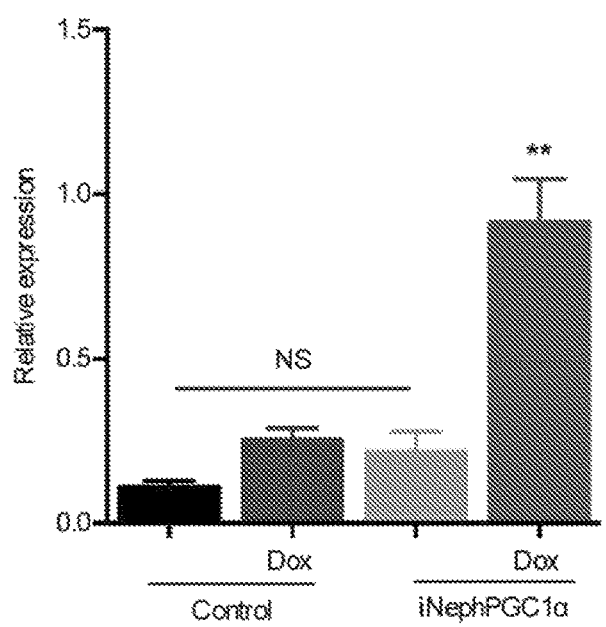
Figure 8C:
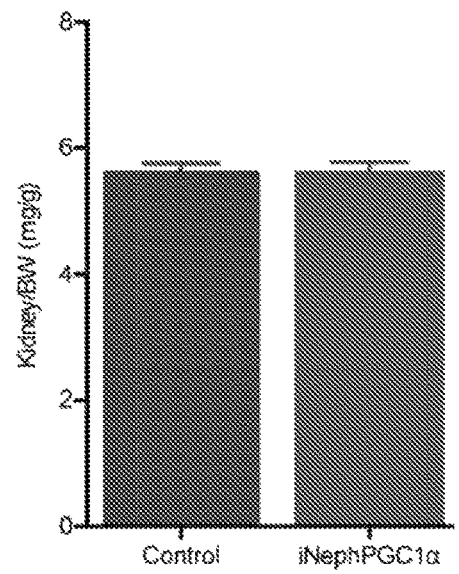
Figure 8D:
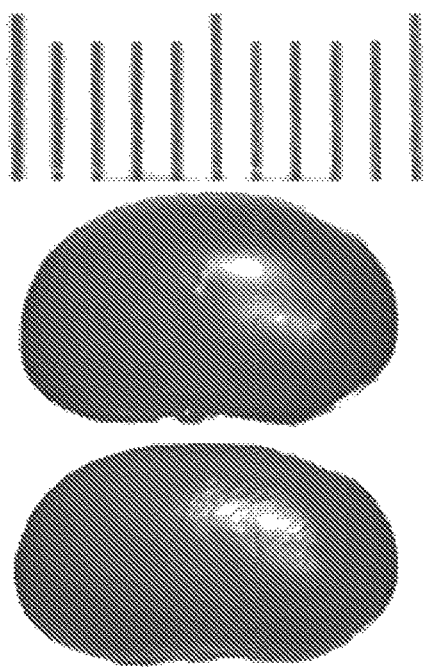
Figure 8J:
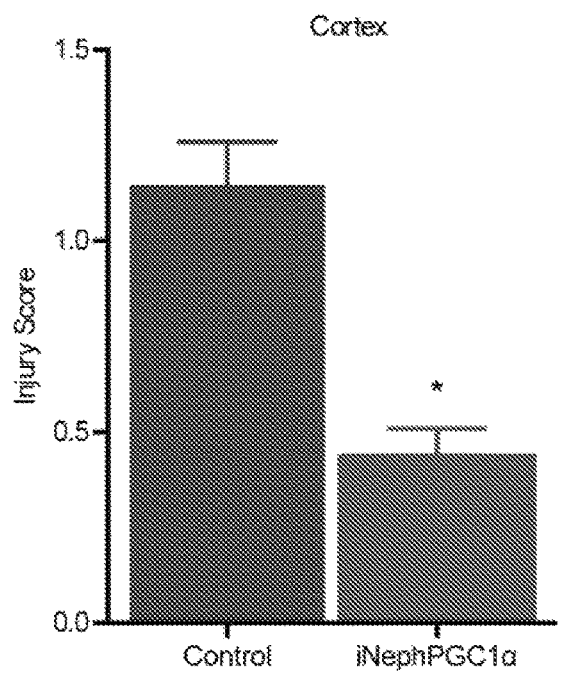
Figure 8K:
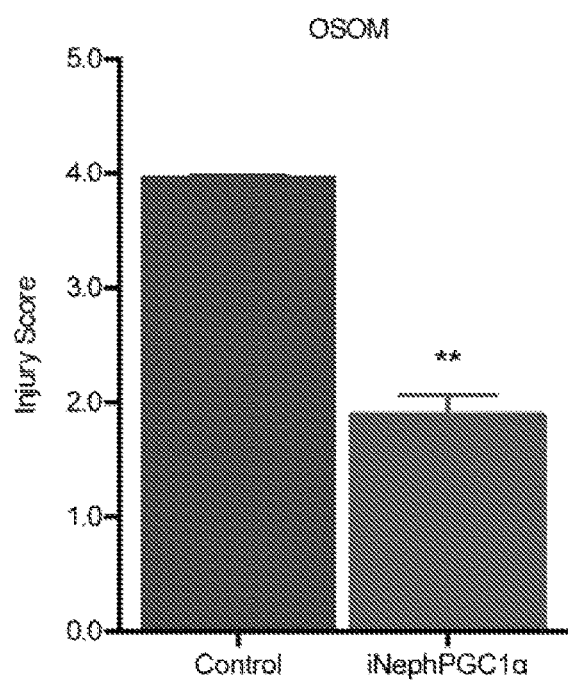

Of these, carnitine deficiency in PGC1α$^{-/-}$ and post-ischemic kidneys supported mitochondrial involvement in both situations. Deficiency of betaine and choline, two osmolytes essential for cell volume maintenance in the uniquely hypertonic renal environment, was not unanticipated. We therefore focused on niacinamide (Nam), the predominant mammalian precursor to synthesize the energy carrier NAD needed for fatty acid oxidation (FAO) (Collins et al. J Biol Chem 1972; 247:778-83). After confirming the metabolomics results (FIGS. 7C-E), we tested the effect of Nam supplementation. Exogenous Nam increased renal Nam (p<0.001), normalized post-ischemic fat accumulation, and completely prevented post-ischemic AKI in PGC1α$^{-/-}$ mice (FIG. 1I, FIGS. 7F-H), implicating this metabolite as an unexpected effector of PGC1α.

Figure 9A:
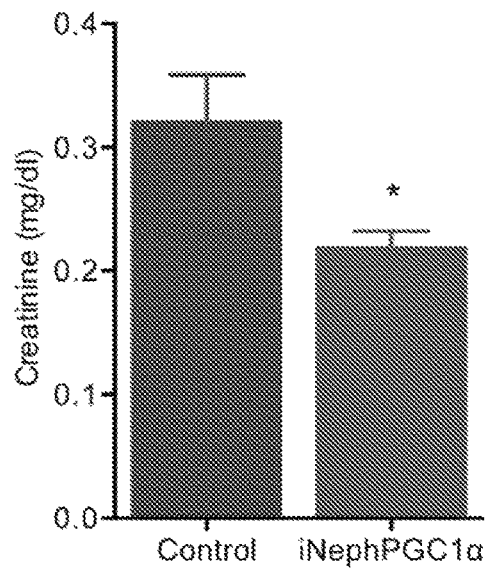
FIGS. 9A-B: Renal protection in systemic inflammation conferred by renal tubular epithelial, but not endothelial, PGC1α. A, Serum creatinine 24 h after bacterial endotoxin injection (LPS O111:B4), n=9/group. B, Serum creatinine 24 h after bacterial endotoxin (LPS O111:B4) in endothelial-specific (VEC=VE-cadherin) PGC1α transgenic mice (VEC-tTA×TRE-PGC1α), n=5/group. Error bars SEM, *$p<0.05$.
Figure 9B:
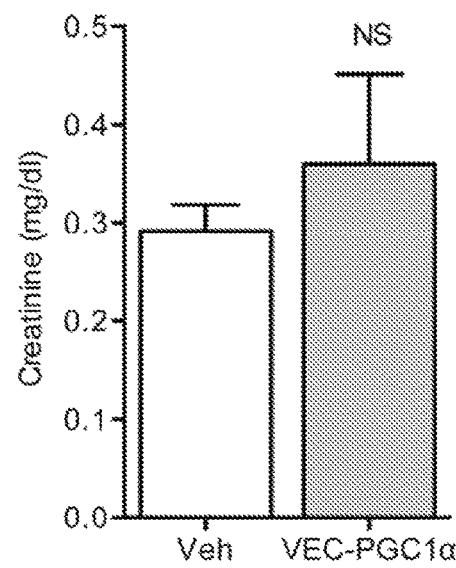

To probe the robustness of PGC1α's relation to Nam, fat accumulation, and renal function, we developed an inducible tubular epithelial transgenic model using the well-validated Pax8 promoter (iNephPGC1α) (Traykova-Brauch et al. Nat Med 2008; 14:979-84). Heterologous PGC1α was tightly controlled without leaky gene expression; organ size and mass were indistinguishable; and mitochondrial abundance increased—as assessed by comparing mitochondrial to nuclear DNA and mitochondrial gene products to cytosolic gene products-without altering ultrastructural morphology or the anatomical distribution favoring cortex and outer stripe of the outer medulla (FIG. 2A-C, FIGS. 8A-I). iNephPGC1α mice tolerated renal ischemia more successfully, achieving better survival (p=0.0039), more preserved function (p<0.0001), better kidney perfusion, and less tubular injury (FIG. 2D-K, FIGS. 8J,K). Sham-operated mice experienced no significant change in creatinine or reduced survival. Renal Nam was higher in post-ischemic iNephPGC1α mice, and post-ischemic fat accumulation was markedly reduced compared to controls (p<0.0001, FIG. 2L-Q). Renal protection in iNephPGC1α mice was shared across distinct models as post-inflammatory renal injury was also attenuated (FIG. 9A). PGC1α's effect appeared to be cell-type specific as endothelial over-expression conferred no renoprotection (FIG. 9B).

Figure 3C:
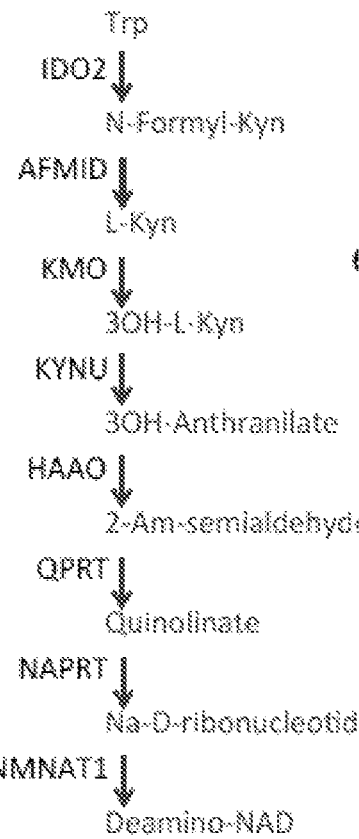
FIGS. 3A-P: Nam induces β-OHB downstream of PGC1α to augment PGE$_2$. A, Renal RNA sequencing 24 h after IRI or sham operation in controls vs. iNephPGC1α mice with enumerated transcripts. B, Pathway analysis of 1160 transcripts unique to post-ischemic iNephPGC1α mice graphed by $-\log_{10}$[Benjamini-Hochberg-corrected p-value]. Dashed line at p<0.05. C, de novo NAD biosynthetic pathway adapted from KEGG: Kyoto Encyclopedia of Genes and Genomes (Ogata et al., Nucleic Acids Res. 1999 Jan. 1; 27(1):29-34). Trp=tryptophan, Kyn=kynurenine, Am=amino, Na=nicotinate. D-F, graphs showing the NAD biosynthetic pathway being (d) oppositely modulated by PGC1alpha loss- vs. gain-of-function and (e) being attenuated in IRI, a model of acute kidney injury in which PGC1alpha expression also falls; and (f) in iNephPGC1α vs. controls (n=6/group). P-values by ANOVA. G, Relative renal Nam and NAD 4 h after indicated Nam dose. P-value by ANOVA. H, Conditioned-media-PGE$_2$ of renal tubular cells after HCAR2 knockdown with and without HCAR2 stimulation (+, niacin 10 mM, n=6/group). I, PGE$_2$ from renal cells following Nam (1 µM for 24 h) with and without NAMPT inhibitor FK866 (10 nM, n=6/group). J-L, Intracellular NAD, conditioned-media beta-hydroxybutyrate (β-OHB), and conditioned-media PGE$_2$ in PGC1α knockdown cells (n=6/group). M-O, Relative renal NAD, β-OHB, and PGE$_2$ in control vs. iNephPGC1α mice (n=6/group). *p<0.05, p<0.01, *p<0.001. P, Renal epithelial PGC1α coordinately upregulates de novo NAD biosynthesis, in the absence of which Nam is utilized through the NAMPT-salvage pathway to generate NAD. Consequently, β-OHB accumulates, which signals HCAR2 to induce PGE$_2$. Error bars SEM.
Figure 3D:
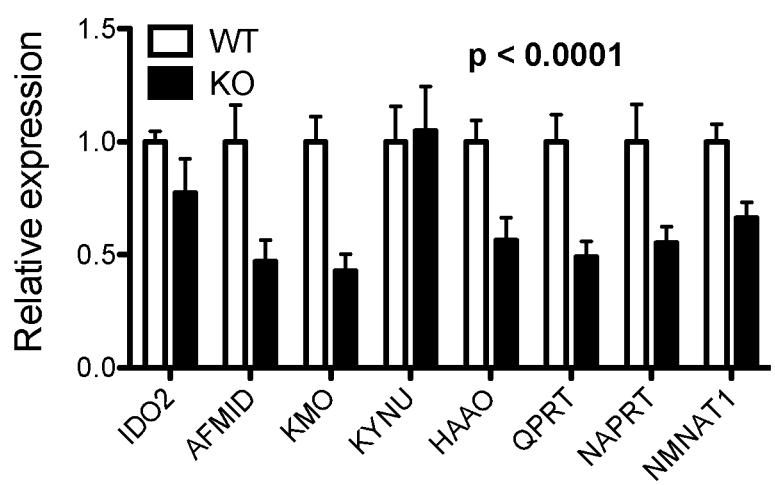
Figure 3E:
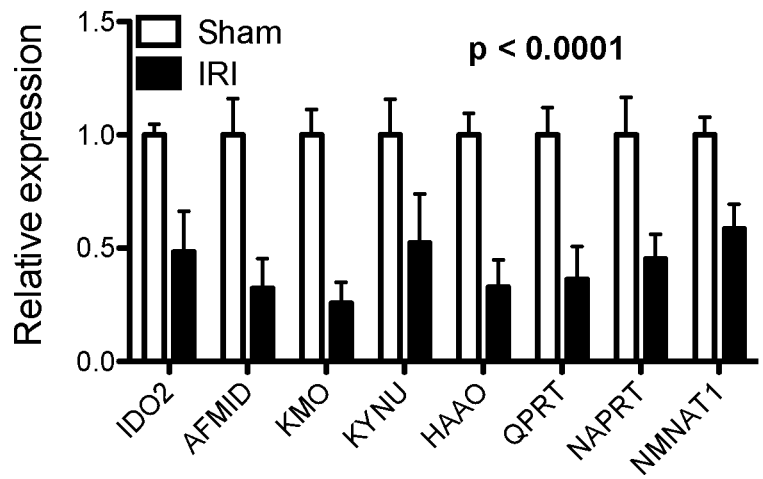
Figure 3F:
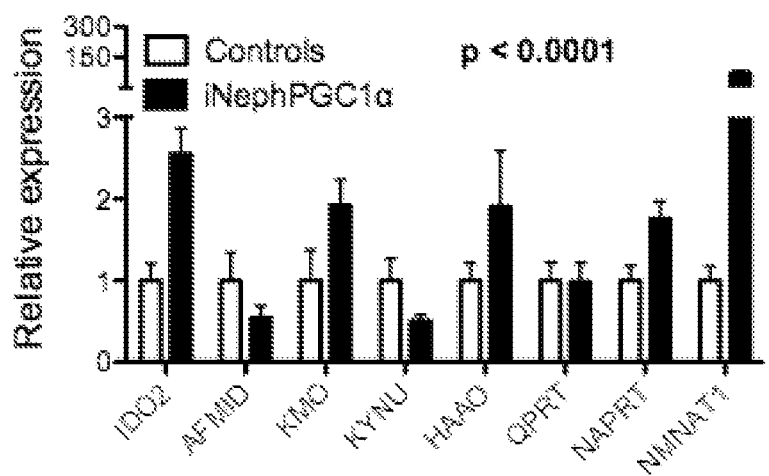
Figure 10A:
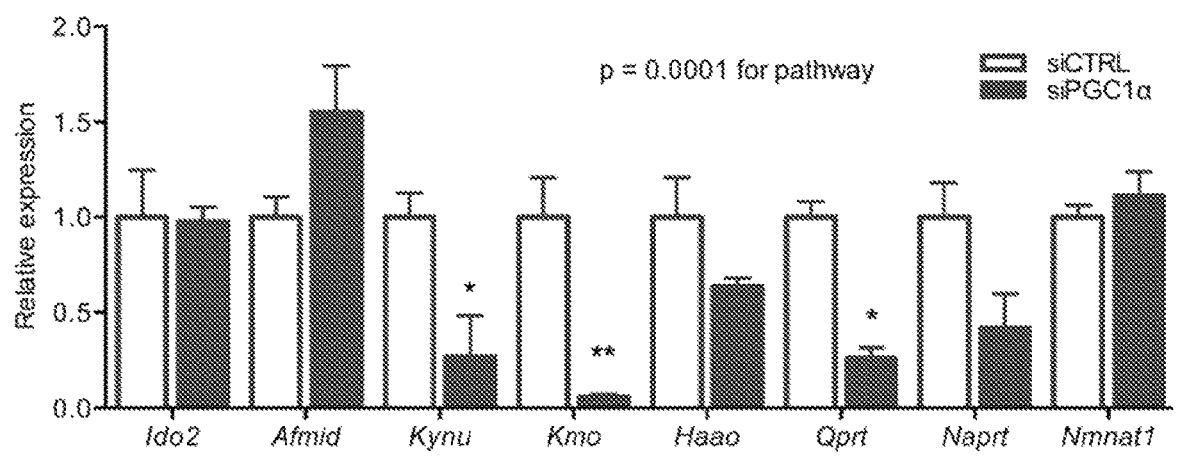
FIGS. 10A-H: PGC1α-dependent de novo NAD biosynthesis and NAD-dependent accumulation of j-OHB and $PGE_2$. A, Gene expression for de novo NAD biosynthetic pathway in renal tubular cells 48 h after control vs. PGC1α knockdown (n=3/group). The gene expression set corresponds to the eight transcripts whose abundance was measured in kidney homogenates in FIG. 3. $P=0.0001$ by two-way ANOVA with Bonferroni-corrected comparisons as indicated. B, Correlation of renal Nam vs. renal NAD in mice treated with vehicle or different doses of Nam (100-400 mg/kg IP×1). Arbitrary units on X- and Y-axes. C, Renal β-OHB concentrations in kidneys of mice following vehicle (Veh) vs. Nam treatment (400 mg/kg IP×4 d) with and without IRI 24 h prior to tissue collection (n=5/group). P-value by two-way ANOVA. Dashed line indicates normal circulating concentration of β-OHB. D, Dosing for siRNA against HCAR2 in renal tubular cells. E, Dose-inhibition curve in renal tubular cells for $PGE_2$ release following 24 h of mepenzolate bromide at the indicated concentrations (n=3 replicates per concentration). (Rask-Andersen et al., Nature reviews. Drug discovery 10, 579-590 (2011); Singh et al., Cell host & microbe 12, 669-681 (2012); Feingold et al., J Lipid Res 55, 2501-2508 (2014)). F,G Intracellular Nam and secreted β-OHB for renal tubular cells following treatment with Nam (1 μM for 24 h) with or without pre-treatment with the NAMPT inhibitor FK866 (10 nM, n=6/group). H, $PGE_2$ in conditioned media of renal tubular cells after control vs. PGC1α knockdown and with and without exogenous β-OHB application (+, 5 mM, n=6/group, p values vs. control group). Error bars SEM, *$p<0.05$, $p<0.01$, *$p<0.001$, and ****$p<0.0001$.

RNA sequencing identified 1160 transcripts associated with PGC1α-dependent renoprotection (FIG. 3A). The pathways most over-represented related to intermediary metabolism (FIG. 3B). Closer examination revealed that de novo NAD biosynthetic enzymes were coordinately regulated, induced in uninjured iNephPGC1α kidneys and suppressed in post-ischemic or uninjured PGC1α$^{-/-}$ kidneys (FIG. 3C-F). PGC1α's effect on the de novo pathway was cell-autonomous as knockdown in isolated renal tubular cells was sufficient to suppress the pathway (p=0.0001, FIG. 10A).

Figure 3G:
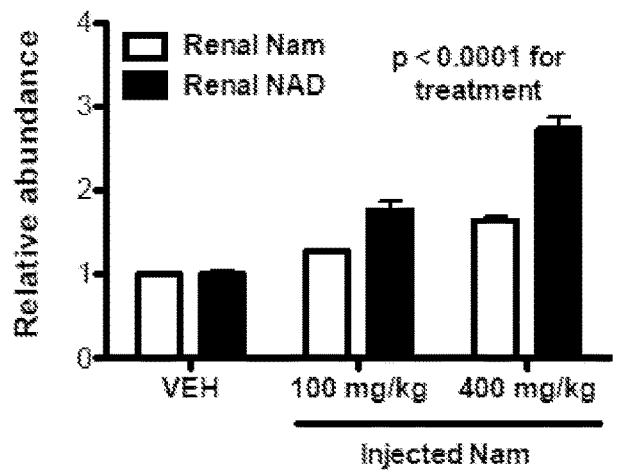
Figure 3H:
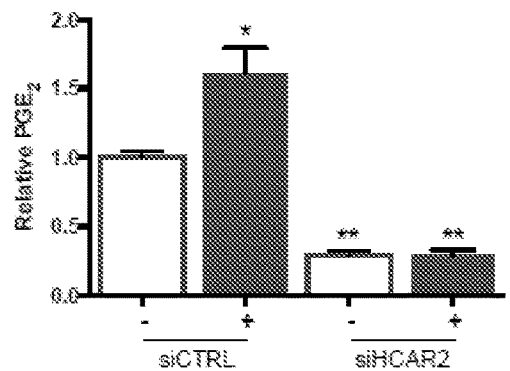
Figure 3I:
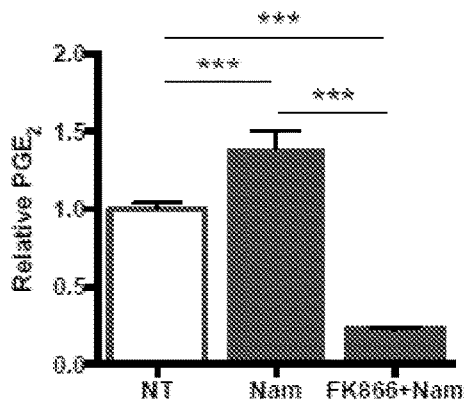
Figures 3J, 3K, 3L:
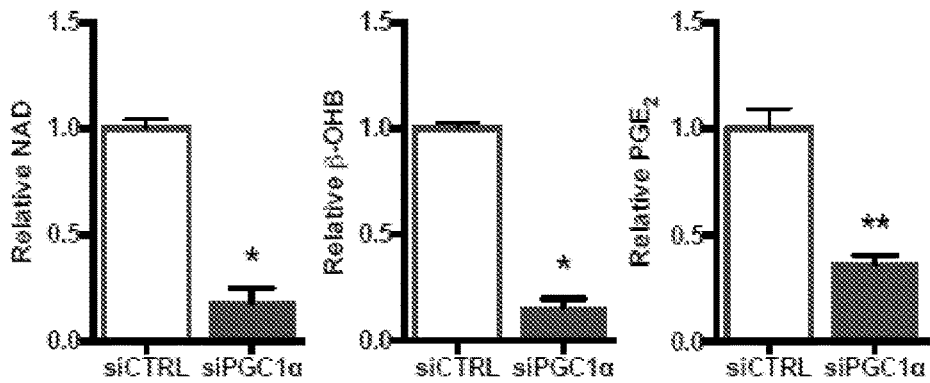
Figure 10B:
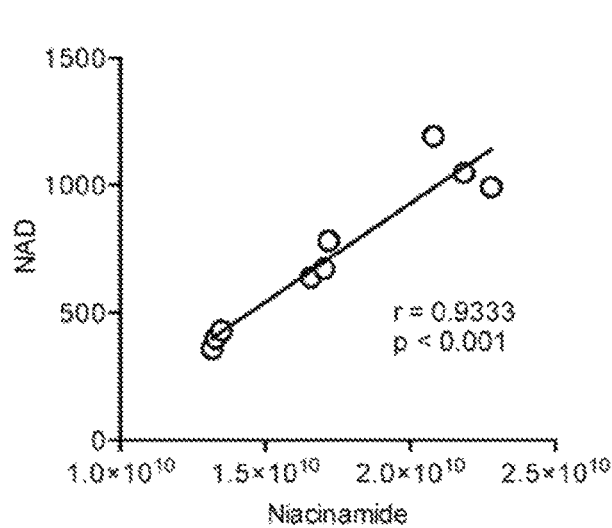
Figure 10C:
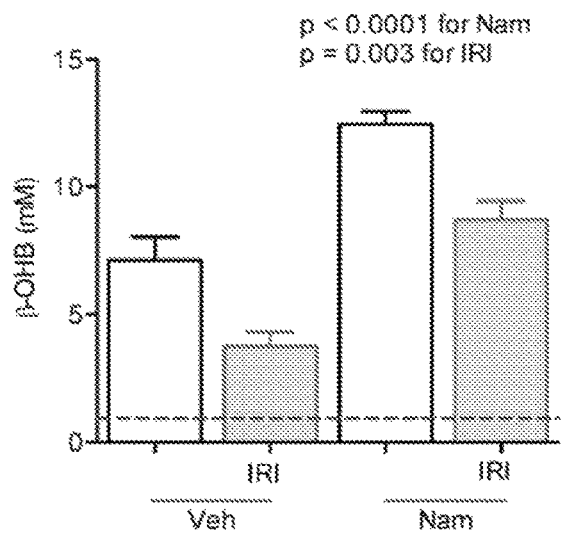
Figure 10D:
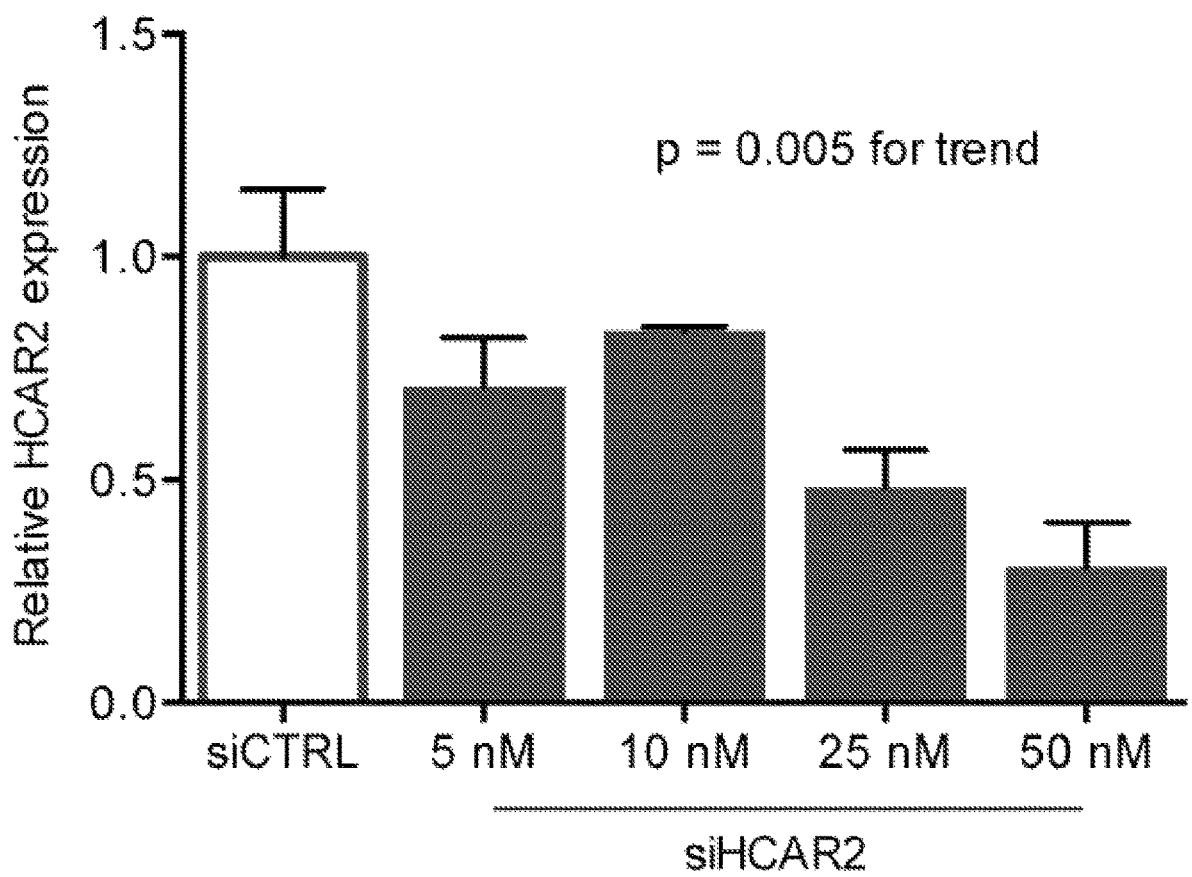
Figure 10E:
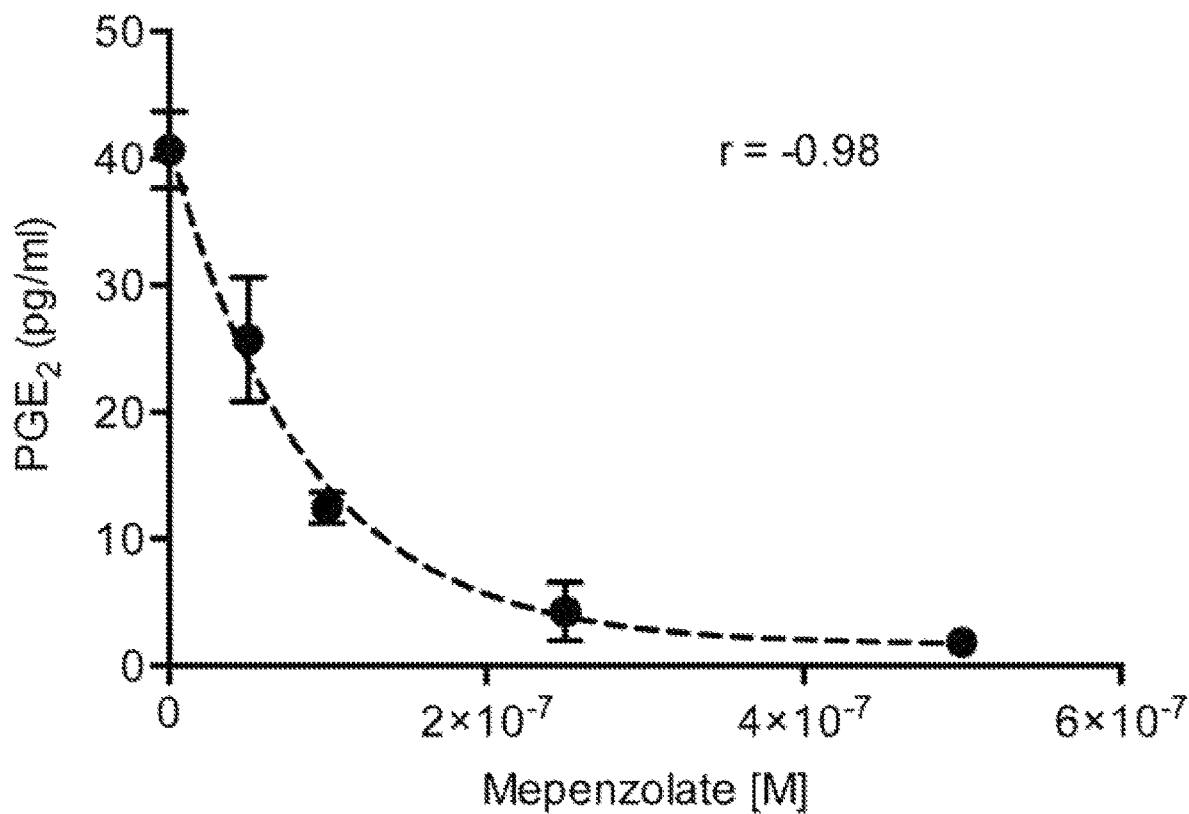
Figure 10F:
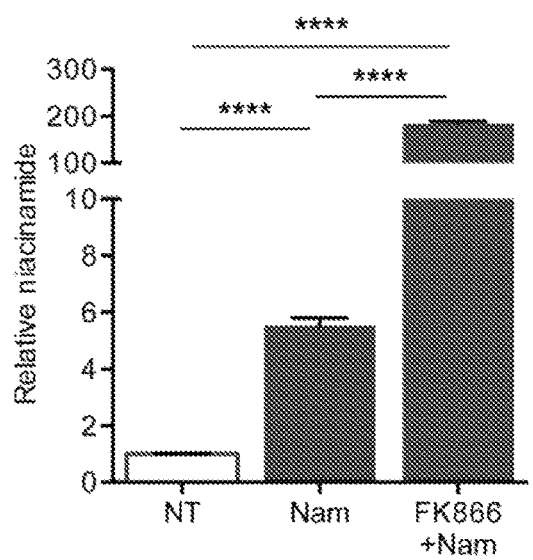
Figure 10G:
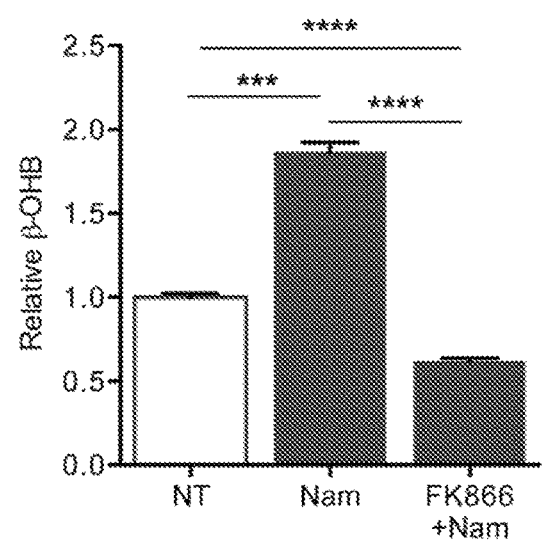
Figure 10H:
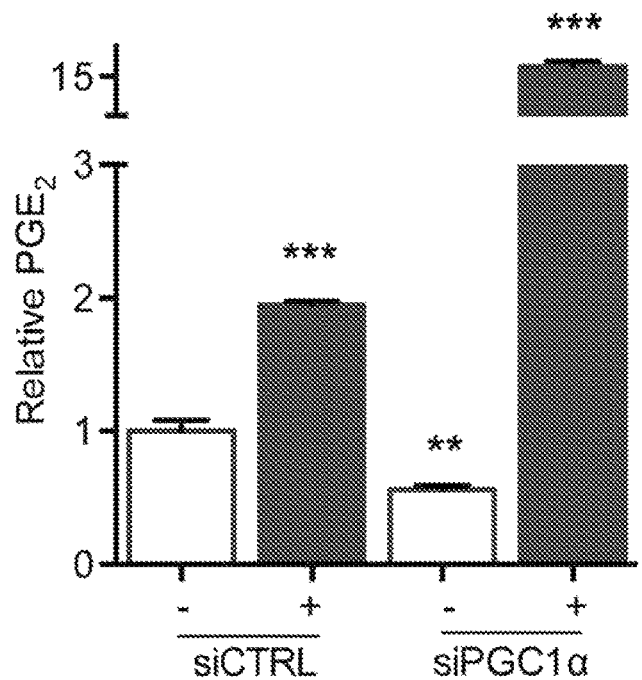

As epithelial PGC1α defended renal function and resolved post-ischemic fat accumulation, we hypothesized that protection from AKI may relate to Nam, NAD, and fatty acid utilization. Indeed, exogenous Nam dose-dependently increased renal NAD and drove local accumulation of the fatty acid breakdown product β-OHB to ~ten-fold higher than normal circulating concentrations (p<0.0001, FIG. 3G and FIGS. 10B,C). β-OHB activates HCAR2, a G-protein coupled receptor that induces the renoprotective prostaglandin PGE2. (Hanson et al. J Clin Invest 2010; 120:2910-9; Vafai et al. Nature 2012; 491:374-83). Silencing or chemical inhibition of HCAR2 markedly reduced both basal and ligand-dependent PGE2 secretion (FIG. 3H, FIGS. 10D,E). Nam augmented PGE2 secretion, requiring conversion to NAD via the enzyme NAMPT to do so (FIG. 3I, FIGS. 10F,G) (Revollo et al. J Biol Chem 2004; 279:50754-63). Silencing of PGC1α reduced each intermediate, lowering the cellular NAD and secreted β-OHB and PGE2 (FIG. 3J-L). In PGC1α-silenced cells, excess β-OHB was still able to induce PGE2 secretion (p<0.0001, FIG. 10H). Finally, renal levels of each component mirrored the cellular results, with opposing effects of PGC1α deficiency and excess on NAD, β-OHB, and PGE2 (FIG. 3M-O, FIGS. 11A-C). Together, these results implicated PGC1α-dependent NAD production as an important determinant of cellular metabolism that induces renoprotective molecules (FIG. 3P).

Figure 4C:
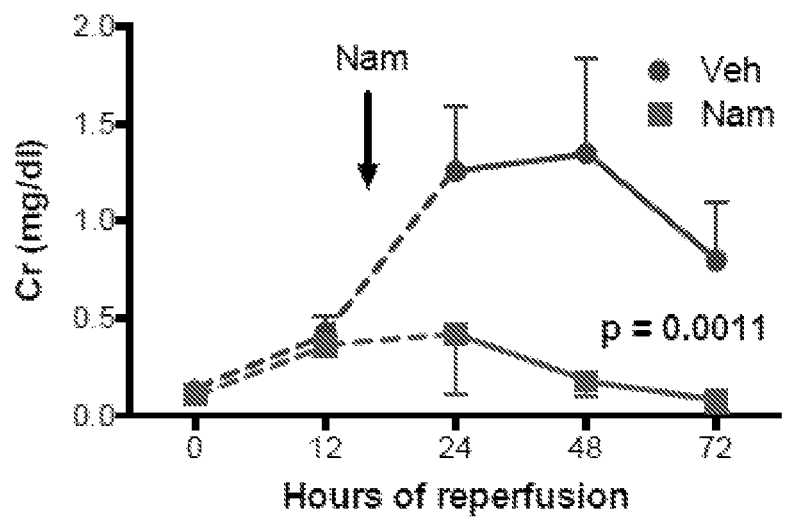
Figure 4D:
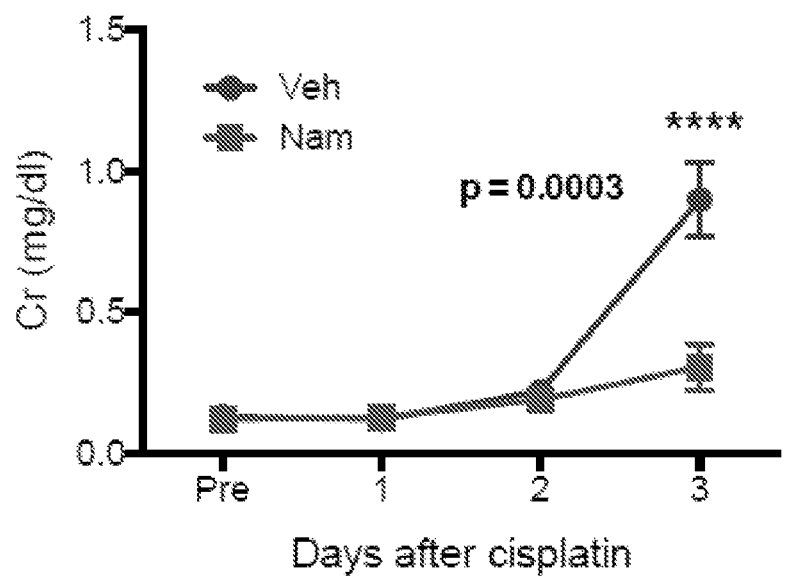
Figure 4E:
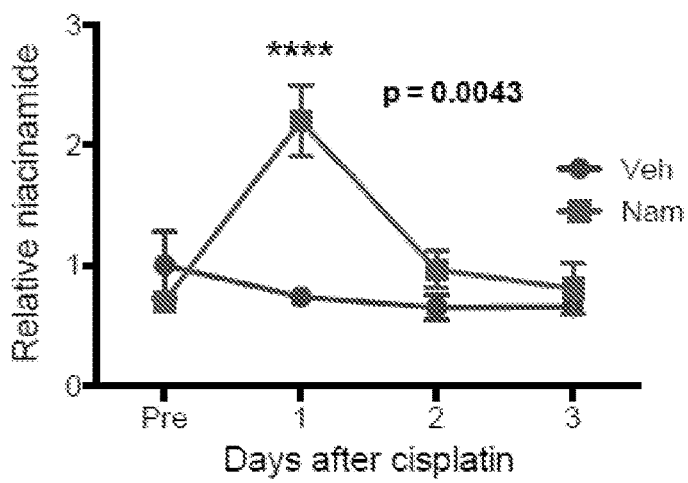
Figure 4H:
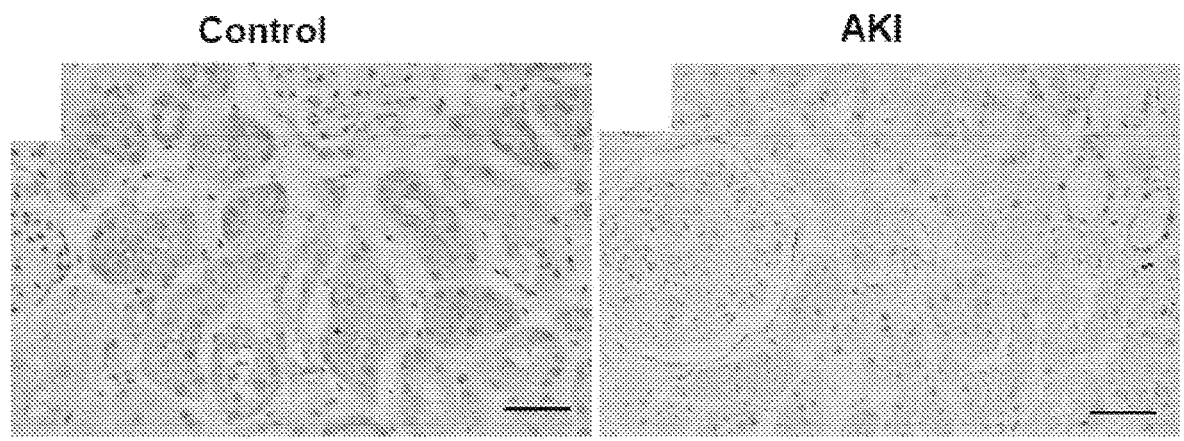
Figure 4H:
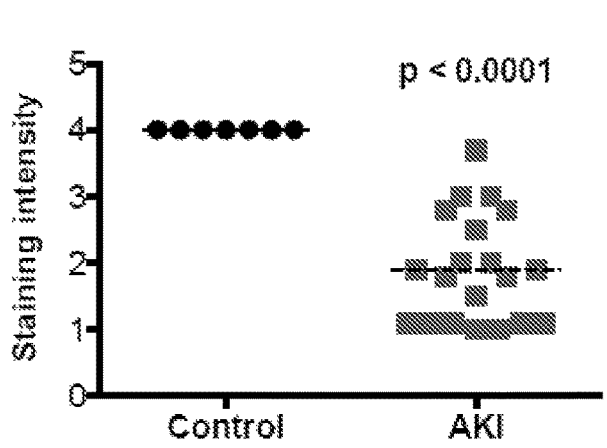
Figure 11A:
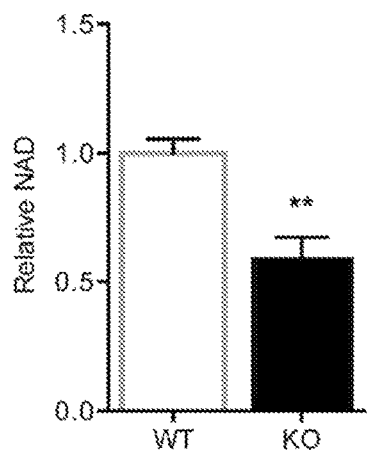
FIGS. 11A-G: Effects of PGC1α on renal metabolites and features of cisplatin nephrotoxicity. A-C, Relative renal NAD, β-OHB, and $PGE_2$ concentrations in WT littermates vs. PGC1α$^{-/-}$ (KO) mice (n=6/group). D, Serum creatinine in genetic control mice for iNephPGC1α 24 h after IRI with vehicle vs. mepenzolate (MPN, 10 mg/kg IP) treatment (n=5/group). E, Serum creatinine in genetic control mice for iNephPGC1α 24 h after IRI with vehicle vs. indomethacin (INDO, 10 mg/kg IP) treatment (n=6/group). F, Transmission EM with cytochrome c oxidase enzyme histochemistry of proximal tubular cell 24 h following cisplatin exposure (25 mg/kg IP) demonstrating mitochondrial injury. Scale bar 500 nm. G, Relative renal Nam concentrations following cisplatin as in F. Error bars SEM, *$p<0.05$, $p<0.01$, *$p<0.001$.
Figure 11B:
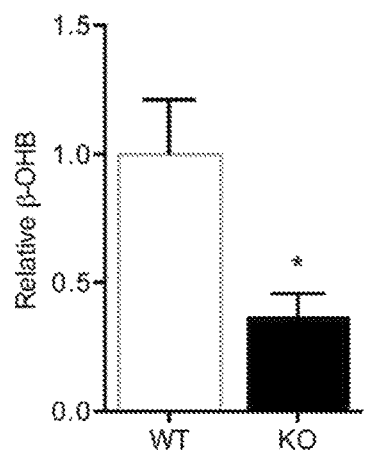
Figure 11C:
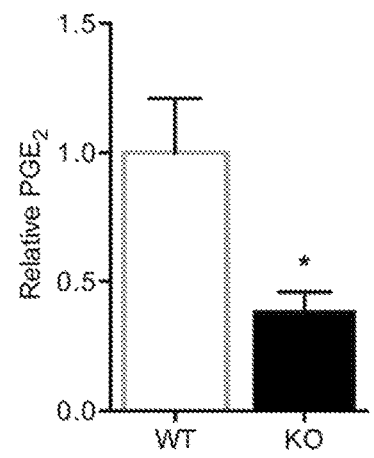
Figure 11D:
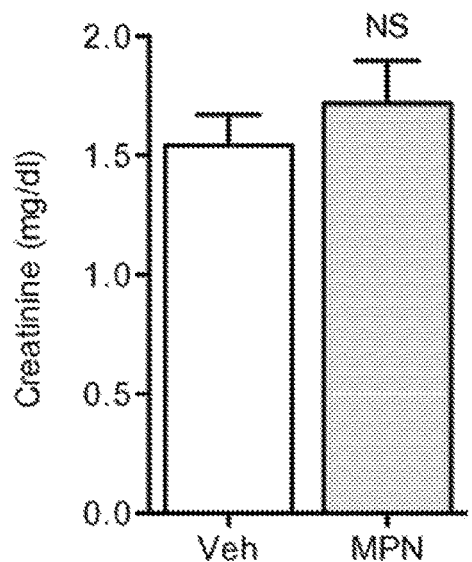
Figure 11E:
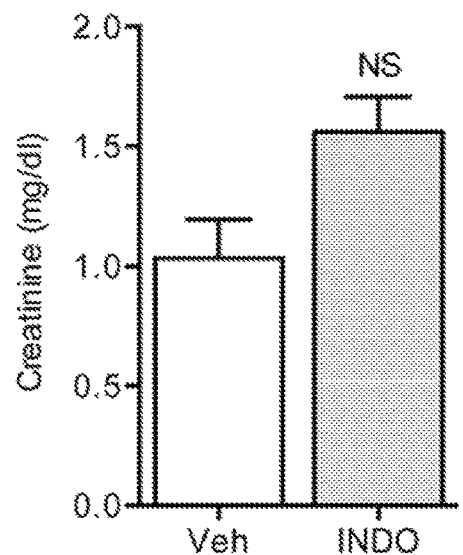
Figure 11F:
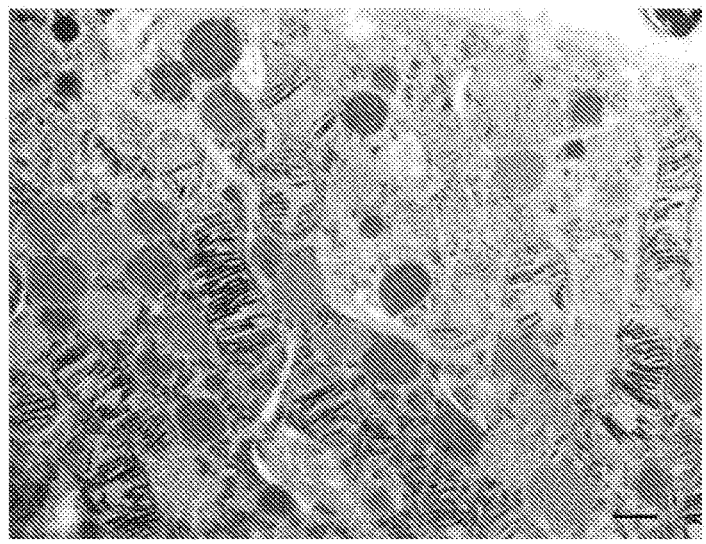
Figure 11G:
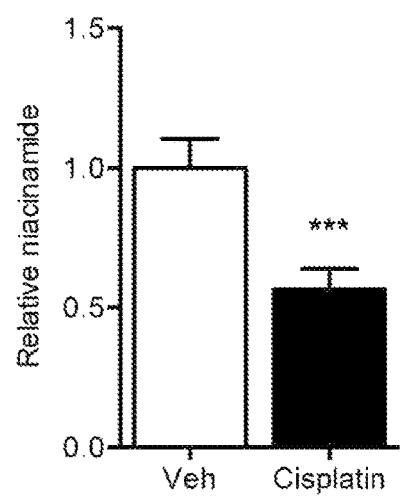

To test this further, we inhibited β-OHB signaling with mepenzolate bromide or prostaglandin synthesis with indomethacin in iNephPGC1α mice subjected to ischemia. Renal protection was similarly abolished in either setting, confirming their roles as PGC1α effectors (FIG. 4A,B, FIG. 11D,E). Since Nam prevented ischemic AKI in PGC1α$^{-/-}$ mice, we then asked whether Nam has a broader therapeutic role. Nam administered after established AKI and bilateral renal ischemia significantly improved renal function (p=0.0011, FIG. 4C). We also observed that renal Nam declined following cisplatin, a chemotherapy whose use is limited by nephrotoxicity and whose injurious mechanism involves mitochondria but is considered distinct from ischemia (FIGS. 11F,G). Nam supplementation prevented cisplatin-induced AKI (FIG. 4D,E).

These results were confirmed in human tissues. PGC1α expression was evaluated by immunostaining in archival renal biopsies taken from normal sections of nephrectomy specimens (Control, FIG. 4F) and individuals with AKI (FIG. 4G). Staining intensity was scored by a single operator blinded to underlying diagnosis by evaluating 10 random sections per specimen and assigning a staining intensity score (4=strongest, 1=weakest) and taking the average of those 10 readings to generate a composite score per specimen. The results show that in human AKI PGC1α expression was strongly suppressed, even in histologically normal regions of renal tissue (FIG. 4F-H, FIGS. 12A-F), mirroring the AKI-induced suppression of PGC1α observed in experimental models (FIGS. 5C and 11). These results show that PGC1α is a negatively regulated target in AKI.

Figure 15A:
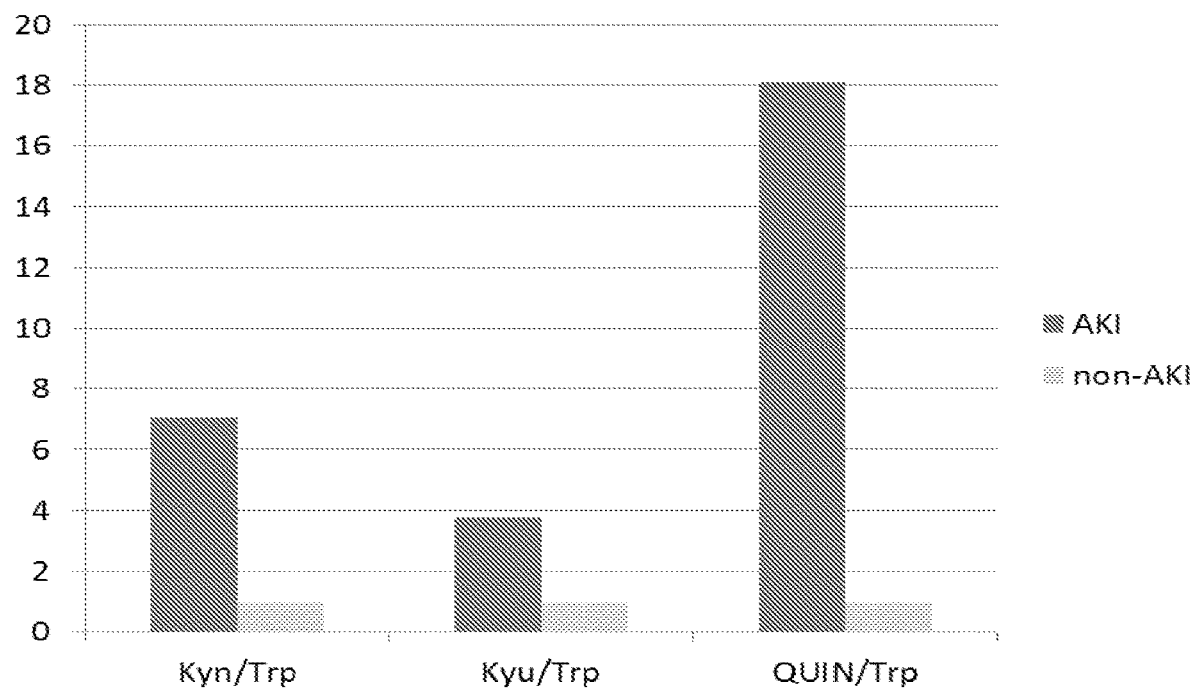
FIGS. 15A-C: Convergent evidence across model systems implicating metabolic balance as an indicator of PGC1alpha status. (A) Urinary concentrations of kynurenine (Kyn), kynurenic acid (Kyu) and quinolinate (Quin) benchmarked by urinary tryptophan (Trp) concentration across n=10 human subjects with AKI and 10 non-AKI human control urines. The mean of the non-AKI group was used to normalize all measurements. $P<0.01$ for each pairwise comparison. (B) The PGC1alpha-NAD pathway described herein converts tryptophan (Trp) to NAD via the intermediate quinolinic acid (Quin). A reduction of PGC1alpha could be hypothesized to favor a build-up of Trp and attenuation of Quin. (C) Metabolic results from renal cells in which PGC1alpha is reduced by RNAi (siPGC1a, left), from kidney homogenates of PGC1alpha knockout mice (middle), and from urine of PGC1alpha KO mice (right) all show a robust and conserved shift in the balance between Quin and Trp, supporting their use as non-invasive indicators of PGC1alpha-NAD status in the kidney is a graph showing
Figure 15B:
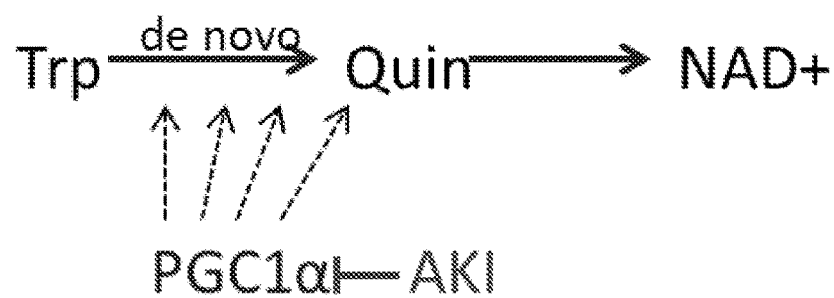
Figure 15C:
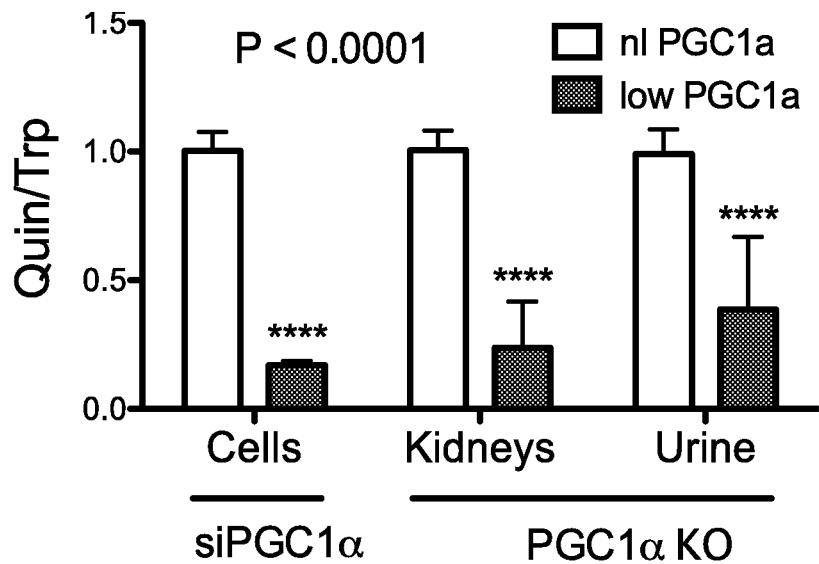

The enzymatic pathway that converts tryptophan to NAD is shown in FIG. 3C. In normal healthy individuals, Trp→Kyn→Kyu→Quin→NAD in normal health. Therefore, it was hypothesized that failure to convert Trp to NAD in AKI could result in build-up of intermediates (Kyn, Kyu, Quin) that spills over into urine. As shown in FIGS. 15A and C, urinary concentrations of kynurenine (Kyn), kynurenic acid (Kyu) and quinolinate (QUIN), benchmarked by urinary tryptophan (Trp) concentration, were significantly increased in AKI samples versus normal. Convergent evidence across model systems implicates metabolic balance as an indicator of PGC1alpha status. The PGC1alpha-NAD pathway that we have described converts tryptophan (Trp) to NAD via the intermediate quinolinic acid (Quin) (FIG. 15B). A reduction of PGC1alpha could be hypothesized to favor a build-up of Trp and attenuation of Quin. Metabolic results from renal cells in which PGC1alpha is reduced by RNAi (siPGC1α, FIG. 15C, left), from kidney homogenates of PGC1alpha knockout mice (FIG. 15C, middle), and from urine of PGC1alpha KO mice (FIG. 15C, right) all show a robust and conserved shift in the balance between Quin and Trp, supporting their use as non-invasive indicators of PGC1alpha-NAD status in the kidney The present results identify PGC1α as a pivotal mediator of renal resistance to acute stressors. By linking oxidative metabolism in the epithelium to overall organ function, the proposed pathway provides new insight into a longstanding observation, namely the exquisite sensitivity of the kidney to ischemia and other insults. More fundamentally, the results implicate NAD biosynthesis as a coordinately regulated target of PGC1α.

Figure 16A:
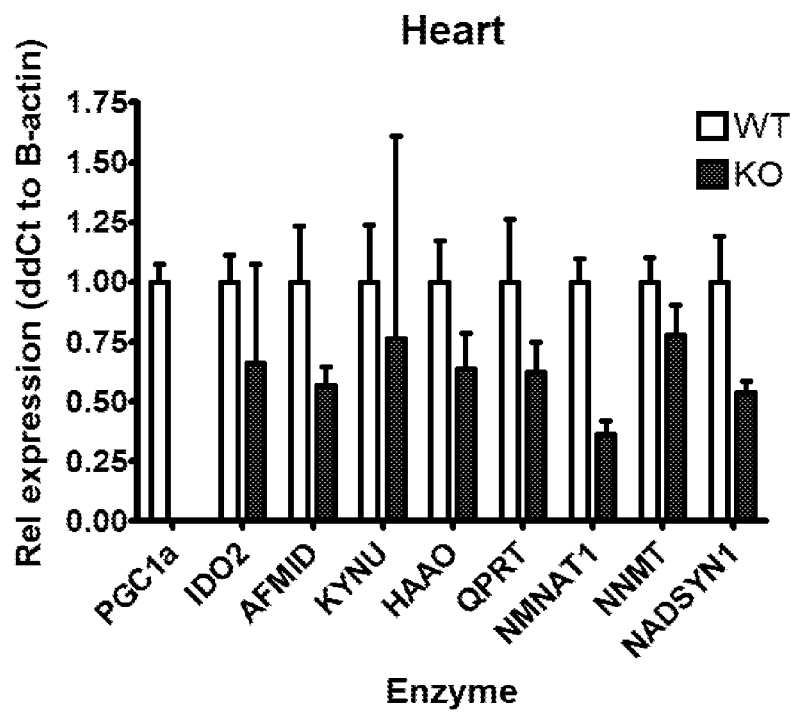
FIGS. 16A-B: Expression of PGC1alpha and downstream enzymes in the NAD pathway measured by real-time PCR in heart (16A) and brain (16B) homogenates of PGC1alpha knockout mice (KO) and wildtype (WT) littermates.
Figure 16B:
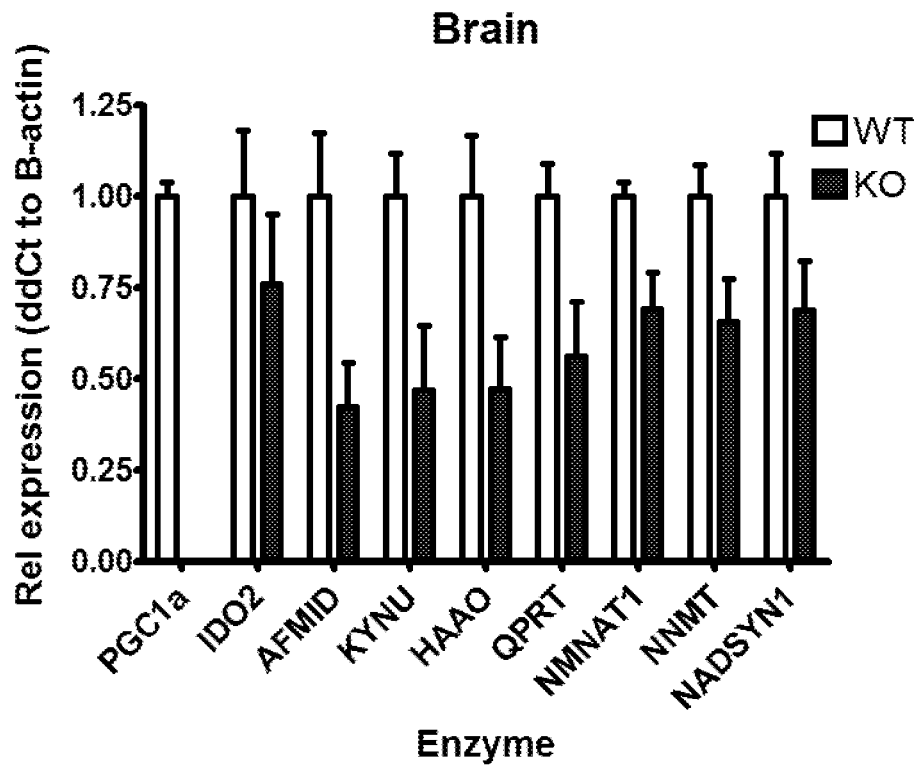

Example 1.2. PGC1α Deficiency Lowers Expression of Key Enzymes that Synthesize NAD The effects of PGC1alpha deficiency on expression levels of enzymes involved in the synthesis of NAD, specifically Ido2, Afmid, Kynu, Kmo, Haao, Qprt, Nmnat1, NNMT, and Nadsyn1 were evaluated by real-time PCR in the kidney, heart, and brain of PGC1alpha knockout mice. As shown in FIGS. 16A-B, PGC1alpha deficiency (KO) sufficient to lower expression of key enzymes that synthesize NAD. Furthermore, a stronger PGC1alpha-dependent reduction in expression levels of those enzymes was seen in the brain and the heart than in the kidney, where excess PGC1alpha and PGC1alpha mimetic therapy with Nam is shown to be beneficial or organ protection. This suggests that a similar mechanism may be at work in those organs, indicating that the present methods can be used to reduce post-ischemic injury in brain and cardiac tissues.

Figure 17A:
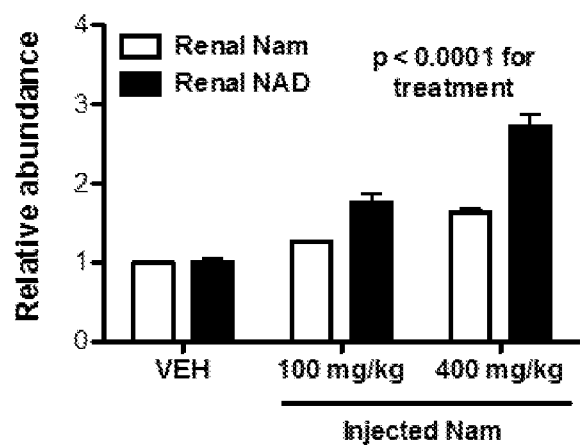
FIG. 17A: Intraperitoneal injection of the indicated dose of niacinamide (Nam) or vehicle solution (VEH) followed 4 hrs later by assessment of renal Nam and NAD abundances, indicating that Nam supplementation can increase renal NAD levels.
Figure 17B:
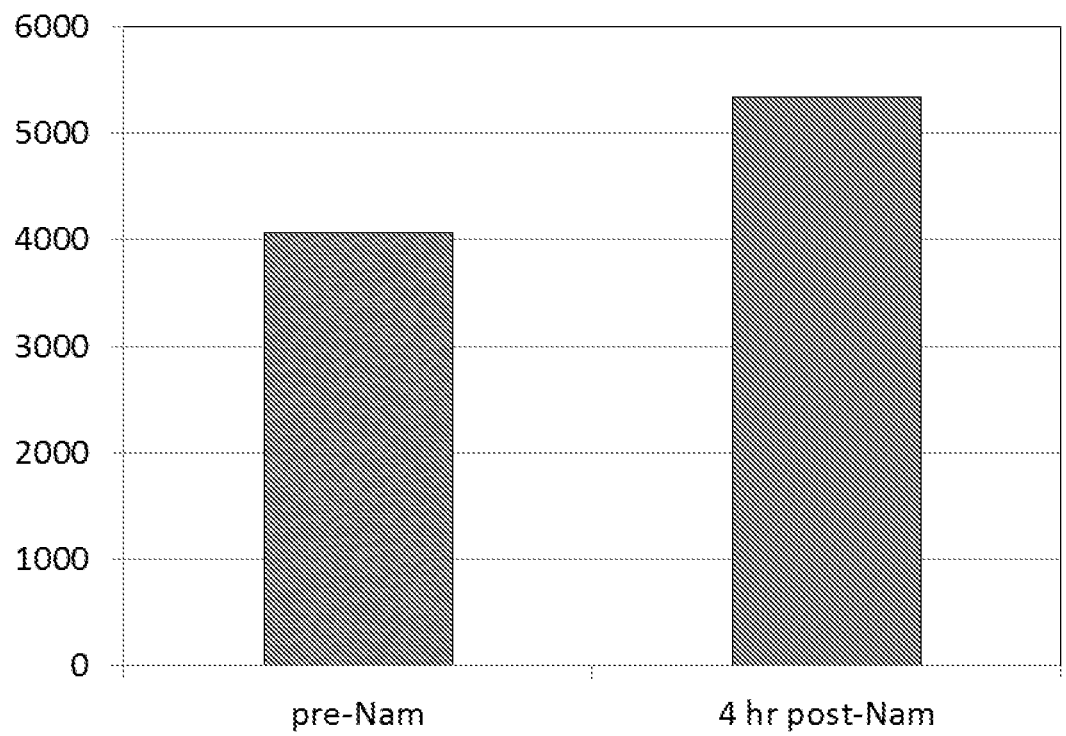
FIG. 17B: Niacinamide (Nam) was administered (400 mg/kg intraperitoneal×1) to healthy 8-12 wk old male mice after an initial Doppler ultrasound was used to determine renal blood flow (pre-Nam). Four hours after Nam injection, these same mice underwent repeated Doppler ultrasound. $P<0.05$, n=5/group.

Example 1.3. Increasing Nam Levels Increases Renal NAD and Improves Kidney Function in AKI To determine whether increasing Nam levels is beneficial, Nam or vehicle solution was administered by intraperitoneal injection followed 4 hrs later by assessment of renal Nam and NAD abundances. As shown in FIG. 17A, Nam supplementation increased renal NAD levels. Furthermore, as noted above, Nam injected intraperitoneally (400 mg/kg×1) 18 hrs after the onset of ischemic renal injury attenuated subsequent AKI (FIG. 4C).

In addition, when niacinamide was administered (400 mg/kg intraperitoneal×1) to healthy 8-12 wk old male mice, renal blood flow, a key determinant of acute and chronic organ function, was improved.

These results suggest that NAD-boosting approaches may not only be effective at prevention of AKI, but may also be considered as therapies.

Example 1.4. NNMT Plays a Key Role in NAD-Mediated Renal Protection

Figure 18A:
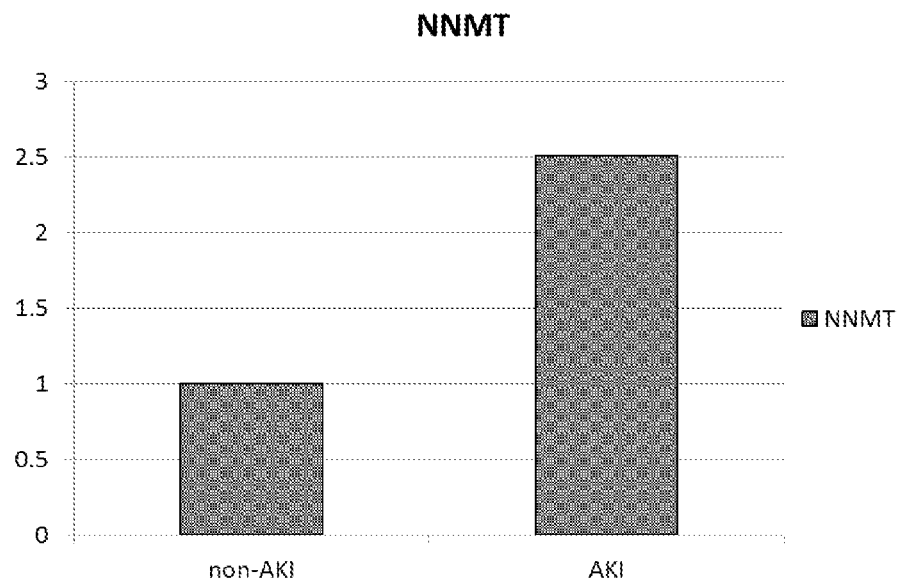
FIG. 18A: A graph showing levels of NNMT mRNA in post-ischemic (AKI) mouse kidneys and non-AKI control mouse kidneys, indicating a marked AKI-associated induction of this gene's expression.

N'-Nicotinamide Methyltransferase (NNMT) catalyzes the N-methylation of nicotinamide (NAM) using S-adenosylmethionine (SAM) as a methyl donor. NNMT is the sole mechanism for removal of niacinamide from the pool that cycles back toward synthesizing NAD. NNMT is abundant in the kidney, and immunostaining of a kidney section from a healthy volunteer for NNMT demonstrated positivity in renal tubular cells (see proteinatlas.org). These are the same cells that are injured in AKI, that express high endogenous levels of PGC1alpha, and in which over-expression of PGC1alpha can confer organwide protection against AKI. NNMT is therefore present in the cells that are the major target in AKI and that respond to genetic manipulations to boost NAD levels to confer organwide protection. Although previous reports have discussed a role of NNMT in renal cancer (see, e.g., Kim et al., Cancer Epidemiol Biomarkers Prev 22:390 (2013); Zhang et al., J Zhejiang Univ Sci B. 11(2): 136-143 (2010)), no association with non-cancerous renal disease has been suggested. As shown in FIG. 18A, NNMT mRNA is greatly increased in post-ischemic (AKI model) mouse kidneys as compared to non-AKI control mouse kidneys, indicating a marked AKI-associated induction of this gene's expression.

Figure 18B:
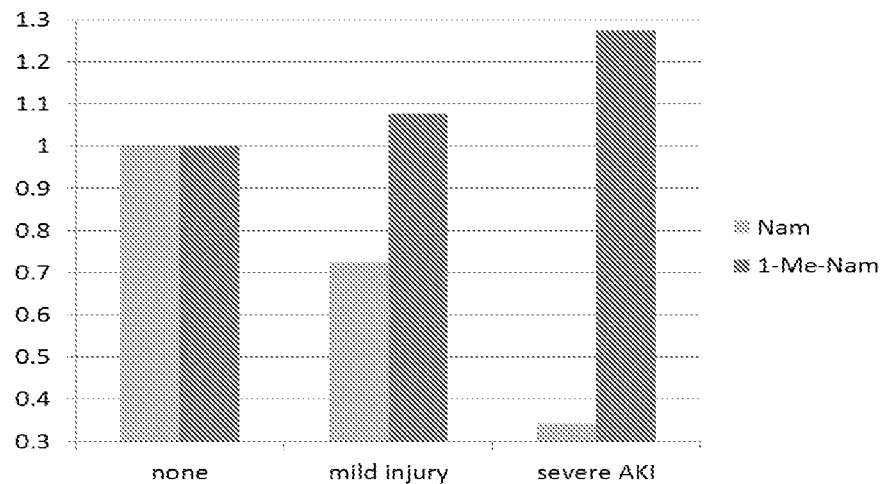
FIG. 18B: A graph showing renal tissue abundance of Nam (niacinamide, blue bars) and 1-Me-Nam (1-methyl-niacinamide, red bars) measured 24 hrs after no injury (left), mild ischemia (middle), or severe ischemic injury (severe AKI) with n=4-6 kidneys per group. The mean level for each metabolite in the no injury group was used to normalize readings in the other two groups. P<0.01 by ANOVA for each metabolite's trend across groups.

Renal tissue abundance of Nam and 1-Me-Nam (1-methyl-niacinamide) were measured 24 hrs after no injury, mild ischemia, or severe ischemic injury (severe AKI); the results are shown in FIG. 18B. A progressive fall in renal Nam abundance was evident as severity of renal injury increased whereas a progressive rise in renal 1-Me-Nam abundance was associated with increasing injury severity. The results are consistent with induction of the NNMT enzyme by renal stress. Thus kidney metabolite abundances support proportional induction of NNMT enzyme, the sole pathway by which Nam is removed from NAD pool for disposal.

Figure 18C:
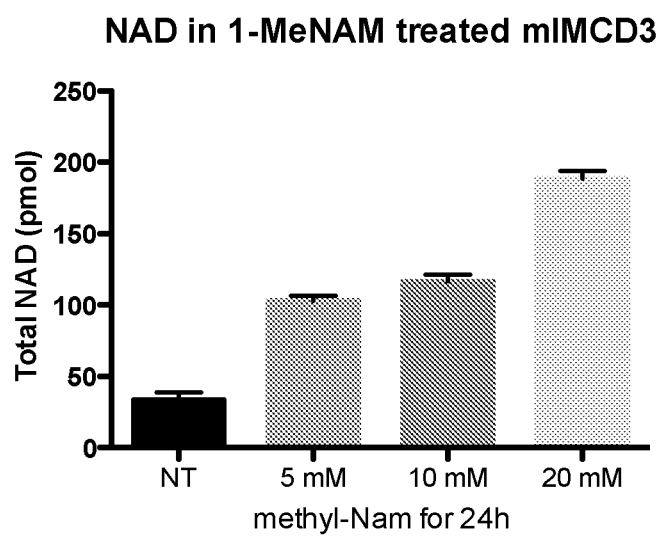
FIG. 18C: Inhibition of NNMT in cultured renal tubular cells (IMCD3) by 24 hr exposure to indicated concentration of 1-Me-Nam, the reaction product of NNMT indicates dose-dependent induction of NAD, proposing NNMT inhibition as a viable pathway for boosting NAD levels in the kidney.

Furthermore, inhibition of NNMT is therapeutically useful. NNMT was inhibited in cultured renal tubular cells (IMCD3) by 24 hr exposure to 1-Me-Nam, the reaction product of NNMT-mediated methylation of Nam. The results, shown in FIG. 18C, indicated a dose-dependent induction of NAD, proposing NNMT inhibition as a viable pathway for boosting NAD levels in the kidney.

Example 2. PGC1α as a Marker of Renal Recovery Following Kidney Transplantation; NAM and NAM Pathway Agonists Facilitate Organ Protection Delayed graft function (DGF) affects ~30% of kidneys transplant recipients who received kidneys from deceased donors and is a type of AKI. DGF is defined as the need for dialysis within 7 days of transplant and negatively impacts allograft survival. Recovery is defined as the combination of (A) independence from dialysis (i.e., no supportive measures needed to "replace" kidney artificially) and (B) serum creatinine <2.0 mg/dl. Currently, no marker exists to predict time to organ recovery following transplant. To identify a marker to predict renal recovery following kidney transplantation, tissue biopsy samples were used from a retrospective cohort study of patients who underwent renal transplant at BIDMC from 01/01/08 to 06/30/14 and who received a renal allograft biopsy for DGF within 30 days of transplant. Patient tissue biopsy samples were excluded from the study if the patients did not undergo a renal allograft biopsy, if the tissue biopsy was performed greater than 30 days after transplantation, or if the tissue biopsy showed findings other than DGF. Immunostaining and scoring for the mitochondrial biogenesis regulator PGC1α was conducted in a blinded fashion as previously described.

Figure 19A:
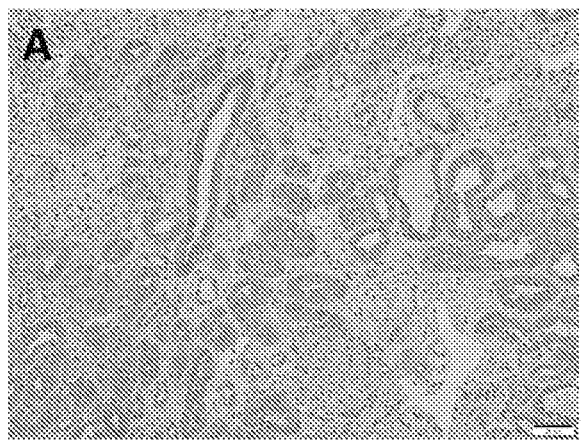
FIGS. 19A-B: Renal immunostaining for PGC1α indicated recovering function of kidney graft. A, Representative immunostaining (brown) for PGC1α in a 73-year-old Caucasian man with hypertensive (HTN) nephrosclerosis as his diagnosis for end-stage renal disease (ESRD). His kidney graft had 19 hours of cold ischemia (CIT) followed by 1 hour of warm ischemia time (WIT). The kidney did not immediately work after implantation, so he underwent hemodialysis (HD) for the first 16 post-operative days (POD), and a biopsy was performed on POD 12. B, Representative immunostaining (brown) for PGC1α in a 60-year-old African American woman with polycystic kidney disease (PKD), received a donor-cardiac death (DCD) kidney transplant with the indicated CIT and WIT as above (a).
Figure 19B:
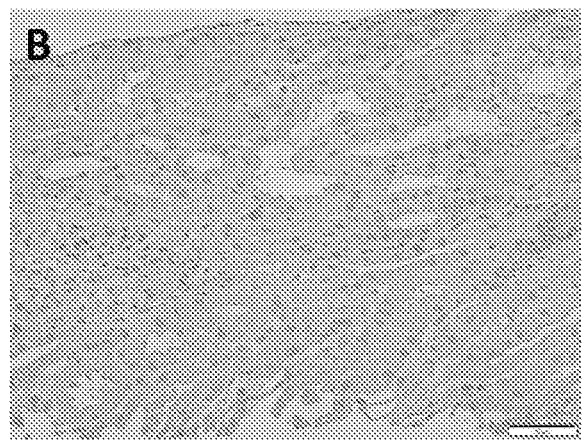
Figure 20:
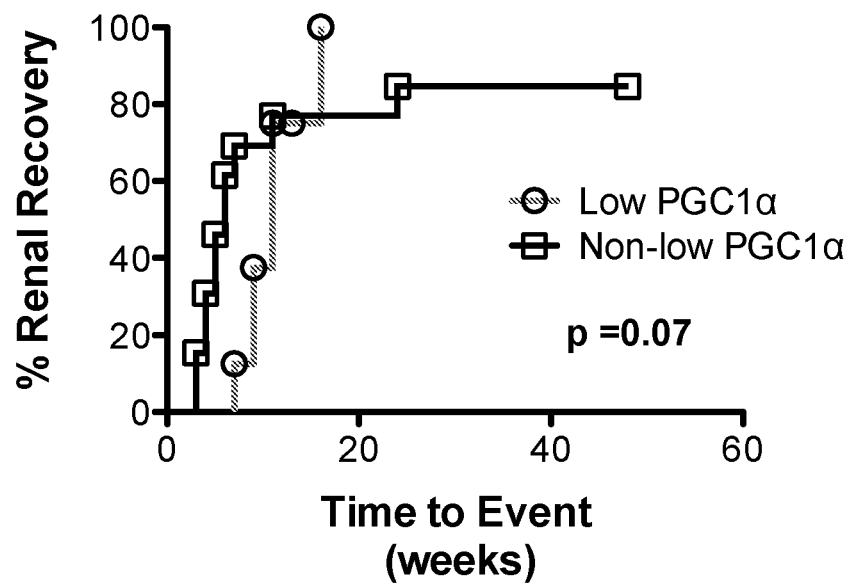
FIG. 20: Renal recovery in 21 subjects whose kidney biopsies were analyzed for PGC1α expression by immunostaining. Time to renal recovery was defined as the absence of hemodialysis and the achievement of a serum creatinine <2.0 mg/dl. p=0.07.

Of the 21 subjects included in the study, two examples are provided (FIG. 19A, B). FIG. 19A is a representative immunostaining for PGC1α in a patient whose kidney did not immediately work after implantation and underwent hemodialysis for the first 16 post-operative days (POD). The PGC1α staining score (determined as discussed above for FIG. 4) was the highest intensity (4/4) on the biopsy specimen taken on POD 12. With recovering function in his kidney graft, he was able to come off dialysis four days after the biopsy. The patient's serum creatinine (SCr), an inverse measure of kidney function, was down to 2.0 mg/dl by 4-weeks post-operation, indicating good graft function. In contrast, FIG. 19B is a representative immunostaining for PGC1α in a patient whose kidney also did not immediately work after implantation. Because of DGF, hemodialysis was required POD 1-101. A biopsy taken on POD 10 shows very low staining (1/4) for PGC1α, consistent with a prolonged period to functional recovery of the graft.

To determine whether renal recovery following kidney transplantation could be predicted based on PGC1α immunostaining, time to renal recovery was plotted for the 21 subjects included in the study (FIG. 20). Time to renal recovery was defined as the absence of hemodialysis and the achievement of a serum creatinine <2.0 mg/dl. In the group with low staining (1/4), median recovery time was shifted to the right as compared to the groups without low staining, i.e. non-low PGC1α, (scores 2, 3 or 4 out of 4) (p=0.07).

Figure 21:
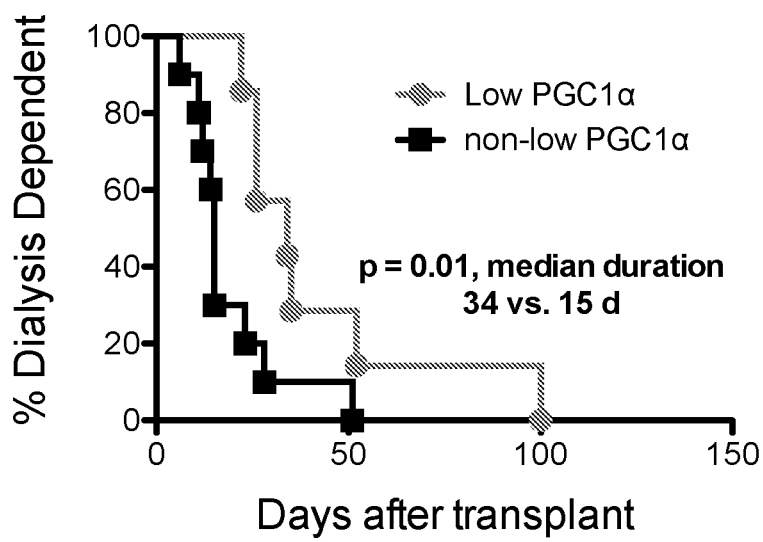
FIG. 21: Dialysis-dependence in 21 subjects whose kidney biopsies were analyzed for PGC1α expression by immunostaining. These data examine the time trend for patients being able to stop dialysis after receiving a kidney transplant among those who received a delayed graft function (DGF) diagnosis. Dialysis-dependence was defined as the number of post-operative days (POD) after transplant that the subject continued to be prescribed dialysis. Analyzed by Wilcoxon test, p=0.04
Figure 22:
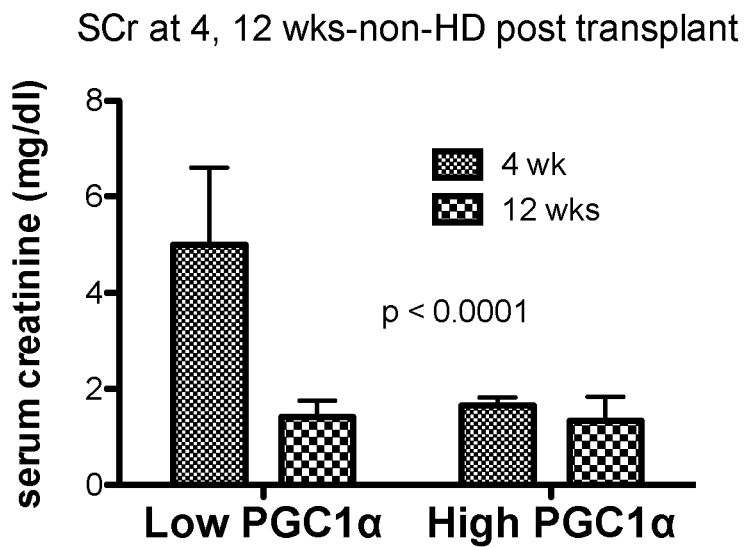
FIG. 22: Serum creatinine in the fraction of the cohort off dialysis by four weeks after transplant. Low PGC1α staining in the biopsy was associated with a higher serum creatinine level, i.e., poorer kidney function, than those who did not exhibit low staining, i.e., non-low PGC1α. P-value by two-way ANOVA, p<0.0001.

To better define the predictive power of PGC1α immunostaining on recovery, the time trend for patients being able to stop dialysis after receiving a kidney transplant among those who received a delayed graft function (DGF) diagnosis was examined (FIG. 21). Dialysis-dependence was defined as the number of POD after transplant that the subject continued to be prescribed dialysis. As shown in FIG. 21, the median time to desist dialysis support-indicating adequate functional recovery—was 16 days among subjects whose biopsy PGC1α score was 2, 3 or 4 out of 4 as compared to 35.5 days for the subjects with low score (1/4) (p=0.04). Thus, a low PGC1α staining intensity at the time of biopsy-made diagnosis of DGF was associated with a longer future period of graft non-function. Furthermore, low PGC1α staining in the biopsy was associated with a higher serum creatinine at 4 weeks after transplant, indicative of poorer kidney function, than those who did not exhibit low staining, i.e., non-low PGC1α. However, there was no significant difference in serum creatinine levels at 12 weeks after transplant.

Figure 23A:
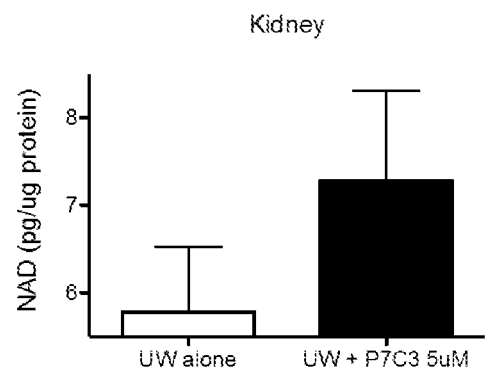
FIGS. 23A-C: NAMPT stimulation with P7C3 or excess NAMPT substrate Niacinamide (Nam) can boost NAD levels and may be organ-protective. A, To mimic donor organ harvest, deeply anesthetized mice were flushed intravascularly with ice-cold UW Belzer solution, then placed into ice cold solutions of UW-Belzer with or without 5 µM of P7C3, NAMPT agonist. After 16 hours for the explanted kidneys, organs were analyzed for levels of NAD (pg/µg of protein). B, To mimic donor organ harvest, deeply anesthetized mice were flushed intravascularly with ice-cold UW Belzer solution, then placed into ice cold solutions of UW-Belzer with or without 500 µM, 1 mM or 10 mM Nam. After 3 hours for the explanted hearts, organs were analyzed for levels of NAD (pg/µg of protein). C, NAMPT is the rate-limiting enzyme for the conversion of Nam to NAD via the intermediate NMN (nicotinamide mononucleotide). The results suggested that NAMPT stimulation with P7C3 or excess NAMPT substrate Nam can boost NAD levels during the preservation period and may be organ-protective.
Figure 23B:
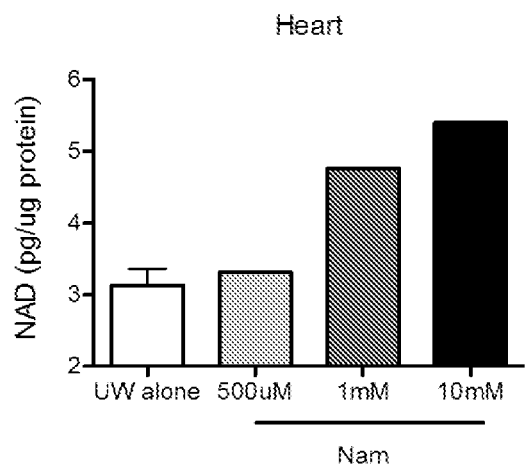

To further expand upon the results from the retrospective cohort of patient study, the conditions of donor organ harvest were mimicked using mice in hopes of improving post-implantation graft performance (FIG. 23). In this experiment, kidney and heart were harvested and Nam or P7C3, a NAMPT agonist, were added to the preservation solution. Upon incubation of kidney with P7C3 in the preservation solution, NAD levels increased as compared to kidney incubated with the UW Belzer solution alone (FIG. 23A). Furthermore, upon incubation of heart with different concentrations of Nam in the preservation solution, NAD levels increased as compared to heart incubated with the UW Belzer solution alone (FIG. 23B). This result demonstrates that Nam or niacinamide (NAM) pathway agonists in perfusion or preservation solutions can improve post-implantation graft performance.

Figure 23C:
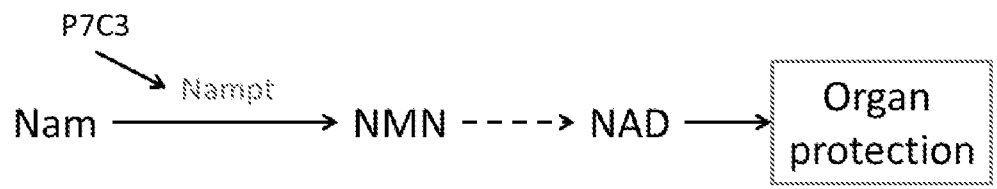

Taken together, these results indicated that PGC1α predicts the timing of recovery among those with DGF and that Nam or niacinamide (NAM) pathway agonists can facilitate organ protection through increasing NAD levels (FIG. 23C).

Example 3. PGC1α in Cardiac Ischemia and Rescue by Nam or Niacinamide (NAM) Pathway Agonists As noted above, gene expression levels of enzymes that convert dietary tryptophan to NAD+ and related enzymes (see FIG. 3C) was determined by qPCR for transcripts in PGC1α KO hearts using the methods described above. The results showed that levels of the enzymes were suppressed at baseline relative to wildtype littermates (see FIG. 16).

Figure 24:
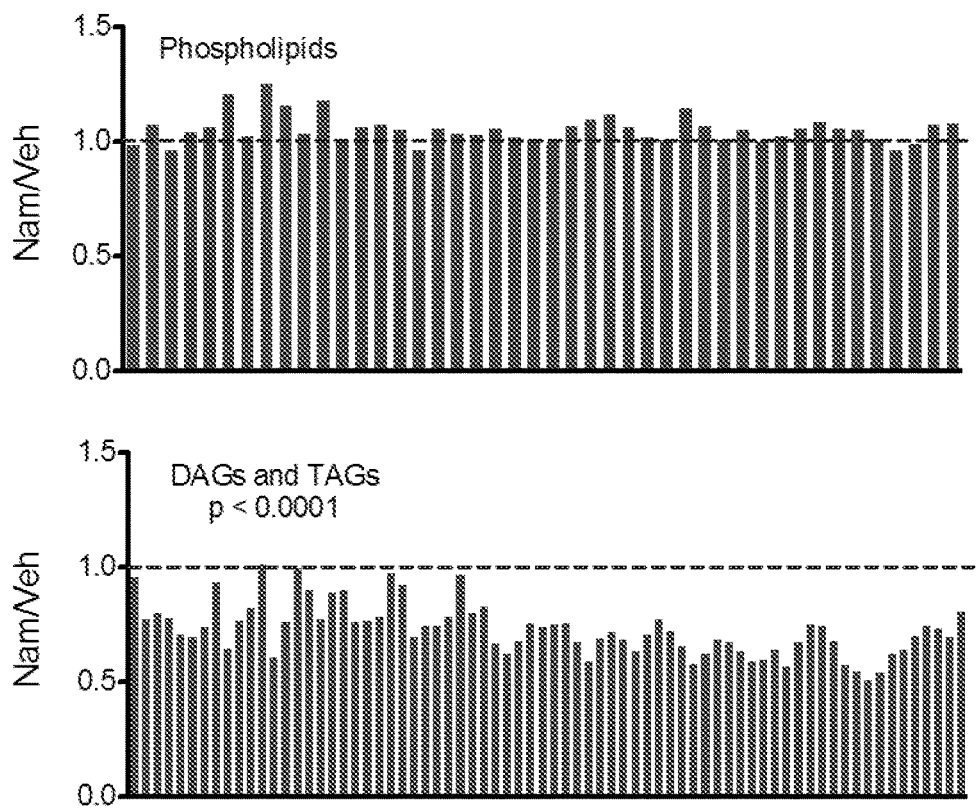
FIG. 24: Exogenous Nicotinamide (Nam) specifically lowers intracardiac storage fats. Intracardiac phospholipids are largely unaltered after administering Nam (400 mg/kg IP, top graph) whereas di- and tri-acylglycerols (DAG, TAG) decline markedly and across classes (lower graph). Each bar represents a unique molecular weight DAG or TAG.

The heart oxidizes fats preferentially to contraction. Organ levels of Nam are reduced in PGC1α$^{-/-}$ animals, and administration of Nam recapitulates metabolic and functional effects of PGC1α, suggesting Nam as a potential mimetic of this pathway. As shown in FIG. 24, intracardiac phospholipids were largely unaltered after administering Nam (400 mg/kg IP) to PGC1α$^{-/-}$ animals, whereas di- and tri-acylglycerols (DAG, TAG) decline markedly and across classes. This is similar to what occurs in the kidney, see FIGS. 5B and 6G.

Figure 25:
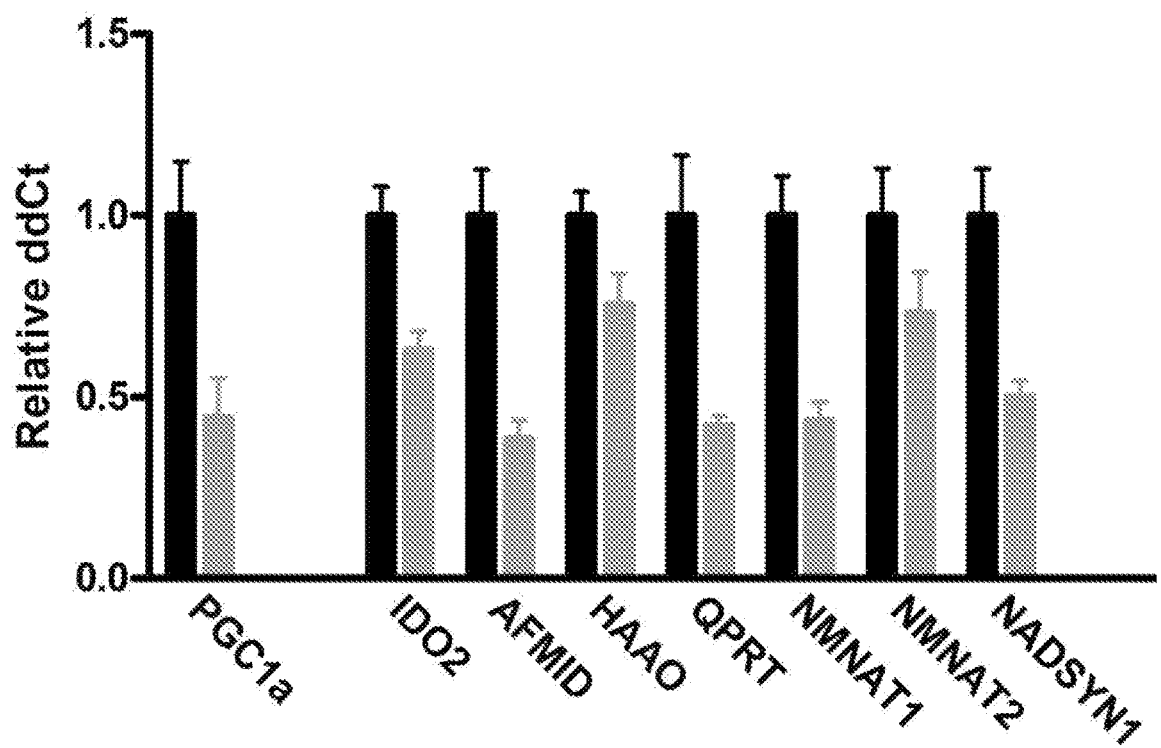
FIG. 25: Myocardial infarction attenuates the de novo NAD+ biosynthetic pathway. Intracardiac transcript abundance for enzymes of the de novo NAD+ biosynthetic pathway was measured Twenty-four hrs after inducing experimental myocardial infarction. Black bars, before MI; grey bars, after MI.
Figure 26:
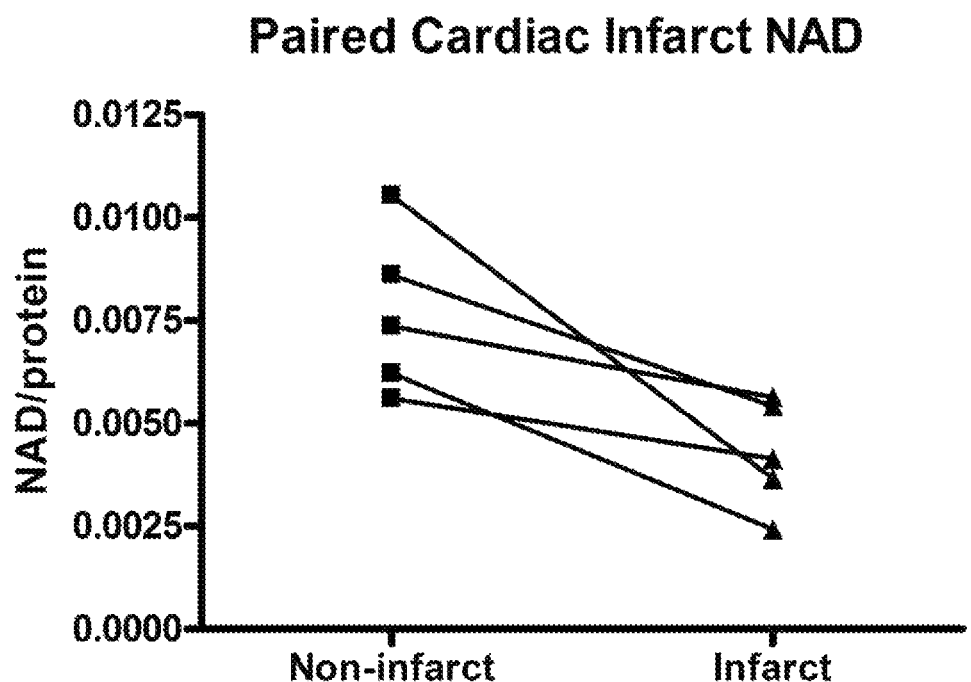
FIG. 26: Intracardiac NAD+ declines after myocardial infarction in the non-necrotic penumbra. Twenty-four hrs after inducing experimental myocardial infarction by coronary artery ligation, intracardiac NAD was assessed. Necrotic areas had nearly undetectable NAD, but even the viable penumbra surrounding infarct tissue exhibited markedly reduced NAD compared to non-infracted regions.

To further evaluate the role of PGC1α and NAD+ biosynthesis in the heart, and in recovery from cardiac ischemia, intracardiac transcript abundance was measured for enzymes of the de novo NAD+ biosynthetic pathway that are modulated by PGC1α expression (see FIG. 3C) twenty-four hours after inducing experimental myocardial infarction by coronary artery ligation. As shown in FIG. 25, myocardial infarction attenuates the de novo NAD+ biosynthetic pathway in cardiac tissue. Furthermore, the cardiac post-ischemic response (MI) may be PGC1α-dependent at least in part. In addition, intracardiac NAD levels were assessed at the same time point. Necrotic areas had nearly undetectable NAD, but even the viable penumbra surrounding infarct tissue exhibited markedly reduced NAD compared to non-infracted regions, as shown in FIG. 26. This suggests an opportunity to rescue "at-risk" myocardium with NAD+ boosting strategies.

In addition, longer-term effects of PGC1α deficiency were evaluated. Two weeks after a 45-minute transient occlusion of the left coronary artery in wild type (WT) and PGC1α$^{-/-}$ mice (KO), pressure volume loops were performed to assess cardiac parameters.

Figure 27A:
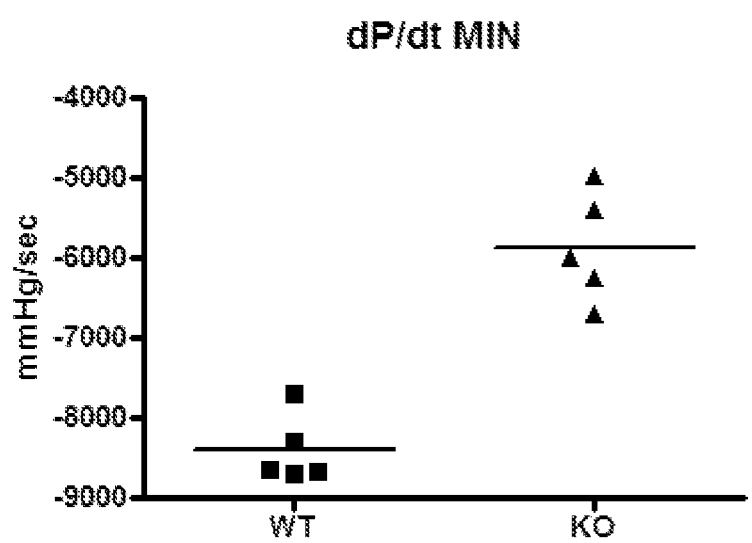
FIGS. 27A-C: Evidence of post-ischemic diastolic dysfunction related to PGC1α deficiency. Two weeks after transient occlusion of the left coronary artery, pressure volume loops were performed in wild type (WT) and PGC1α$^{-/-}$ mice (KO). dP/dt min, change in left ventricular pressure per unit time during diastole; dP/dt max, change in left ventricular pressure per unit time during systole; LVV, left ventricular chamber dilation measured as volume.
Figure 27B:
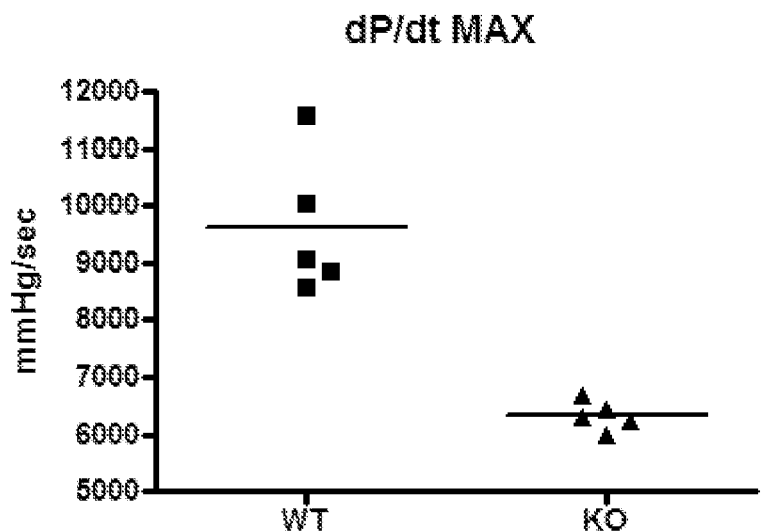
Figure 27C:
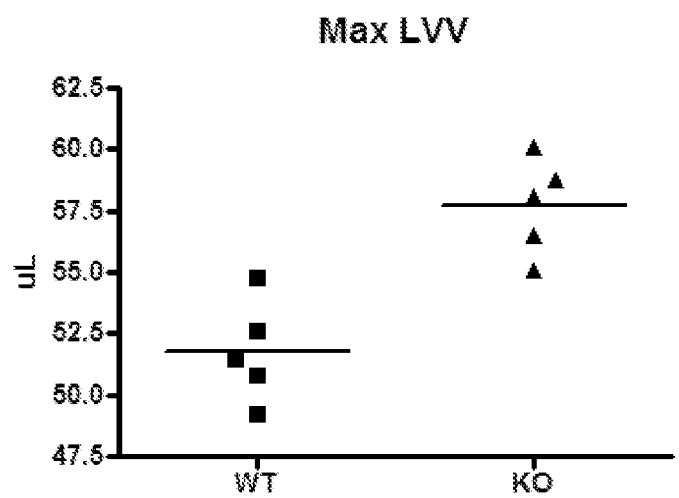

The change in left ventricular pressure per unit time (dP/dt min) is negative as the chamber relaxes during diastole to fill with blood prior to systolic ejection, and then dP/dt max is positive as the chamber contracts during systole to eject blood into the body. Systolic dysfunction culminates in left ventricular chamber dilation measured as volume (LVV). The results showed that post-ischemic KO hearts were not able to relax as well as post-ischemic wildtype littermate hearts (FIG. 27A), post-ischemic KO hearts are unable to contract as powerfully as post-ischemic wildtype littermate hearts (FIG. 27B), and LVV (FIG. 27C) was substantially elevated in post-ischemic KO hearts vs. post-ischemic wildtype littermate hearts. This provides additional evidence of post-ischemic diastolic dysfunction related to PGC1α/NAD deficiency.

Figure 28A:
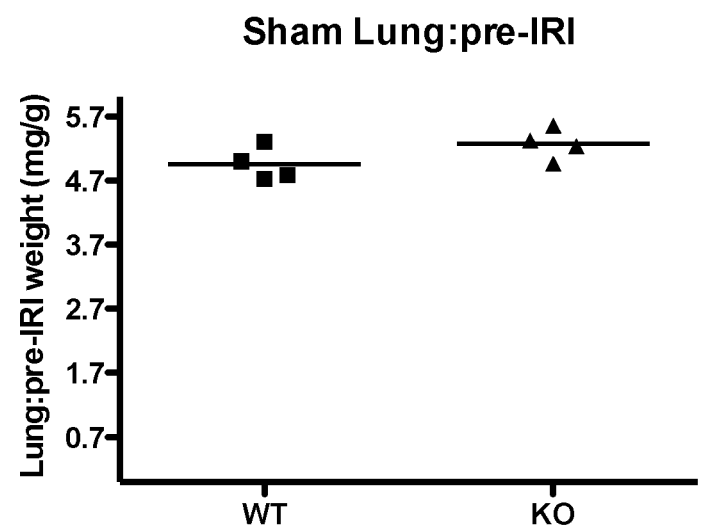
FIGS. 28A-B: PGC1α deficiency exacerbates extracardiac aspects of heart failure following ischemia-reperfusion. Before (28A) and twenty-four hrs after (28B) inducing experimental myocardial infarction by left coronary artery ligation (IRI), lungs were collected to determine weight.
Figure 28B:
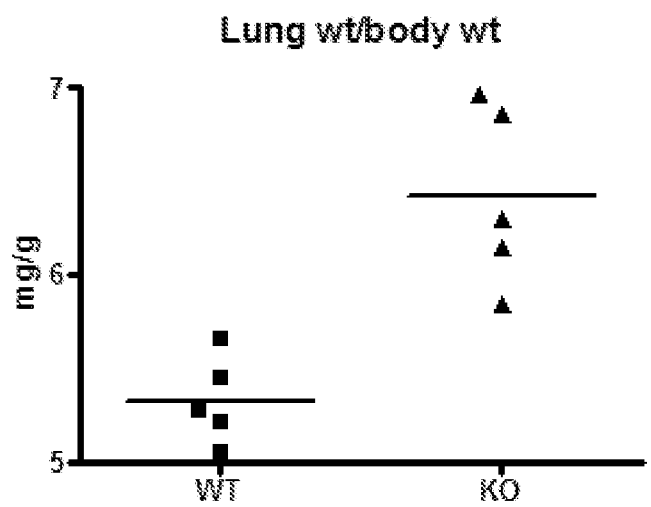

To further determine whether PGC1α deficiency exacerbates extracardiac aspects of heart failure following ischemia-reperfusion, lungs were collected to determine weight twenty-four hours after inducing experimental myocardial infarction by left coronary artery ligation (IRI). Lung weight rises with water content, which increases as hydraulic pressure in the lung circulation rises abnormally because the left chamber of the heart is unable to relax and eject blood effectively. As shown in FIG. 28A, prior to IRI, there was no difference in weight, but after IRI, lungs from KO mice were heavier (FIG. 28B). In addition, cardiac ischemia-reperfusion injury in PGC1α KO mice yielded aneurysmal changes that lead to heart rupture. Five KO mice and 5 wildtype littermates were subjected to 45 minutes of cardiac ischemia by transient occlusion of the left coronary artery. Two out of the five KO mice developed aneurysmal rupture, whereas none of the 5 wildtype littermates exhibited this severe complication of ischemic injury.

Figure 29:
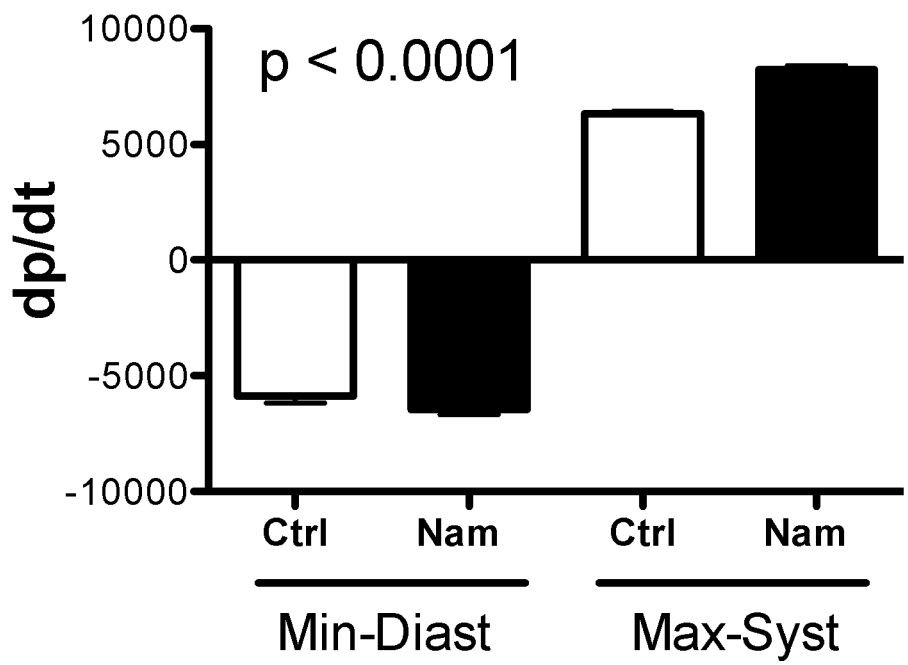
FIG. 29: Evidence of post-ischemic diastolic and systolic dysfunction ameliorated by Nicontinamide (Nam). Two weeks after 45 minutes transient occlusion of the left coronary artery, pressure volume loops were performed in PGC1α KO mice treated with vehicle control (Ctrl) or Nam (400 mg/kg IP). Both relaxation and contraction were improved by Nam.

To determine whether post-ischemic diastolic and systolic dysfunction ameliorated by Nicotinamide (Nam), the pressure volume loop experiments described above were performed in PGC1α KO mice treated with vehicle control or Nam (400 mg/kg IP) administered one dose before IRI, then two doses after. As noted above, the change in left ventricular pressure per unit time (dP/dt min) is negative as the chamber relaxes during diastole to fill with blood prior to systolic ejection, when the change in pressure per time is maximal (dp/dt max). As shown in FIG. 29, both relaxation and contraction were improved by Nam, which appeared to act as a PGC1α mimetic.

Figure 30:
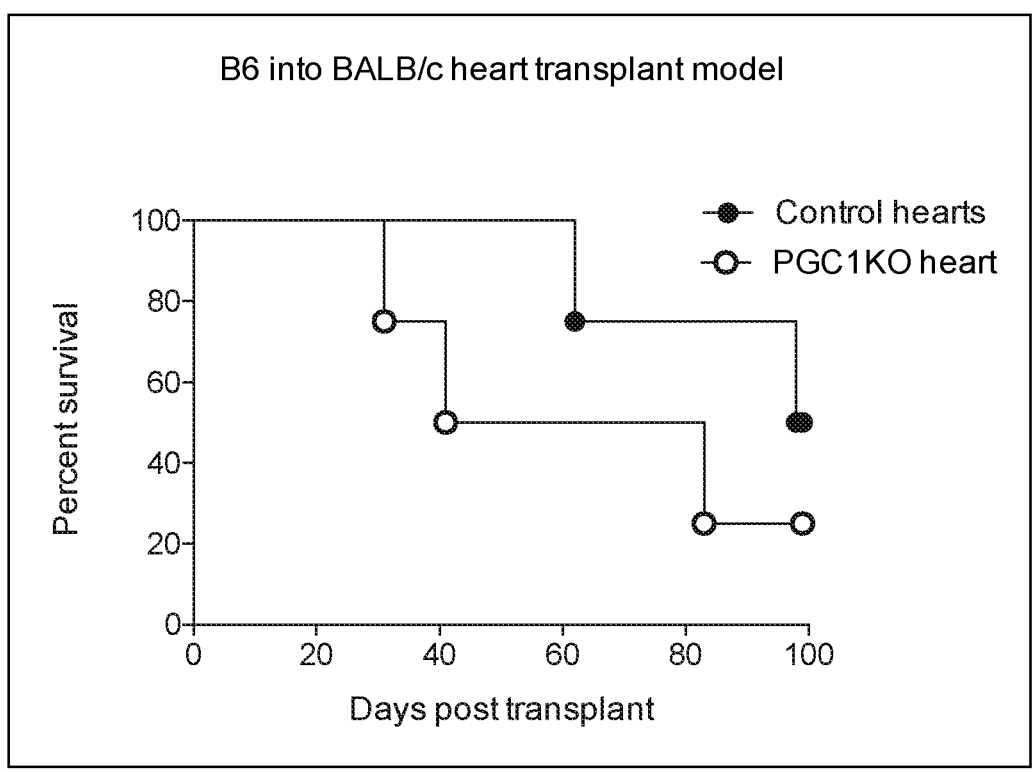
FIG. 30. Allogeneic cardiac transplantation may have PGC1α-dependent outcomes. Wildtype or PGC1α KO hearts from a B6 mouse background were transplanted heterotopically into BALB/c mice. Percent survival determined by assessing transplant cardiac contraction by daily palpation.

Further experiments were performed to determine whether, in addition to MI, other forms of cardiac ischemia including cardiac transplantation-associated ischemic injury have PGC1α-dependent outcomes. Wildtype or PGC1α KO hearts from a B6 mouse background were transplanted heterotopically into BALB/c mice after a period of 6 hours of cold ischemia. The mice were treated with CTLA4-Ig on post-operative day 2 to control the adaptive immune response and isolate functional impacts arising from ischemia-reperfusion injury. Percent survival was determined by assessing transplant cardiac contraction by daily palpation. As shown in FIG. 30, survival was decreased in the PGC1α KO animals as compared to the wild type.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating acute kidney injury (AKI) in a subject, wherein the subject is in the hospital or will be hospitalized, the method comprising administering to a subject in need thereof a therapeutically effective amount of a Nicotinamide adenine dinucleotide (NAD)/niacinamide (NAM) pathway agonist, wherein the NAD/NAM pathway agonist is a small molecule selected from Nicotinamide adenine dinucleotide (NAD); niacinamide (NAM); nicotinamide mononucleotide (NMN); Nicotinamide riboside (NR); and P7C3 and analogs thereof, optionally P7C3-A20.

2. The method of claim 1, wherein the AKI is delayed graft function in a subject who has received a kidney transplant.

3. The method of claim 2, further comprising diagnosing delayed graft function in the subject by a method comprising:
- obtaining a sample from the subject who has received a kidney transplant, optionally a sample comprising a tissue biopsy from the transplanted kidney in the subject, or a non-invasive surrogate thereof;
- determining a level of PGC1α in the sample, optionally using immunostaining;
- comparing the PGC1α level in the sample with one or more reference levels; and
- identifying a subject who has a PGC1α level below the reference level as having or is at risk of developing delayed graft function.

4. The method of claim 3, wherein the one or more reference levels represent a control reference that represents a normal PGC1α immunostaining score or a disease reference that represents PGC1α immunostaining score associated with delayed graft function.

5. The method of claim 1, wherein the NAD/NAM pathway agonist is niacinamide (NAM).

6. The method of claim 1, wherein the subject has had or is at risk of developing an ischemic renal injury.

7. The method of claim 1, wherein the subject has had or is at risk of developing delayed graft function.

8. A method of treating acute kidney injury (AKI) in a subject, wherein the subject is in the hospital or will be hospitalized, the method comprising administering to a subject in need thereof a therapeutically effective amount of a N'-Nicotinamide Methyltransferase (NNMT) inhibitory nucleic acid, wherein the inhibitory nucleic acid is an antisense oligonucleotide, peptide nucleic acids (PNA), or small interfering siRNA specifically targeting NNMT.

9. The method of claim 8, wherein the inhibitory nucleic acid is modified.

10. The method of claim 8 wherein the inhibitory nucleic acid includes one or more locked nucleotides.

11. A method of treating, or reducing risk of developing, acute kidney injury (AKI) in a subject, wherein the subject has acute nephrotoxic injury after being administered or exposed to a renal toxin, optionally a therapeutic agent with renal toxicity, optionally cisplatin, the method comprising administering to a subject in need thereof a therapeutically effective amount of a Nicotinamide adenine dinucleotide (NAD)/niacinamide (NAM) pathway agonist, wherein the NAD/NAM pathway agonist is Nicotinamide adenine dinucleotide (NAD); niacinamide (NAM); nicotinamide mononucleotide (NMN); Nicotinamide riboside (NR); P7C3 or an analog thereof, optionally P7C3-A20; or a N'-Nicotinamide Methyltransferase (NNMT) inhibitory nucleic acid, wherein the inhibitory nucleic acid is an antisense oligonucleotide or small interfering siRNA specifically targeting NNMT.

12. The method of claim 11, wherein the subject does not yet have AKI, but has been or will be hospitalized.

* * * * *